(12) United States Patent
Kubota et al.

(10) Patent No.: US 7,192,746 B2
(45) Date of Patent: Mar. 20, 2007

(54) α-ISOMALTOSYLTRANSFERASE, PROCESS FOR PRODUCING THE SAME AND USE THEREOF

(75) Inventors: Michio Kubota, Okayama (JP); Tomoyuki Nishimoto, Okayama (JP); Hajime Aga, Okayama (JP); Shigeharu Fukuda, Okayama (JP); Toshio Miyake, Okayama (JP)

(73) Assignee: Kabushiki Kaisha Hayashibara Seibutsu Kagaku Kenkyujo, Okayama (JP)

( * ) Notice: Subject to any disclaimer, the term of this patent is extended or adjusted under 35 U.S.C. 154(b) by 568 days.

(21) Appl. No.: 10/296,153

(22) PCT Filed: May 22, 2001

(86) PCT No.: PCT/JP01/04276

§ 371 (c)(1),
(2), (4) Date: Nov. 22, 2002

(87) PCT Pub. No.: WO01/90338

PCT Pub. Date: Nov. 29, 2001

(65) Prior Publication Data

US 2005/0009017 A1    Jan. 13, 2005

(30) Foreign Application Priority Data

May 22, 2000  (JP)  ............... 2000-149484
Jul. 28, 2000  (JP)  ............... 2000-229557

(51) Int. Cl.
*C12P 19/18*  (2006.01)
*C12N 9/10*  (2006.01)
*C12N 1/20*  (2006.01)

(52) U.S. Cl. .................. 435/97; 435/193; 435/200; 435/201; 435/72; 435/252.5; 435/252.31

(58) Field of Classification Search .................. 435/97, 435/72, 193, 201, 200, 252.5, 252.31
See application file for complete search history.

(56) References Cited

U.S. PATENT DOCUMENTS

| 4,521,252 | A |   | 6/1985 | Miyake et al. |   |
|---|---|---|---|---|---|
| RE33,047 | E |   | 9/1989 | Miyake et al. |   |
| 5,786,196 | A | * | 7/1998 | Cote et al. | .................. 435/208 |
| 5,889,179 | A |   | 3/1999 | Cote et al. |   |

FOREIGN PATENT DOCUMENTS

| EP | 0 606 753 A2 | 7/1994 |
|---|---|---|
| EP | 0 628 630 B1 | 5/1998 |
| JP | 58-23799 | 2/1983 |
| JP | 58-72598 | 4/1983 |
| JP | 7-143876 | 6/1995 |
| JP | 7-213283 | 8/1995 |

OTHER PUBLICATIONS

Okada et al., "Digestion and Fermentation of Pullulan", *Journal of Japanese Society of Nutrition and Food Science*, vol. 43, No. 1, pp. 23-29 (1990).
Oku et al., "Metabolic Fate of Ingested [$^{14}$C]-Maltitol in Man", *Journal of Nutritional Science and Vitaminology*, vol. 37, pp. 529-544 (1991).
Biely et al., "Purification and properties of Alternanase, a Novel endo-α-1,6-D-glucanase", *European Journal of Biochemistry*, vol. 226, pp. 633-639 (1994).
"Bergey's Manual® of Systematic Bacteriology, vol. 2", edited by Peter H. A. Sneath et al., Baltimore: Williams & Wilkins (1986).
French et al. "Studies on the Schardinger Dextrins. The Preparation and Solubility Characteristics of Alpha, Beta and Gamma Dextrins", *Journals of American Chemical Society*, vol. 71, pp. 353-358 (1949).
Côté et al., "Enzymically Produced Cyclic α-1,3-linked and α-1,6-linked Oligosaccharides of D-glucose", *European Journal of Biochemistry*, vol. 226, pp. 641-648 (1994).
"Biseibutsu-no-Bunrui-to-Dotel" (Classification and Identification of Microorganisms), edited by Takeji Hasegawa, Tokyo: Japan Scientific Societies Press (1985).
"Intestinal Flora and Dietary Factors", edited by Mitsuoka D.V.M., Ph.D., Proceedings of IV. Riken Symposium on Intestinal Flora, Tokyo, Japan Scientific Societies Press (1983).
Côté, Gregory L. et al., "The hydrolytic and transferase action of alternanase on oligosaccharides", *Carbohydrate Research*, vol. 332, pp. 373-379 (2001).
Côté, Gregory L. et al., "The hydrolytci and transferase action of alternanase on oligosaccharides", *Carbohydrate Research*, vol. 332, pp. 373-379 (2001).

* cited by examiner

*Primary Examiner*—Francisco Prats
(74) *Attorney, Agent, or Firm*—Browdy and Neimark, PLLC

(57) ABSTRACT

The object of the present invention is to provide an α-isomaltosyl-transferring enzyme which forms a cyclotetrasaccharide having the structure of cyclo{→6)-α-D-glucopyranosyl-(1→3)-α-D-glucopyranosyl-(1→6)-α-D-glucopyranosyl-(1→3)-α-D-glucopyranosyl-(1→} from a saccharide having a glucose polymerization degree of at least three and having both the α-1,6 glucosidic linkage as a linkage at the non-reducing end and the α-1,4 glucosidic linkage other than the linkage at the non-reducing end; microorganisms which produce the enzyme; process for producing the enzyme; cyclotetrasaccharide or saccharide compositions comprising the same; and uses thereof.

18 Claims, 20 Drawing Sheets

SEQUENCE LISTING

```
<160> NUMBER OF SEQ ID NOS: 10

<210> SEQ ID NO 1
<211> LENGTH: 8
<212> TYPE: PRT
<213> ORGANISM: Bacillus globisporus

<400> SEQUENCE: 1

Ile Asp Gly Val Tyr His Ala Pro
1               5

<210> SEQ ID NO 2
<211> LENGTH: 8
<212> TYPE: PRT
<213> ORGANISM: Bacillus globisporus

<400> SEQUENCE: 2
```

```
Gly Asn Glu Met Arg Asn Gln Tyr
1               5

<210> SEQ ID NO 3
<211> LENGTH: 8
<212> TYPE: PRT
<213> ORGANISM: Bacillus globisporus

<400> SEQUENCE: 3

Ile Thr Thr Trp Pro Ile Glu Ser
1               5

<210> SEQ ID NO 4
<211> LENGTH: 8
<212> TYPE: PRT
<213> ORGANISM: Bacillus globisporus

<400> SEQUENCE: 4

Trp Ala Phe Gly Leu Trp Met Ser
1               5

<210> SEQ ID NO 5
<211> LENGTH: 6
<212> TYPE: PRT
<213> ORGANISM: Bacillus globisporus

<400> SEQUENCE: 5

Asn Trp Trp Met Ser Lys
1               5

<210> SEQ ID NO 6
<211> LENGTH: 8
<212> TYPE: PRT
<213> ORGANISM: Bacillus globisporus

<400> SEQUENCE: 6

Thr Asp Gly Gly Glu Met Val Trp
1               5

<210> SEQ ID NO 7
<211> LENGTH: 8
<212> TYPE: PRT
<213> ORGANISM: Bacillus globisporus

<400> SEQUENCE: 7

Asn Ile Tyr Leu Pro Gln Gly Asp
1               5

<210> SEQ ID NO 8
<211> LENGTH: 10
<212> TYPE: PRT
<213> ORGANISM: Arthrobacter ramosus

<400> SEQUENCE: 8

Asp Thr Leu Ser Gly Val Phe His Gly Pro
1               5                   10

<210> SEQ ID NO 9
<211> LENGTH: 10
<212> TYPE: PRT
<213> ORGANISM: Bacillus globisporus

<400> SEQUENCE: 9

Ile Asp Gly Val Tyr His Ala Pro Asn Gly
1               5                   10
```

```
<210> SEQ ID NO 10
<211> LENGTH: 10
<212> TYPE: PRT
<213> ORGANISM: Bacillus globisporus

<400> SEQUENCE: 10

Ile Asp Gly Val Tyr His Ala Pro Tyr Gly
1               5                   10
```

α-ISOMALTOSYLTRANSFERASE, PROCESS FOR PRODUCING THE SAME AND USE THEREOF

TECHNICAL FIELD

The present invention relates to an α-isomaltosyl-transferring enzyme, its preparation and uses, more particularly, to a novel α-isomaltosyl-transferring enzyme, microorganism capable of producing the enzyme, process for producing the enzyme, α-isomaltosyl-transferring method using the enzyme, process for producing either a cyclotetrasaccharide having the structure of cyclo{→6)-α-D-glucopyranosyl-(1→3)-α-D-glucopyranosyl-(1→6)-α-D-glucopyranosyl-(1→3)-α-D-glucopyranosyl-(1→} obtainable by using the enzyme, or a saccharide composition comprising the cyclotetrasaccharide; and further to a cyclotetrasaccharide having the structure of cyclo{→6)-α-D-glucopyranosyl-(1→3)-α-D-glucopyranosyl-(1→6)-α-D-glucopyranosyl-(1→3)-α-D-glucopyranosyl-(1→}, saccharide composition comprising the cyclotetrasaccharide, and composition comprising the cyclotetrasaccharide.

BACKGROUND ART

There have been known saccharides, which are composed of glucose molecules as constituent saccharides, such as amyloses, amylodextrins, maltodextrins, maltooligosaccharides, and isomaltooligosaccharides as partial starch hydrolysates. These saccharides are, usually, known to exhibit reducibility and to have reducing and non-reducing groups at their both molecular ends. In general, it has been known that partial starch hydrolysates having a relatively high reducing power on a dry solid basis (d.s.b.) usually have a relatively low molecular weight and viscosity and a relatively high sweetness, and have the demerits that they easily induce the amino carbonyl reaction, for example, with substances having amino groups such as amino acids and proteins to cause browning or unsatisfactory smell and facilitate the quality deterioration. To improve the demerits, there has long been desired a method for lowering or eliminating the reducing power without altering glucose molecules as constituent saccharides of partial starch hydrolysates. For example, as disclosed in *Journal of American Chemical Society*, Vol. 71, pp. 353–358 (1949), it was reported that a method for forming α-, β-, and γ-cyclodextrins, composed of 6–8 glucose molecules linked together via the α-1,4 glucosidic linkage by contacting starches with an amylase derived from a microorganism of the species *Bacillus macerans*. Today, these cyclodextrins are produced on an industrial scale and used in diversified fields which need their inherent properties such as non-reducibility, tasteless, and enclosing ability. As disclosed, for example, in Japanese Patent Kokai Nos. 143,876/95 and 213,283/95 applied for by the same applicant as the present invention, there has been known a method for producing trehalose (α,α-trehalose), composed of two glucose molecules linked together via the α,α-linkage, by contacting a non-reducing saccharide-forming enzyme and a trehalose-releasing enzyme with partial starch hydrolysates such as maltooligosaccharides. At present, trehalose has been industrially produced from starches and used in different fields which need the advantageous non-reducibility, mild- and high quality-sweetness of trehalose. As described above, trehalose having a glucose polymerization degree (DP) of two, and α-, β-, and γ-cyclodextrins having a DP of 6 to 8 are produced on an industrial scale and used in view of their advantageous properties, however, the varieties of non- or low-reducing saccharides are limited, so that more diversified saccharides other than the above-exemplified saccharides are greatly required.

Recently, a new type of cyclotetrasaccharide, composed of glucose units, was reported. *European Journal of Biochemistry*, Vol. 226, pp. 641–648 (1994) shows that a cyclic tetrasaccharide having the structure of cyclo{→6)-α-D-glucopyranosyl-(1→3)-α-D-glucopyranosyl-(1→6)-α-D-glucopyranosyl-(1→3)-α-D-glucopyranosyl-(1→} (may be called "cyclotetrasaccharide" throughout the specification) is formed by contacting alternanase, a hydrolyzing enzyme, with alternan composed of glucose residues mainly linked together via the α-1,3 and α-1,6 bonds, alternatively, and crystallizing the formed cyclic tetrasaccharide in the presence of methanol as an organic solvent.

Cyclotetrasaccharide has an ability of including compounds based on its cyclic structure and does not cause the amino carbonyl reaction due to its non-reducibility, and therefore it is expected to be processed and used with lesser fear of browning and deterioration. However, the material alternan and alternanase as an enzyme, which are essential for producing the saccharide, are not easily obtainable; and also microorganisms for producing the alternan and alternanase are not easily available.

Under these conditions, the establishment of a novel process for easily producing cyclotetrasaccharide on an industrial scale and the providing of cyclotetrasaccharide with revealed physicochemical properties are greatly expected.

DISCLOSURE OF INVENTION

The object of the present invention is to provide a novel α-isomaltosyl-transferring enzyme which forms cyclotetrasaccharide from easily available saccharides, preparation of the same, α-isomaltosyl-transferring reaction using the enzyme, cyclotetrasaccharide obtainable by the enzyme, saccharide composition comprising cyclotetrasaccharide, preparation of the saccharide composition, and composition comprising cyclotetrasaccharide or the saccharide composition.

To solve the above object, the present inventors widely screened a microorganism which produces a novel enzyme that forms cyclotetrasaccharide from isomaltooligosaccharides, particularly, panose, with an expectation of obtaining such an enzyme. As a result, they isolated novel microorganisms of the genus *Bacillus* (hereinafter may be called "Strain C9", "Strain C11", and "Strain N75"), which were isolated from soils in Okayama, Japan; and novel microorganisms of the genus *Arthrobacter* (hereinafter may be called "Strain S1" and "Strain "A19"), which were isolated from soils in Shimotakai-gun, Nagano, Japan and in Okayama-shi, Okayama, Japan, respectively, have an ability of producing the above-identified enzyme.

The present inventors found that all the microorganisms of the above-identified C9, C11, N75, S1 and A19 strains produce a novel enzyme or a novel α-isomaltosyl-transferring enzyme which forms cyclotetrasaccharide by acting on a saccharide having a glucose polymerization degree of at least three and having both the α-1,6 glucosidic linkage, as a linkage at the non-reducing end such as in panose and isomaltosylmaltose, and the α-1,4 glucosidic linkage other than the above linkage (hereinafter may be abbreviated as "α-isomaltosyl-glucosaccharide"). The present inventors also revealed the properties of the above-identified enzyme, established the preparation, and established both the transferring reaction using the enzyme and the preparation of cyclotetrasaccharide and saccharide composition comprising the saccharide formed by the enzyme. The present inventors studied the physicochemical properties of cyclotetrasaccharide and revealed that cyclotetrasaccharide exists in a penta- to hexa-hydrous, monohydrate, or anhydrous crystalline form; or in an amorphous form, which are all easily collected by crystallizing in supersaturated aqueous solutions of cyclotetrasaccharide without using organic solvents such as methyl- or ethyl-alcohol. The present inventors also found that the cyclotetrasaccharide thus obtained has the following useful properties: It has an ability of including volatile ingredients such as ethyl alcohol and acetic acid, does not cause the amino carbonyl reaction, less causes browning and deterioration per se, has satisfactory thermal and pH stability, has a mild and lesser sweetness that does not deteriorate the flavor and taste of foods, and effectively functions as a substantially non-fermentable and non-assimilable dietary fiber. The present inventors further established compositions comprising cyclotetrasaccharide or saccharide composition with cyclotetrasaccharide, for example, high-quality foods with a satisfactory flavor and taste, low-caloric foods, dietary foods, stable and high-quality cosmetics, stable and highly-active pharmaceuticals, and preparations thereof; and thus accomplished this invention.

BEST MODE FOR CARRYING OUT THE INVENTION

Figure 1:
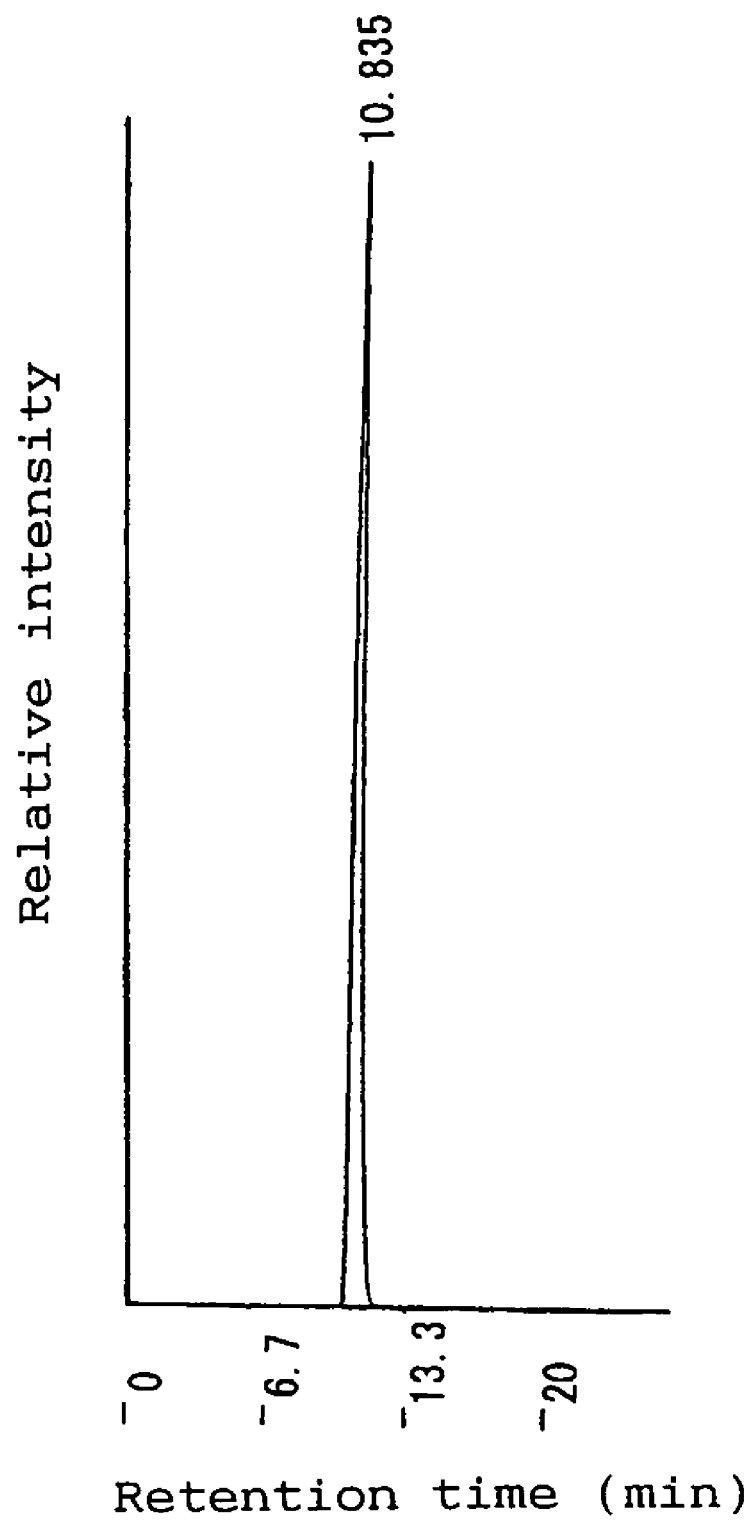
FIG. 1 is an elution pattern of a saccharide obtained by the α-isomaltosyl-transferring enzymatic reaction according to the present invention, when determined on high-performance liquid chromatography.

The following are the identification results of Strain C9, Strain C11, Strain N75, and Strain A19, which all belong to the microorganisms of the genus *Bacillus;* and Strain S1 and Strain A19, which all belong to the microorganisms of the genus *Arthrobacter.* The identification tests were conducted in accordance with the methods as described in "*Biseibutsu-no-Bunrui-to-Dotei*" (Classification and Identification of Microorganisms), edited by Takeji Hasegawa, published by Japan Scientific Societies Press, Tokyo, Japan (1985).

<Strain C9>

<A. Morphology>
 Characteristics of cells when incubated at 27° C. in nutrient broth agar
 Existing usually in a rod shape of 0.5–1.0 μm×1.5–5.0 μm,
 Exhibiting no polymorphism,
 Possessing motility,
 Forming spherical spores at an intracellular end and swelled sporangia, and
 Gram stain, positive;

<B. Cultural Property>
 (1) Characteristics of colonies formed when incubated at 27° C. in nutrient broth agar plate;
  Shape: Circular colony having a diameter of 1–2 mm after two days incubation
  Rim: Entire
  Projection: Hemispherical shape
  Gloss: Dull
  Surface: Smooth
  Color: Opaque and pale yellow
 (2) Characteristics of colony formed when incubated at 27° C. in nutrient broth agar plate;
  Growth: Roughly medium
  Shape: Radiative
 (3) Characteristics of colony formed when stab cultured at 27° C. in nutrient broth agar plate; Liquefying the agar plate.

<C. Physiological Properties>
 (1) VP-test: Negative
 (2) Indole formation: Negative
 (3) Gas formation from nitric acid: Positive
 (4) Hydrolysis of starch: Positive
 (5) Formation of pigment: Forming no soluble pigment
 (6) Urease: Positive
 (7) Oxidase: Positive
 (8) Catalase: Positive
 (9) Growth conditions: Growing at a pH of 5.5–9.0 and a temperature of 10–35° C.
 (10) Oxygen requirements: Aerobic
 (11) Utilization of carbon source and acid formation

| Carbon source | Utilization | Acid formation |
|---|---|---|
| D-Glucose | + | + |
| Glycerol | + | + |
| Sucrose | + | + |
| Lactose | + | + |

Note:
The symbol "+" means yes or positive.

(12) Mol % guanine (G) plus cytosine (C) of DNA: 40%

These bacteriological properties were compared with those of known microorganisms with reference to *Bergey's Manual of Systematic Bacteriology,* Vol. 2 (1986). As a result, it was revealed that the microorganism was identified with a novel microorganism of the species *Bacillus globisporus* and had a feature, not disclosed in any literature, of forming the α-isomaltosyl-transferring enzyme of the present invention which forms cyclotetrasaccharide by transferring α-isomaltosyl residue from α-isomaltosylglucosaccharide.

Based on these results, the present inventors named this microorganism "*Bacillus globisporus* C9", and deposited it on Apr. 25, 2000, in International Patent Organism Depositary, National Institute of Advanced Industrial Science and Technology (Previous name: National Institute of Bioscience and Human-Technology Agency of Industrial Science and Technology), Tsukuba Central 6, 1-1, Higashi 1-Chome Tsukuba-shi, Ibaraki-ken, 305-8566, Japan. The deposition of the microorganism was accepted on the same day by the institute under the accession number of FERM BP-7143.

<Strain C11>

<A. Morphology>
 Characteristics of cells when incubated at 27° C. in nutrient broth agar
 Existing usually in a rod shape of 0.5–1.0 μm×1.5–5 μm,
 Exhibiting no polymorphism,
 Possessing motility,
 Forming spherical spores at an intracellular end and swelled sporangia, and
 Gram stain, positive;

<B. Cultural Property>
 (1) Characteristics of colonies formed when incubated at 27° C. in nutrient broth agar plate;
  Shape: Circular colony having a diameter of 1–2 mm after two days incubation
  Rim: Entire
  Projection: Hemispherical shape
  Gloss: Dull
  Surface: Smooth
  Color: Opaque and pale yellow
 (2) Characteristics of colony formed when incubated at 27° C. in nutrient broth agar plate;
  Growth: Roughly medium
  Shape: Radiative
 (3) Characteristics of colony formed when stab cultured at 27° C. in nutrient broth gelatin plate;
  Liquefying the gelatin plate <C. Physiological Properties>
 (1) VP-test: Negative
 (2) Indole formation: Negative
 (3) Gas formation from nitric acid: Positive
 (4) Hydrolysis of starch: Positive (5) Formation of pigment: Forming no soluble pigment
(6) Urease: Positive
(7) Oxidase Positive
(8) Catalase: Positive
(9) Growth conditions: Growing at a pH of 5.5–9.0 and a temperature of 10–35° C.
(10) Oxygen requirements: Aerobic
(11) Utilization of carbon source and acid formation

| Carbon source | Utilization | Acid formation |
|---|---|---|
| D-Glucose | + | + |
| Glycerol | + | + |
| Sucrose | + | + |
| Lactose | + | + |

Note:
The symbol "+" means yes or positive.

(12) Mol % guanine (G) plus cytosine (C) of DNA: 39%

These bacteriological properties were compared with those of known microorganisms with reference to *Bergey's Manual of Systematic Bacteriology*, Vol. 2 (1986). As a result, it was revealed that the microorganism was identified with a novel microorganism of the species *Bacillus globisporus* and had a feature, not disclosed in any literature, of forming the α-isomaltosyl-transferring enzyme of the present invention which forms cyclotetrasaccharide by transferring α-isomaltosyl residue from α-isomaltosylglucosaccharide.

Based on these results, the present inventors named this microorganism "*Bacillus globisporus* C11", and deposited it on Apr. 25, 2000, in International Patent Organism Depositary National Institute of Advanced Industrial Science and Technology (Previous name: National Institute of Bioscience and Human-Technology Agency of Industrial Science and Technology), Tsukuba Central 6, 1-1, Higashi 1-Chome Tsukuba-shi, Ibaraki-ken, 305-8566, Japan. The deposition of the microorganism was accepted on the same day by the institute under the accession number of FERM BP-7144.

<Strain N75>

<A. Morphology>

Characteristics of cells when incubated at 27° C. in nutrient broth agar

Existing usually in a rod form of 0.5–1.0 μm×1.5–5 μm,

Exhibiting no polymorphism,

Possessing motility,

Forming spherical spores at an intracellular end and swelled sporangia, and

Gram stain, positive;

<B. Cultural Property>

(1) Characteristics of colonies formed when incubated at 27° C. in nutrient broth agar plate;

Shape: Circular colony having a diameter of 1–2 mm after two days incubation

Rim: Entire

Projection: Hemispherical shape

Gloss: Dull

Surface: Smooth

Color: Opaque and pale yellow (2) Characteristics of colony formed when incubated at 27° C. in nutrient broth agar plate;

Growth: Roughly medium

Shape: Radiative (3) Characteristics of colony formed when stab cultured at 27° C. in nutrient broth gelatin plate;

Liquefying the gelatin plate

<C. Physiological Properties>

(1) VP-test: Negative
(2) Indole formation: Negative
(3) Gas formation from nitric acid: Positive
(4) Hydrolysis of starch: Positive
(5) Formation of pigment: Forming no soluble pigment
(6) Urease: Positive
(7) Oxidase: Positive
(8) Catalase: Positive
(9) Growth conditions: Growing at a pH of 5.7–9.0 and a temperature of 10–35° C.
(10) Oxygen requirements: Aerobic
(11) Utilization of carbon source and acid formation

| Carbon source | Utilization | Acid formation |
|---|---|---|
| D-Glucose | + | + |
| Glycerol | + | + |
| Sucrose | + | + |
| Lactose | + | + |

Note:
The symbol "+" means yes or positive.

(12) Mol % guanine (G) plus cytosine (C) of DNA: 40%

These bacteriological properties were compared with those of known microorganisms with reference to *Bergey's Manual of Systematic Bacteriology*, Vol. 2 (1986). As a result, it was revealed that the microorganism was identified with a microorganism of the species *Bacillus globisporus* and had a feature, not disclosed in any literature, of forming the α-isomaltosyl-transferring enzyme of the present invention which forms cyclotetrasaccharide by transferring α-isomaltosyl residue from α-isomaltosylglucosaccharide.

Based on these results, the present inventors named this microorganism "*Bacillus globisporus* N75", and deposited it on May 16, 2001, in International Patent Organism Depositary National Institute of Advanced Industrial Science and Technology Tsukuba Central 6, 1-1, Higashi 1-Chome Tsukuba-shi, Ibaraki-ken, 305-8566, Japan. The deposition of the microorganism was accepted on the same day by the institute under the accession number of FERM BP-7591.

<Strain S1>

<A. Morphology>

Characteristics of cells when incubated at 27° C. in nutrient broth agar;

Existing usually in a rod form of 0.3–0.7 μm×0.8–3.5 μm,

Exhibiting polymorphism

Possessing no motility

Forming no spore

Gram stain: Positive (2) Characteristics of cells when incubated at 27° C. in EYG agar plate;

Exhibiting a growth cycle of *bacillus* and *cocci*

<B. Cultural Property>

(1) Characteristics of colonies formed when incubated at 27° C. in nutrient broth agar plate;

Shape: Circular colony having a diameter of 2–3 mm after one day incubation

Rim: Entire

Projection: Hemispherical shape

Gloss: Dull

Surface: Smooth
Color: Opaque and pale yellow
(2) Characteristics of colony formed when incubated at 27° C. in nutrient broth agar plate;
Growth: Roughly medium
Shape: Filamentous
(3) Characteristics of colony formed when stab cultured at 27° C. in nutrient broth gelatin plate;
Not liquefying the gelatin plate.

<C. Physiological Properties>
(1) Hydrolysis of starch: Negative
(2) Formation of pigment: Forming no soluble pigment
(3) Urease: Positive
(4) Oxidase: Positive
(5) Catalase: Positive
(6) Oxygen requirements: Aerobic
(7) Main diamino acid of cell wall: Lysine
(8) Peptidoglycan type of cell wall: Lysine-alanine
(9) N-acyl type of cell wall: Acetyl
(10) Sugar component of cell wall: Galactose, glucose, rhamnose, and mannose
(11) Vitamin requirements: Negative
(12) Mol % guanine (G) plus cytosine (C) of DNA: 65%
(13) DNA-DNA homology: Having 84.4% of DNA-DNA homology when compared with *Arthrobacter ramosus*, ATCC 13727.

These bacteriological properties were compared with those of known microorganisms with reference to *Bergey's Manual of Systematic Bacteriology*, Vol. 2 (1986). As a result, it was revealed that the microorganism was identified with a novel microorganism of the species *Arthrobacter ramosus* and had a feature, not disclosed in any literature, of forming the α-isomaltosyl-transferring enzyme of the present invention which forms cyclotetrasaccharide by transferring α-isomaltosyl residue from α-isomaltosylglucosaccharide.

Based on these results, the present inventors named this microorganism "*Arthrobacter ramosus* S1", and deposited it on May 16, 2001, in International Patent Organism Depositary National Institute of Advanced Industrial Science and Technology Tsukuba Central 6, 1-1, Higashi 1-Chome Tsukuba-shi, Ibaraki-ken, 305-8566, Japan. The deposition of the microorganism was accepted on the same day by the institute under the accession number of FERM BP-7592.

<Strain A19>

<A. Morphology>
(1) Characteristics of cells when incubated at 27° C. in nutrient broth agar;
Existing usually in a rod form of 0.4–0.8 μm×1.0–4.0 μm,
Exhibiting polymorphism,
Possessing no motility,
Forming no spore, and
Gram stain, positive;
(2) Characteristics of cells when incubated at 27° C. in EYG agar plate;
Exhibiting a growth cycle of *bacillus* and *cocci*

<B. Cultural Property>
(1) Characteristics of colonies formed when incubated at 27° C. in nutrient broth agar plate;
Shape Circular colony having a diameter of 2–3 mm after one day incubation
Rim: Entire
Projection: Hemispherical shape
Gloss: Dull Surface: Smooth
Color: Opaque and pale yellow
(2) Characteristics of colony formed when incubated at 27° C. in nutrient broth agar plate;
Growth: Roughly medium
Shape: Filamentous
(3) Characteristics of colony formed when stab cultured at 27° C. in nutrient broth gelatin plate;
Not liquefying the gelatin plate.

<C. Physiological Properties>
(1) Hydrolysis of starch: Negative
(2) Formation of pigment: Forming no soluble pigment
(3) Urease: Positive
(4) Oxidase: Positive
(5) Catalase: Positive
(6) Oxygen requirements: Aerobic
(7) Main diamino acid of cell wall: Lysine
(8) Peptidoglycan type of cell wall: Lysine-alanine
(9) N-acyl type of cell wall: Acetyl
(10) Sugar component of cell wall: Galactose, glucose, rhamnose, and mannose
(11) Vitamin requirements: Negative
(12) Mol % guanine (G) plus cytosine (C) of DNA: 62%
(13) DNA-DNA homology: Having a 66.5% of DNA-DNA homology when compared with *Arthrobacter globiformis*, ATCC 8010.

These bacteriological properties were compared with those of known microorganisms with reference to *Bergey's Manual of Systematic Bacteriology*, Vol. 2 (1986). As a result, it was revealed that the microorganism was identified with a microorganism of the species *Bacillus globisporus* and had a feature, not disclosed in any literature, of forming the α-isomaltosyl-transferring enzyme of the present invention which forms cyclotetrasaccharide by transferring α-isomaltosyl residue from α-isomaltosylglucosaccharide.

Based on these results, the present inventors named this microorganism "*Arthrobacter globiformis* A19", and deposited it on May 16, 2001, in International Patent Organism Depositary National Institute of Advanced Industrial Science and Technology Tsukuba Central 6, 1-1, Higashi 1-Chome Tsukuba-shi, Ibaraki-ken, 305-8566, Japan. The deposition of the microorganism was accepted on the same day by the institute under the accession number of FERM BP-7590.

The microorganisms usable in the present invention include any microorganisms of the above-identified genera *Bacillus* and *Arthrobacter*, and mutants thereof, as well as other microorganisms, capable of forming the α-isomaltosyl-transferring enzyme according to the present invention, and mutants thereof.

Any nutrient culture media can be used in the present invention as long as the above-mentioned microorganisms can grow therein and produce the α-isomaltosyl-transferring enzyme: For example, any synthetic- and natural-nutrient culture media can be arbitrarily used. The carbon sources usable in the present invention are those which the microorganisms assimilate for growing: Examples such are starches and phytoglycogen from plants; glycogen and pullulan from animals and microorganisms, and partial hydrolyzates thereof; saccharides such as D-glucose, D-fructose, lactose, sucrose, mannitol, L-sorbitol, and molasses; and organic acids such as citric acid and succinic acid. The concentrations of these carbon sources in nutrient culture media can be appropriately changed depending on the kinds of the carbon sources used. The nitrogen sources usable in the present invention are, for example, inorganic nitrogen compounds such as ammonium salts and nitrates; and organic nitrogen-containing substances such as urea, corn steep liquor, casein, peptone, yeast extract, and beef extract. The inorganic ingredients usable in the present invention are, for example, calcium salts, magnesium salts, potassium salts, sodium salts, phosphates, and other salts of manganese, zinc, iron, copper, molybdenum, and cobalt. If necessary, amino acids and vitamins can be appropriately used in combination.

The microorganisms used in the present invention are cultured under aerobic conditions at temperatures, usually, in the range of 4–40° C., preferably, 20–37° C.; and at pHs of 4–10, preferably, pHs of 5–9. The cultivation time used in the present invention is set to a time required for growing the microorganisms, preferably, 10–150 hours. The concentration of dissolved oxygen (DO) in nutrient culture media is not specifically restricted, but usually it is in the range of 0.5–20 ppm and can be kept within the range by appropriately employing means such as of controlling the level of aeration, stirring, aerating with or supplementarily with oxygen, and increasing the inner pressure of fermentors. The cultivation is freely carried out batchwise or in a continuous manner.

Since the activity of the enzyme of the present invention is detected intracellularly and throughout the resulting cultures, the cultures can be used intact as crude enzyme solutions or used after disrupting or removing the cells into suspensions or supernatants as crude enzyme solutions. Conventional liquid-solid separation methods can be applied to removing cells from the cultures; methods to centrifuge the cultures or filtrate the cultures with precoat filters, plane filters, or follow fibers can be appropriately used. As described above, cell-free cultures obtained after removing cells can be used as crude enzyme solutions, however, they may be concentrated by salting out using ammonium sulfate, sedimentation using acetone and alcohol, concentration in vacuo, and concentration with plane membranes or hollow fibers, prior to use.

Both the α-isomaltosyl-transferring enzyme of the present invention, contained in the above-mentioned crude and concentrated enzyme solutions, and the later described purified α-isomaltosyl-transferring enzyme can be used after immobilization by conventional methods. The immobilization methods are, for example, conjugation methods for conjugating onto ion-exchangers, covalent bonding/adsorption methods with resins and membranes, and inclusion methods using high-molecular weight substances can be appropriately employed.

The α-isomaltosyl-transferring enzyme of the present invention can be separated/purified by combining appropriately by conventional methods for separating/purifying enzymes and proteins. As an example, an electrophoretically homogenous α-isomaltosyl-transferring enzyme of the present invention can be obtained by successively salting out to concentrate the enzyme in the aforesaid crude enzyme solutions or concentrated enzyme solutions, dialyzing the resulting concentrates, subjecting the dialyzed solutions to sequential chromatographies of anion-exchange column chromatography using a resin of "SEPABEADS FP-DA13", affinity chromatography using a gel of "SEPHACRYL HR S-200", hydrophobic chromatography using a gel of "BUTYL-TOYOPEARL 650M", and affinity chromatography using a gel of "SEPHACRYL HR S-200".

The α-isomaltosyl-transferring enzyme of the present invention thus obtained is an enzyme that forms cyclotetrasaccharide from α-isomaltosylglucosaccharide by catalyzing a reaction including an α-isomaltosyl transfer reaction and that has the following physicochemical properties:

(1) Action

Forming a cyclotetrasaccharide having the structure of cyclo{→6)-α-D-glucopyranosyl-(1→3)-α-D-glucopyranosyl-(1→6)-α-D-glucopyranosyl-(1→3)-α-D-glucopyranosyl-(1→} from a saccharide having a glucose polymerization degree of at least three and having both the α-1,6 glucosidic linkage as a linkage at the non-reducing end and the α-1,4 glucosidic linkage other than the linkage at the non-reducing end;

(2) Molecular Weight

Having a molecular weight of about 82,000 to about 136,000 daltons when determined on sodium dodecyl sulfate polyacrylamide gel electrophoresis (SDS-PAGE);

(3) Isoelectric Point (pI)

Having a pI of about 3.7 to about 8.3 when determined on isoelectrophoresis using ampholine;

(4) Optimum Temperature

Having an optimum temperature of about 45° C. to about 50° C. when reacted at a pH of 6.0 for 30 min;

(5) Optimum pH

Having an optimum pH of about 5.5 to about 6.5 when reacted at 35° C. for 30 min;

(6) Thermal Stability

Having a thermostable range at temperatures of about 45° C. or lower when reacted at a pH of 6.0 for 60 min;

(7) pH Stability

Having a stable pH range at about 3.6 to about 10.0 when reacted at 4° C. for 24 hours; and (8) N-terminal Amino Acid Sequence Optionally having an amino acid sequence of isoleucine-aspartic acid-glycine-valine-tyrosine-histidine-alanine-proline (SEQ ID NO:1) or an amino acid sequence of aspartic acid-threonine-leucine-serine-glycine-valine-phenylalanine-histidine-glycine-proline (SEQ ID NO:8).

The substrates used arbitrarily for forming cyclotetrasaccharide via the action of the α-isomaltosyl-transferring enzyme include saccharides, which have a glucose polymerization degree of at least three and have both the α-1,6 glucosidic linkage as a linkage at their non-reducing ends and the α-1,4 glucosidic linkage other than the linkage, such as panose and isomaltosylmaltose. To prepare panose, for example, arbitrarily used are methods for hydrolyzing pullulan with acids, decomposing pullulan with neopullulanase or α-amylase form a microorganism of the genus *Thermoactinomyces,* subjecting maltose to the action of α-glucosidase, or subjecting a mixture of maltose and sucrose to the action of dextransucrase for transferring reaction. To prepare isomaltosylmaltose, for example, arbitrarily used are methods for hydrolyzing pullulan with β-amylase and pullulanase simultaneously, subjecting amylopectin or glycogen to the action of bacterial saccharifying α-amylase, or subjecting a mixture of maltotriose and sucrose to the action of dextransucrase.

In the case of contacting α-isomaltosyl-transferring enzyme with its substrates, the substrate concentration should not be specifically restricted. For example, even when a relatively low concentration solution, i.e., a 0.1% (w/v) substrate solution is used, the enzymatic reaction of α-isomaltosyl-transferring enzyme of the present invention proceeds to form cyclotetrasaccharide. On an industrial scale production of cyclotetrasaccharide, solutions with at least one percent (w/v), preferably, at least 10% (w/v) of substrate are suitable for forming cyclotetra-saccharide efficiently. The substrate solutions used in the present invention may be a relatively high concentration solution which even has incompletely dissolved, insoluble substrates. The reaction temperatures used in the present invention are those at which the enzymatic reaction proceeds, preferably, at around 60° C. or lower, more preferably, at around 30–50° C. The reaction pHs used in the present invention are usually set to pHs of 3.6–9, preferably, pHs of about 5.5 to about 7. The amount of enzyme used and the time for enzymatic reaction are closely related each other, they can be appropriately selected depending on the reaction rate of the desired enzymatic reaction.

The resulting solutions obtained by the above enzymatic reaction usually comprise cyclotetrasaccharide, as well as glucose, maltose and, as a remaining substrate, saccharides having a glucose polymerization degree of at least three and having both the α-1,6 glucosidic linkage as a linkage at the non-reducing end and the α-1,4 glucosidic linkage other than the above linkage, and thus they can be used intact as a cyclotetrasaccharide-containing solution. In necessary, these solutions can be sequentially subjected to the action of α-isomaltosyl-transferring enzyme and one or more enzymes selected from α-amylase, β-amylase, glucoamylase, and α-glucosidase to hydrolyze the concomitant oligosaccharides for obtaining cyclotetrasaccharide-containing solutions. In general, these solutions are purified before use. As the purification methods, conventional ones can be appropriately employed and one or more of the following methods can be arbitrarily used: Decoloration with activated charcoal, desalting by ion-exchange resins in a H- or OH- form, and column chromatographies such as ion-exchange column chromatography, column chromatography using activated charcoal, and silica gel column chromatography, separation using organic solvents such as alcohols and acetone, membrane separation using membranes with adequate separability, fermentation methods using microorganisms capable of assimilating or decomposing the concomitant saccharides but incapable of acting on cyclotetrasaccharide such as lactic acid bacteria, acetic acid bacteria, and yeasts; and hydrolysis and removal of the remaining saccharides by alkaline treatment.

Particularly, ion-exchange column chromatography is preferably used as an industrial scale production method for cyclotetrasaccharide; column chromatography using strong-acid cation exchange resins as disclosed, for example, in Japanese Patent Kokai Nos. 23,799/83 and 72,598/83. Using these column chromatographies, the concomitant saccharides other than cyclotetrasaccharide can be removed to advantageously produce cyclotetrasaccharide with an increased content or aqueous saccharide solutions comprising the saccharide. In the column chromatographies, any one of fixed-bed, moving bed, semi-moving bed methods, batchwise methods, semi-continuous methods, and continuous methods can be appropriately used.

The resulting aqueous solutions comprising cyclotetrasaccharide and those with an increased content of cyclotetrasaccharide are aqueous saccharide solutions containing at least 10% (w/w) (the term "% (w/w)" is abbreviated as "%", unless specified otherwise), preferably, at least 40% of cyclotetrasaccharide. Usually, the aqueous saccharide solutions are concentrated into syrupy products which are then optionally dried into powdery products.

To produce cyclotetrasaccharide crystals according to the present invention, usually, suitably used are aqueous saccharide solutions comprising cyclotetrasaccharide obtained by the above purification methods, preferably, those with a cyclotetrasaccharide content of at least about 40%, more preferably, at least 50%. In the case of preparing cyclotetrasaccharide crystal, tetra to hexa-hydrate, usually, the above aqueous saccharide solutions are made into supersaturated aqueous solutions, for example, into about 40–90% aqueous cyclotetrasaccharide solutions which are then placed in crystallizers, and then gradually cooled while stirring in the presence of about 0.1–20%, d.s.b., of a seed crystal to the cyclotetrasaccharide in the solutions at a temperature that keeps their supersaturated conditions, preferably, at a temperature of 10–90° C. to obtain massecuites. In the case of crystallizing cyclotetrasaccharide crystal, monohydrate, or anhydrous crystalline cyclotetrasaccharide, supersaturation conditions at a higher concentration and temperature are generally employed. While in the case of preparing crystalline cyclotetrasaccharide from massecuites or massecuites containing the crystal, for example, conventional methods such as separation, block pulverization, fluidized-bed granulation, and spray-drying methods can be arbitrarily used. Cyclotetra-saccharide crystal, monohydrate, and anhydrous crystalline cyclotetrasaccharide can also be prepared by dehydrating or drying cyclotetrasaccharide crystals, penta- to hexa-hydrate. Since the resulting cyclotetrasaccharide crystals and high cyclotetrasaccharide content powders according to the present invention are high-quality, mild and low sweet, non- or low-reducing white powers or solids and are acid tolerable, thermostable saccharides, they scarcely cause browning, smelling, and deterioration of materials used when mixed with other materials, particularly, amino acid-containing substances such as amino acids, oligopeptides, and proteins. Also they have lesser hygroscopicity and satisfactory adhesion/solidification preventing ability even in a powdery form.

Since the cyclotetrasaccharide of the present invention has inclusion ability, it effectively inhibits the dispersion, quality deterioration, and stabilization of easily volatile flavorful components and effective ingredients, and thus it can be preferably used as a flavor retainer or stabilizer. In this case, the stabilization ability of cyclotetrasaccharide can be improved by combining with other cyclic saccharides, for example, cyclodextrins, branched cyclodextrins, cyclic dextrans, and cyclic fructans.

Since cyclotetrasaccharide is not substantially hydrolyzed by amylase and α-glucosidase, it is substantially free of assimilation by living bodies when administered orally. Also, the saccharide is not substantially assimilated by intestinal microorganisms, and therefore it can be used as an extremely-low caloric water-soluble dietary fiber. In other words, when administered orally, the cyclotetrasaccharide of the present invention creates the sensation of fullness due to its weight and volume as a function of saccharide and is substantially free from assimilation, it can be also used suitably as a material for low-caloric foods and diet foods. In addition, it can be preferably used as a sweetener substantially free from causing dental caries because it is scarcely assimilated by dental caries-inducing microorganisms.

The cyclotetrasaccharide of the present invention is a non-poisonous, non-harmful natural sweetener with a satisfactory acid tolerance, alkaline tolerance, and heat tolerance, and because of these the saccharide in a crystalline form can be advantageously used for tablets and sugar-coated tablets in combination with one or more binders such as pullulan, hydroxyethyl starch, and polyvinylpyrrolidone. Furthermore, the cyclotetrasaccharide has properties of osmosis-controlling ability, filler-imparting ability, gloss-imparting ability, moisture-retaining ability, viscosity, syneresis-preventing ability, solidification-prevention ability, flavor-retaining ability, discoloration-preventing ability, stability, crystallization-preventing ability for other saccharides, insubstantial fermentability, retrogradation-preventing ability, protein-denaturation-preventing ability, lipid-denaturation-preventing ability, etc.

Thus, the cyclotetrasaccharide and the saccharide compositions comprising the same according to the present invention can be arbitrary used intact or optionally in an appropriate combination with other conventional materials in a variety of compositions such as food products, preferences including tobaccos and cigarettes, feeds, pet foods, cosmetics, and pharmaceuticals as a sweetener, substantially non-fermentable food material, substantially non-assimilable food material, low-dental-caries-inducing food material, low-caloric food material, taste-improving agent, flavor-improving agent, quality-improving agent, syneresis-preventing agent, solidification-preventing agent, flavor-retaining agent, discoloration-preventing agent, retrogradation-preventing agent, protein-denaturation-preventing agent, lipid-denaturation-preventing agent, stabilizer, excipient, inclusion agent, powdering base, etc. Examples of the above conventional materials include taste-improving agents, coloring agents, flavoring agents, strengthening agents, emulsifying agents, ultraviolet-preventing agents, and pharmaceutically effective ingredients, which are arbitrarily used in the present invention.

The cyclotetrasaccharide and the saccharide compositions comprising the same according to the present invention can be used intact as seasonings for sweetening, and if necessary, they can be used in combination with one or more other sweeteners, for example, powdered syrup, glucose, fructose, isomerized sugar, sucrose, maltose, α,α-trehalose, honey, maple sugar, meso-erythritol, xylitol, sorbitol, maltitol, dihydrochalcone, stevioside, α-glycosyl stevioside, sweetener of *Momordica grosvenori*, glycyrrhizin, thaumatin, L-aspartyl-L-phenylalanine methyl ester, saccharin, acesulfame K, sucralose, glycine, and alanine; and fillers such as dextrins, starches, and lactose. Particularly, the cyclotetrasaccharide and the saccharide compositions comprising the same can be suitably used as a low-caloric sweetener, diet sweetener, or the like in combination with one or more low-caloric sweeteners such as meso-erythritol, xylitol, and maltitol; and/or one or more sweeteners with a relatively-high sweetening power such as α-glycosyl stevioside, thaumatin, L-aspartyl-L-phenylalanine methyl ester, saccharin, acesulfame K, and sucralose.

The cyclotetrasaccharide and the saccharide compositions comprising the same in the form of a powder or crystal according to the present invention can be arbitrarily used intact or after mixing with fillers, excipients, binders, etc., and then formed into products with different shapes such as granules, spheres, short rods, plates, cubes, and tablets.

The cyclotetrasaccharide and the saccharide compositions comprising the same according to the present invention well harmonize with other tastable materials having sour-/acid-, salty-, delicious-, astringent-, and bitter-tastes; and have a satisfactorily high acid- and heat-tolerance. Thus, they can be favorably used in food products in general for sweetening, taste-improving, quality-improving, etc.

The cyclotetrasaccharide and the saccharide compositions comprising the same according to the present invention can be used in a soy sauce, powdered soy sauce, miso, "funmatsu-miso" (a powdered miso), "moromi" (a refined sake), "hishio" (a refined soy sauce), "furikake" (a seasoned fish meal), mayonnaise, dressing, vinegar, "sanbai-zu" (a sauce of sugar, soy sauce and vinegar), "funmatsu-sushi-su" (powdered vinegar for sushi), "chuka-no-moto" (an instant mix for Chinese dish), "tentsuyu" (a sauce for Japanese deep-fat fried food), "mentsuyu" (a sauce for Japanese vermicelli), sauce, catsup, "yakiniku-no-tare" (a sauce for Japanese grilled meat), curry roux, instant stew mix, instant soup mix, "dashi-no-moto" (an instant stock mix), mixed seasoning, "mirin" (a sweet sake), "shin-mirin" (a synthetic mirin), table sugar, and coffee sugar. Also, the cyclotetrasaccharide and the saccharide compositions comprising the same of the present invention can be arbitrarily used to sweeten, improve the taste and quality, improve the flavor and taste, or improve the quality of "wagashi" (Japanese cakes) such as "senbei" (a rice cracker), "arare" (a rice cake cube), "okoshi" (a millet-and-rice cake), "gyubi" (a starch paste), "mochi" (a rice paste) and the like, "manju" (a bun with a bean-jam), "uiro" (a sweet rice jelly), "an" (a bean jam) and the like, "yokan" (a sweet jelly of beans), "mizu-yokan" (a soft adzuki-bean jelly), "kingyoku" (a kind of yokan), jelly, pao de Castella, and "amedama" (a Japanese toffee); Western confectioneries such as a bun, biscuit, cracker, cookie, pie, pudding, butter cream, custard cream, cream puff, waffle, sponge cake, doughnut, chocolate, chewing gum, caramel, nougat, and candy; frozen desserts such as an ice cream and sherbet; syrups such as a "kajitsu-no-syrup-zuke" (a preserved fruit) and "korimitsu" (a sugar syrup for shaved ice); pastes such as a flour paste, peanut paste, and fruit paste; processed fruits and vegetables such as a jam, marmalade, "syrup-zuke" (fruit pickles), and "toka" (conserves); pickles and pickled products such as a "fukujin-zuke" (red colored radish pickles), "bettara-zuke" (a kind of whole fresh radish pickles), "senmai-zuke" (a kind of sliced fresh radish pickles), and "rakkyo-zuke" (pickled shallots); premixes for pickles and pickled products such as a "takuan-zuke-no-moto" (a premix for pickled radish), and "hakusai-zuke-no-moto" (a premix for fresh white rape pickles); meat products such as a ham and sausage; products of fish meat such as a fish ham, fish sausage, "kamaboko" (a steamed fish paste), "chikuwa" (a kind of fish paste), and "tenpura" (a Japanese deep-fat fried fish paste); "chinmi" (relish) such as a "uni-no-shiokara" (salted guts of sea urchin), "ika-no-shiokara" (salted guts of squid), "su-konbu" (processed tangle), losaki-surume" (dried squid strips), "fugu-no-mirin-boshi" (a dried mirin-seasoned swellfish), seasoned fish flour such as of Pacific cod, sea bream, shrimp, etc; "tsuku-dani" (foods boiled down in soy sauce) such as those of a laver, edible wild plant, dried squid, small fish, and shellfish; daily dishes such as a "nimame" (cooked beans), potato salad, and "konbu-maki" (a tangle roll); milk products; canned and bottled products such as those of a meat, fish meat, fruit, and vegetable; alcoholic beverages such as a synthetic sake, fermented liquor, sake, fruit wine, sparkling alcoholic beverage, and beer; soft drinks such as a coffee, cocoa, juice, carbonated beverage, sour milk beverage, and beverage containing a lactic acid bacterium; instant food products such as an instant pudding mix, instant hot cake mix, instant juice or soft drink, instant coffee, "sokuseki-shiruko" (an instant mix of adzuki-bean soup with rice cake), and instant soup mix; and other foods and beverages such as foods for babies, foods for therapy, health/tonic drinks, amino acid-containing beverages, peptide foods, and frozen foods.

The cyclotetrasaccharide and the saccharide compositions comprising the same according to the present invention can be arbitrarily used to improve the taste preference of feeds and pet foods for animals and pets such as domestic animals, poultry, honey bees, silk warms, and fishes; and also they can be arbitrary used as a sweetener, taste-improving agent, flavoring substance, quality-improving agent, and stabilizer in other products in a solid, powder, paste or liquid form such as a tobacco, cigarette, cosmetic, and pharmaceutical.

When used as a quality-improving agent or stabilizer, the cyclotetrasaccharide and the saccharide compositions comprising the same according to the present invention can be arbitrarily used in biologically active substances susceptible to lose their effective ingredients and activities, as well as in health foods and pharmaceuticals containing the biologically active substances. Examples of such biologically active substances are liquid preparations containing lymphokines such as α-, β- and γ-interferons, tumor necrosis factor-α (TNF-α), tumor necrosis factor-β (TNF-β), macrophage migration inhibitory factor, colony-stimulating factor, transfer factor, and interleukins; liquid preparations containing hormones such as insulin, growth hormone, prolactin, erythropoietin, and follicle-stimulating hormone; biological preparations such as BCG vaccine, Japanese encephalitis vaccine, measles vaccine, live polio vaccine, smallpox vaccine, tetanus toxoid, Trimeresurus antitoxin, and human immunoglobulin; liquid preparations containing antibiotics such as penicillin, erythromycin, chloramphenicol, tetracycline, streptomycin, and kanamycin sulfate; liquid preparations containing vitamins such as thiamine, riboflavin, L-ascorbic acid, cod liver oil, carotenoid, ergosterol, and tocopherol; highly unsaturated fatty acids and ester derivatives thereof such as EPA, DHA, and arachidonic acid; liquid preparations containing enzymes such as lipase, elastase, urokinase, protease, β-amylase, isoamylase, glucanase, and lactase; extracts such as a ginseng extract, snapping turtle extract, chlorella extract, aloe extract, extract of Sasa albo-marginata Makino et Shibata, peach leaf extract, loquat leaf extract, Chinese lemon peal extract, and propolis extract; pastes of viable microorganisms such as viruses, lactic acid bacteria, and yeasts; and royal jelly. By incorporating the cyclotetrasaccharide and the saccharide compositions comprising the same according to the present invention into the above biologically active substances, stable and high-quality health foods, cosmetics and pharmaceuticals in a liquid, paste, solid or powder form can be easily prepared.

As mentioned above, the following effects and features exerted by the cyclotetrasaccharide and the saccharide compositions comprising the same according to the present invention will be expected when used in combination with other ingredients generally used in external dermal application; the effects such as dispersion-prevention for flavor ingredients, deterioration prevention for active ingredients, moisture-retaining, syneresis prevention, crystallization prevention of other saccharides, deterioration prevention of proteins, deterioration prevention of lipids, stabilization of emulsion conditions. Similarly as other naturally occurring saccharides, since the cyclotetrasaccharide and the saccharide compositions comprising the same according to the present invention hardly stimulate the skin when applied thereupon and effectively retain the moisture in the skin, they can be advantageously incorporated into external dermal compositions for use. In the external dermal compositions, the cyclotetrasaccharide and the saccharide compositions comprising the same of the present invention can be usually used in an appropriate combination with one or more dermatologically applicable other ingredients of oils and fats, waxes, hydrocarbons, fatty acids, esters, alcohols, surfactants, dyes, flavors, hormones, vitamins, plant extracts, animal extracts, microbial extracts, salts, ultraviolet absorbents, photosensitizing dyes, antioxidants, antiseptics/bactericides, antiperspirants/deodorants, refreshments, chelating agents, saccharides, amino acids, and thickening agents. For example, in the field of cosmetics, the external dermal compositions can be provided in the form of a lotion, cream, milky lotion, gel, powder, paste, or block; for example, cleaning cosmetics such as soaps, cosmetic soaps, washing powders for the skin, face washing creams, facial rinses, body shampoos, body rinses, shampoos, and powders for washing hair; cosmetics for hair such as set lotions, hair blows, stick pomades, hair creams, pomades, hair sprays, hair liquids, hair tonics, hair lotions, hair restorers, hair dyes, treatments for the scalp, hair cosmetics, gloss-imparting hair oils, hair oils, and combing oils; base cosmetics such as cosmetic lotions, vanishing creams, emollient creams, emollient lotions, cosmetic packs in the form of a jelly peal off, jelly wiping, paste washing, or powders, cleansing creams, cold creams, hand creams, hand lotions, milky lotions, moisture-imparting liquids, after/before shaving lotions, after shaving creams, after shaving foams, before shaving creams, and baby oils; makeup cosmetics such as foundations in the form of a liquid, cream or solid, talcum powders, baby powders, body powders, perfume powders, makeup bases, powders in the form of a cream, paste, liquid, solid or powder, eye shadows, eye creams, mascaras, eyebrow pencils, eyelash makeups, rouges, rouge lotions; perfume cosmetics such as perfumes, paste/powder perfumes, eau de Colognes, perfume Colognes, and eau de toilette; suntan and suntan preventive cosmetics such as suntan creams, suntan lotions, suntan oils, sunburn preventing creams, sunburn preventing lotions; nail cosmetics such as manicures, pedicures, nail colors, nail lacquers, enamel removers, nail creams, and nail makeup cosmetics; eyeliner cosmetics; rouges and lipsticks such as lipsticks, lipcreams, paste rouges, and lip-glosses; oral cosmetics such as tooth pastes and mouth washes; and bath cosmetics such as bath salts/ oils, and bath cosmetic materials. In the field of pharmaceuticals, the external dermal compositions can be provided in the form of wet compresses, sprays, applications, bath agents, sticking agents, ointments, pastes, liniments, lotions, and cataplasms.

Concrete examples of other ingredients, which can be incorporated into external dermal compositions along with the cyclotetrasaccharide and the saccharide compositions comprising the same according to the present invention, are oils and fats including plant oils in the form of a liquid at ambient temperature such as an avocado oil, almond oil, olive oil, sesame oil, safflower oil, soy bean oil, camellia oil, persic oil, castor oil, and cotton seed oil; plant fats in the form of a solid at ambient temperature such as a cacao fat, coconut oil, palm oil, and Japanese wax; and animal oils such as mink oil, egg yolk oil, and turtle oil.

Examples of the waxes usable in the present invention are plant waxes such as a hohoba oil, carnauba wax, and candelilla wax; animal waxes such as a sperm oil, Baird's beaked while oil, beeswax, whale oil, and lanoline; and mineral oils such as a montan wax.

The carbohydrates usable in the present invention are, for example, mineral carbohydrates such as a paraffin or solid paraffin, liquid paraffin, ceresin, microcrystalline wax, and petrolatum; and animal hydrocarbons such as squalane and squalene.

Examples of the fatty acids usable in the present invention are lauric acid, myristic acid, palmitic acid, stearic acid, oleic acid, behenic acid, undecylenic acid, lanolin fatty acid, hard lanolin fatty acid, soft lanolin fatty acid, isostearic acid, and derivatives thereof.

The alcohols usable in the present invention are, for example, higher alcohols including polyalcohols such as lauryl alcohol, cetanol, setostearyl alcohol, stearyl alcohol, oleyl alcohol, behenyl alcohol, lanoline alcohol, hydrogenated lanoline alcohol, hexyldecanol, octyldodecanol, and polyethylene glycol; lower alcohols including polyalcohols such as ethanol, propanol, isopropanol, butanol, ethylene glycol, propylene glycol, and glycerine; and derivatives thereof.

Examples of the esters usable in the present invention are hexyl laurate, isopropyl myristate, myristyl myristate, cetyl myristate, octyl dodecyl myristate, isopropyl palmitate, butyl stearate, cholesteryl stearate, cholesteryl acetate, cholesteryl n-lactate, cholesteryl caproate, cholesteryl laurate, cholesteryl myristate, cholesteryl palmitate, cholesteryl stearate, cholesteryl 12-hydroxystearate, decyl oleate, octyldodecyl oleate, isopropyl lanoline fatty acid, glycerine trimyristate, propylene glycol dioleate, myristyl lactate, cetyl lactate, lanoline acetate, hexyldecyl dimethyloctanoate, and derivatives thereof.

The surfactants usable in the present invention are, for example, anion surfactants such as zinc laurate, zinc myristate, zinc palmitate, magnesium stearate, sodium lauryl sulfate, triethanolamine polyoxyethylene laurylether sulfate, sodium cetyl sulfate, polyoxyethylene laurylether sulfate, polyoxyethylene laurylether sulfate triethanolamine, polyoxyethylene cetylether phosphate, polyoxyethylene alkylphenylether phosphate, sodium N-lauroyl sarcosinate, coconut fatty acid sarcosinate triethanolamine, coconut fatty acid sodium methyltaurate, and soybean phospholipid; cation surfactants such as stearyltrimethylammonium chloride, distearyldimethylammonium chloride, benzalkonium chloride, cetylpyridinium chloride, alkylisoquinolinium bromide, and dodecyldimethyl 2-phenoxyethylammonium bromide; amphoteric ion surfactants such as sodium β-laurylaminopropionate, betaine lauryldimethylamino acetate, and 2-alkyl-N-carboxymethyl-N-hydroxyethyl imidazolinium betaine; non-ionic surfactants such as glyceryl monostearate self-emulsifying, glyceryl monostearate lipophilic, propylene glycol dioleate, sorbitan monolaurate, sorbitan monooleate, sucrose fatty acid ester, undecylenic acid monoethanolamide, coconut oil diethanolamide, polyethylene glycol monooleate, myristyl lactate, cetyl lactate, polyoxyethylene cetylether, polyoxyethylene octylphenylether, polyoxyethylene sorbitol monolaurate, polyoxyethylene sorbitan monolaurate, polyoxyethylene sorbitan monostearate, polyoxyethylene sorbitan trioleate, polyoxyethylene sorbitol tetraoleate, polyoxyethylene castor oil, and polyoxyethylene hydrogenated castor oil; and derivatives thereof.

Examples of the dyes usable in the present invention are red tar dyes such as amaranth, erythrosine, rose bengal, acid red, lake red C, lithol red, rhodamine, brilliant lake red, eosine YS, violamine R, brilliant fast scarlet, and Ponceau R; orange tar dyes such as dibromofluorescein, permanent orange, erythrosine yellow NA, and orange I; yellow tar dyes such as tartrazine, sunset yellow, uranin, benzidine yellow G, naphthol yellow S, and yellow AB; green tar dyes such as fast green FCF, alizarin cyanine green F, light green SF yellow, and naphthol green B; blue tar dyes such as brilliant blue FCF, indigo carmine, indigo, patent blue NA, carbanthrene blue, and sudan blue; brown tar dyes such as resorcin brown; purple tar dyes such as alizarin purple and alizurol purple; black tar dyes such as naphthol blue black; inorganic pigments such as zinc oxide, titanium oxide, cobalt hydroxide, aluminum hydroxide, talc, kaolin, mica, bentonite, manganese violet, and mica titanium; carotenoid pigments such as β-carotenoid, lycopene, and crocin; flavonoid pigments such as sisonine, saffrol yellow, rutin, and quercetin; flavin pigments such as riboflavin; quinone pigments such as cochineal, alizarin, and shikonin; and derivatives thereof.

The flavors used generally for external dermal uses can be roughly classified into natural plant and animal flavors, synthetic flavors, and mixtures thereof in an appropriate combination. Examples of the animal flavors include musk, civet, and castoreum and ambergris. The plant flavors are, for example, distillations, i.e., essential oils, obtainable by distillation, for example, with water vapor, anise seeds, basil leaves, caraway fruit, cinnamon barks, coriander seeds, lavender flowers, nutmeg seeds, peppermint leaves, rose flowers, rosemary flowers, seeds, and leaves, and thyme leaves, which are classified generally into those of solutes, resinoids, oleo resins, and tinctures depending on properties and processes. Examples of the synthetic flavors are acetophenone, anethole, benzyl alcohol, butyl acetate, camphor, citral, citronellol, cuminaldehyde, estragol, ethylvaniline, geranyl acetate, linarol, menthol, methyl p-cresol, methyl salicylate, phenyl acetate, vanillin, and derivatives thereof. In the present invention, flavor compositions mixed with the aforesaid flavors in an appropriate combination can be arbitrarily used.

The hormones usable in the present invention include, for example, follicle hormones such as estrone and estradiol; gestagens such as progesterone and pregnenolone; and adrenal cortex hormones such as cortisone, hydrocortisone, prednisone, and prednisolone. The vitamins usable in the present invention are, for example, vitamin A compounds such as retinol, retinoic acid, α-, β- and γ-carotenes, and derivatives thereof; vitamin B compounds such as thiamine (vitamin $B_1$), riboflavin (vitamin $B_2$), vitamin $B_6$ including pyridoxine, pyridoxal, and pyridoxamine, and derivatives thereof; vitamin C compounds such as L-ascorbic acid, glycosyl-L-ascorbic acids including 2-O-α-D-glucosyl-L-ascorbic acid, acyl derivatives (alias lipophilic vitamin C) of L-ascorbic acid and glycosyl-L-ascorbic acid, and other L-ascorbic acid derivatives such as L-ascorbic acid sulfate ester; vitamin D compounds such as ergocalciferol, cholecalciferol, and derivatives thereof; and vitamin E compounds such as α-, β-, γ- and δ-tocopherol, α-, β-, γ- and δ-tocotrienol, and derivatives thereof.

Examples of the plant extracts usable in the present invention are, in addition to the aforesaid plant extracts used as flavors, extracts such as those of chamomile, sage, aloe, scarlet sage, *Angelica keiskei,* avocado, nettle, fennel, oolong tea, cork tree bark, barley, *Abelmoschus esculentus,* allspice, seaweed, chinese quince, licorice, quince seed, gardenia, *Sasa albo-marginata,* cinnamon, black tea, rice bran, fermented rice bran, *Stevia rebaudiana,* celery, Japanese green gentian, soy bean, thyme, tea, common camellia, *Ligusticum acutilobum,* corn, carrot, *Rosa rugosa* (rugosa rose), hinoki (Japanese cypress), dishcloth gourd, safflower, pine, peach, eucalyptus, creeping saxifrage, yuzu (citron), lily, Job's tears, Mugwort, *Cyanophta* (blue-green algae), seaweed, apple, *Serratia marcescens,* and lettuce; and compounds isolated from plants such as hinokitiol, azulene, chlorophyll, and glycyrrhizin. The animal extracts usable in the present invention include placenta extracts. Examples of the extracts of microorganisms are yeast extracts. The salts usable in the external dermal composition of the present invention advantageously include those which can be used generally in conventional external dermal compositions, as well as sea water, deep sea water, dried ingredients of sea water, and natural salts, including those in the form of a liquid, such as mineral salts.

The ultraviolet absorbers usable in the present invention include, for example, p-aminobenzoic acid, p-dimethylaminobenzoic acid ethylhexylester, p-methoxycinnamic acid ethylhexylester, 2-(2-hydroxy-5-methylphenyl)benzotriazole, oxibenzozone, urocanic acid, ethyl urocanate, and derivatives thereof; organic substances capable of shielding ultraviolet rays such as 5-chlorouracil, guanine, and cytosine. Examples of the photosensitive dyes usable in the present invention are 2,2'[3'-[2-(3-heptyl-4-methyl-2-thiazolin-2-ylidene)ethyridene]propenylene]bis[3-heptyl-4-methyl thiazolinium iodide] alias "PLATONIN", 2-[2-(3-heptyl-4-methyl-2-thiazolin-2-ylidene)methine]-3-heptyl-4-methyl thiazolinium iodide alias "PIONIN", 6-[2-[(5-bromo-2-pyridyl)amino]vinyl]-1-ethyl-2-picolinium iodide alas "TAKANAL", 2-(2-anilino vinyl)-3,4-dimethyl-oxazolinium iodide alas "LUMINEX", and derivatives thereof.

In addition to the above compounds with anti-oxidation ability, the antioxidants usable in the present invention include, for example, propyl gallate, butyl gallate, octyl gallate, dodecyl gallate, nordihydroguaiaretic acid (NDGA), t-butylhydroxyanisole (BHA), butylated hydroxytoluene (BHT), 4-hydroxymethyl-1–2,6-di-t-butylphenol, and derivatives thereof.

In addition to the aforesaid compounds with aseptic or bactericide actions, examples of the aseptics and bactericides usable in the present invention include phenol compounds such as phenol, p-chloro metacresol, resorcin, p-oxy benzoate, and cresol; acid compounds including those in a salt form such as benzoic acid, sorbic acid, salicylic acid, and boric acid; bisphenol halides such as hexachlorophene, bithionol, and dichlorophene; amides such as 3,4,4'-trichlorocarvaniride, undecylenic acid monoethanolamide; quaternary ammonium compounds such as benzalkonium chloride, benzethonium chloride, and decalinium chloride; chlorhexidine hydrochloride, 1-hydroxypyridine-2-thione, lysozyme chloride; and derivatives thereof.

The antiperspirants/deodorants usable in the present invention are, for example, aluminum chloride, zinc chloride, chlorohydroxy aluminum, aluminum chlorohydroxy allantoinate, aluminum dihydroxy allantoinate, and aluminum chlorohydrate. Examples of the refreshments usable in the present invention include menthol, mint/peppermint oil, camphor, thymol, spirantol, and methyl salicylic acid. The chelating agents usable in the present invention are, for example, derivatives of ethylenediaminetetraacetic acid, tripolyphosphoric acid, hexamethacrylic acid, dihydroethylglycine, citric acid, tartaric acid, gluconic acid, and sugar acid.

The saccharides usable in the present invention are, for example, oligosaccharides such as sucrose, maltose, fructose, lactose, and trehalose; cyclic saccharides such as cyclodextrins other than cyclotetrasaccharide; sugar alcohols such as maltitol, sorbitol, mannitol, xylitol, and arabitol; polysaccharides such as hyaluronic acid, chondroitin sulfate, pullulan, cellulose, dextran, pectin, carrageenan, guar gum, corn syrup, gum arabic, tragacanth gum, and chitin; and their derivatives and partial hydrolyzates. Examples of the amino acids usable in the present invention are glycine, serine, threonine, tyrosine, cysteine, cystine, asparagine, glutamine, 2-pyrrolidone-5-carboxylicacid, hydroxyproline, pipecolicacid, sarcosine, homocysteine, homoserine, citrulline, aspartic acid, glutamic acid, cysteine sulfonic acid, argininosuccinic acid, arginine, lysine, histidine, ornithine, alanine, valine, leucine, isoleucine, methionine, phenylalanine, tryptophane, proline, β-alanine, taurine, β-aminobutyric acid, γ-aminobutyric acid, and salts thereof.

In addition to the aforesaid compounds having viscosity-imparting action, the thickening agents usable in the present invention include, for example, water-soluble high molecular substances such as quince seed, sodium alginate, cationated cellulose, hydroxyethyl cellulose, carboxymethyl cellulose, carboxymethyl starch, propylene glycol alginate, collagen, keratin, casein, albumin, gelatin, hydroxypropyl trimethylammonium chloride ether, polyvinyl alcohol, polyvinylpyrrolidone, sodium polyacrylate, polyvinylmethyl ether, and carboxyvinylpolymer; electrolytes such as sodium chloride, potassium chloride, and sodium sulfate; and oily materials.

The methods for incorporating into the aforesaid compositions the cyclotetrasaccharide or the saccharide compositions comprising the same according to the present invention are those which can incorporate them into a variety of compositions before completion of their processings, and which can be appropriately selected from the following conventional methods; mixing, kneading, dissolving, melting, soaking, penetrating, dispersing, applying, coating, spraying, injecting, crystallizing, and solidifying. The amount of the cyclotetrasaccharide or the saccharide compositions comprising the same to be preferably incorporated into the final compositions is usually at least 0.1%, desirably, at least 1%, d.s.b., to each composition.

The following experiments explain the present invention in detail:

Experiment 1

Preparation of Non-reducing Cyclotetrasaccharide by Culturing

A liquid medium consisting of 5% (w/v) of panose, produced by Hayashibara Biochemical Laboratories Inc., Okayama, Japan, 1.5% (w/v) of "ASAHIMEAST", a yeast extract commercialized by Asahi Breweries, Ltd., Tokyo, Japan, 0.1% (w/v) of dipotassium phosphate, 0.06% (w/v) of sodium phosphate dodecahydrate, 0.05% (w/v) magnesium sulfate heptahydrate, and water was placed in a 500-ml Erlenmeyer flask in an amount of 100 ml, sterilized by autoclaving at 121° C. for 20 min, cooled, and then seeded with *Bacillus globisporus* C9 strain, FERM BP-7143, followed by culturing under rotary-shaking conditions at 27° C. and 230 rpm for 48 hours and centrifuging the resulting culture to remove cells to obtain a supernatant. The supernatant was autoclaved at 120° C. for 15 min and then cooled, and the resulting insoluble substances were removed by centrifugation to obtain a supernatant.

To examine the saccharides in the supernatant, they were separated from the supernatant by silica gel thin-layer chromatography (abbreviated as "TLC" hereinafter) using, as a developer, a mixture solution of n-butanol, pyridine, and water (=6:4:1), and, as a thin-layer plate, "KIESELGEL 60", an aluminum plate (20×20 cm) for TLC commercialized by Merck & Co., Inc., Rahway, USA. The coloration of both the separated total sugars by the sulfuric acid-methanol method and the reducing saccharides by the diphenylamine-aniline method detected a non-reducing saccharide at a position with an Rf value of about 0.31, which was positive on the former detection method but negative on the latter detection method.

About 90 ml of the supernatant was adjusted to pH 5.0 and 45° C. and then incubated for 24 hours after admixed with 1,500 units/g solids of "TRANSGLUCOSIDASE L AMANO™", an α-glucosidase commercialized by Amano Pharmaceutical Co., Ltd., Aichi, Japan, and 75 units/g solids of a glucoamylase commercialized by Nagase Biochemicals, Ltd., Kyoto, Japan. Thereafter, the resulting culture was adjusted to pH 12 by the addition of sodium hydroxide and boiled for two hours to decompose the remaining reducing sugars such as panose. After removing insoluble substances by filtration, the resulting solution was decolored and desalted with "DIAION PK218" and "DIAION WA30", ion-exchange resins commercialized by Mitsubishi Chemical Industries, Ltd., Tokyo, Japan, and further desalted with "DIAION SK-1B", commercialized by Mitsubishi Chemical Industries, Ltd., Tokyo, Japan, and "AMBERLITE IRA411", an anion exchange resin commercialized by Japan Organo Co., Ltd., Tokyo, Japan, followed by filtering with a membrane, concentrated by an evaporator, and lyophilized in vacuo to obtain about 0.5 g, d.s.b., of a saccharide powder.

The analysis of the saccharide on high-performance liquid chromatography (abbreviated as "HPLC" hereinafter) detected a single peak with an elution time of 10.84 min as shown in FIG. 1, and revealed that the saccharide had a purity of 99.9% or higher. HPLC was carried out using "SHODEX KS-801 column", commercialized by Showa Denko K.K., Tokyo, Japan, at an inner column temperature of 60° C. and a flow rate of 0.5 ml/min of water, and using "RI-8012", a differential refractometer, commercialized by Tosoh Corporation, Tokyo, Japan.

When measured for reducing power of the saccharide on the Somogyi-Nelson's method, the reducing power was below a detectable level, revealing that the specimen consisted essentially of a non-reducing saccharide.

Experiment 2

Structural Analysis of Non-reducing Saccharide

Fast atom bombardment mass spectrometry (called "FAB-MS") of a non-reducing saccharide, obtained by the method in Experiment 1, clearly detected a proton-addition-molecular ion with a mass number of 649, meaning that the saccharide had a mass number of 648.

According to conventional manner, the saccharide was hydrolyzed with sulfuric acid and then analyzed for sugar composition. As a result, only D-glucose molecules were detected, revealing that the saccharide was composed of D-glucose molecules for forming a cyclic tetrasaccharide composed of four D-glucose molecules in view of the above mass number.

Figure 2:
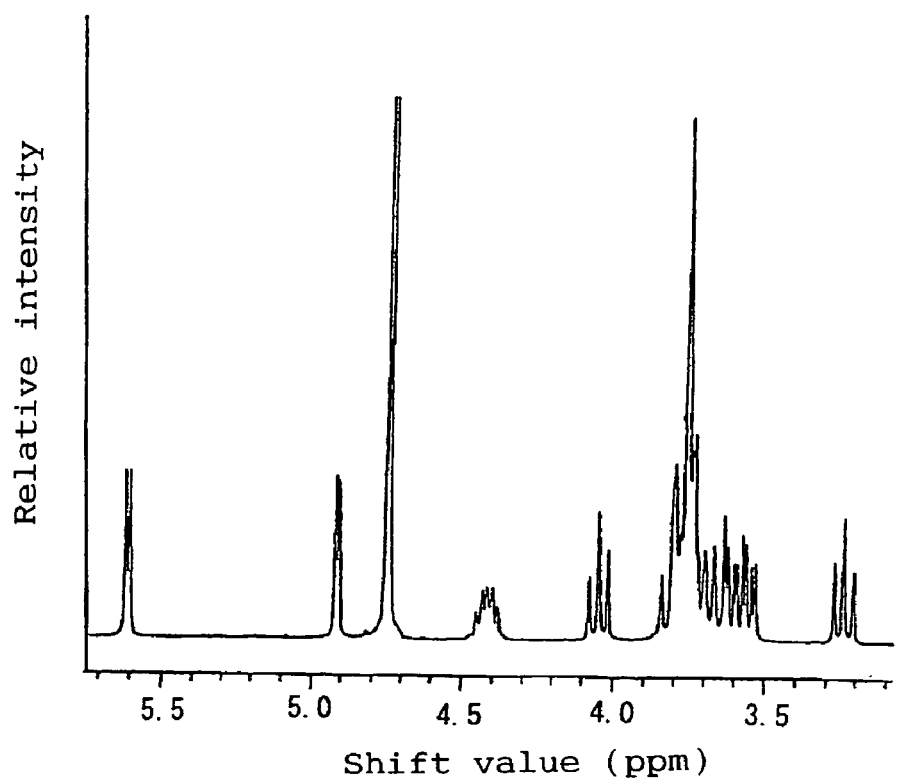
FIG. 2 is a nuclear resonance spectrum ($^1$H-NMR) of cyclotetrasaccharide obtained by the α-isomaltosyl-transferring enzymatic reaction according to the present invention.
Figure 3:
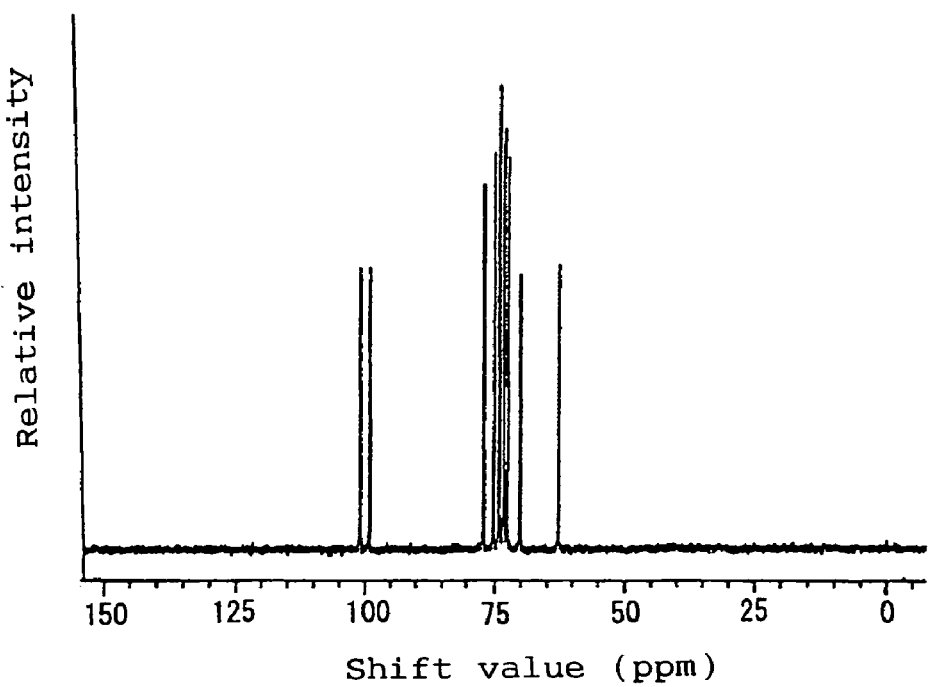
FIG. 3 is a nuclear resonance spectrum ($^{13}$C-NMR) of cyclotetrasaccharide obtained by the α-isomaltosyl-transferring enzymatic reaction according to the present invention, when determined on high-performance liquid chromatography.
Figure 4:
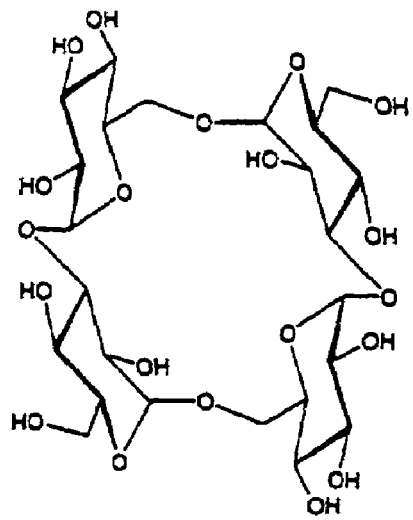
FIG. 4 is a figure of the structure of cyclotetrasaccharide, i.e., cyclo{→6)-α-D-glucopyranosyl-(1→3)-α-D-glucopyranosyl-(1→6)-α-D-glucopyranosyl-(1→3)-α-D-glucopyranosyl-(1→}.

Nuclear magnetic resonance analysis (abbreviated as "NMR" hereinafter) of the saccharide gave a $^1$H-NMR spectrum as shown in FIG. 2 and a $^{13}$C-NMR spectrum as shown in FIG. 3, and these spectra were compared with those of known saccharides, revealing that the spectra of the saccharide were coincided with those of a non-reducing cyclic saccharide, i.e., cyclo{→6)-α-D-glucopyranosyl-(1→3)-α-D-glucopyranosyl-(1→6)-α-D-glucopyranosyl-(1→3)-α-D-glucopyranosyl-(1→} as disclosed in "*European Journal of Biochemistry*", pp. 641–648 (1994). The data confirmed that the saccharide was a cyclotetrasaccharide as shown in FIG. 4, i.e., cyclo{→6)-α-D-glucopyranosyl-(1→3)-α-D-glucopyranosyl-(1→6)-α-D-glucopyranosyl-(1→3)-α-D-glucopyranosyl-(1→}.

Experiment 3

Production of α-isomaltosyl-transferring Enzyme from *Bacillus globisporus* C9

A liquid culture medium consisting of 4.0% (w/v) of "PINE-DEX #4", a partial starch hydrolysate commercialized by Matsutani Chemical Ind., Tokyo, Japan, 1.8% (w/v) of "ASAHIMEAST", a yeast extract commercialized by Asahi Breweries, Ltd., Tokyo, Japan, 0.1% (w/v) of dipotassium phosphate, 0.06% (w/v) of sodium phosphate dodecahydrate, 0.05% (w/v) magnesium sulfate heptahydrate, and water was placed in 500-ml Erlenmeyer flasks in respective volumes of 100 ml, sterilized by autoclaving at 121° C. for 20 min, cooled, and then seeded with *Bacillus globisporus* C9 strain, FERM BP-7143, followed by culturing under rotary-shaking conditions at 27° C. and 230 rpm for 48 hours for a seed culture.

About 20 L of a fresh preparation of the same liquid culture medium as used in the above seed culture were placed in a 30-L fermentor, sterilized by heating, and then cooled to 27° C. and inoculated with one percent (v/v) of the seed culture, followed by culturing at 27° C. and pH 6.0–8.0 for 48 hours under aeration-agitation conditions. After completion of the culture, the resulting culture, which had about 1.5 units/ml (total enzymatic activity of about 26,900 units) of α-isomaltosyl-transferring enzyme of the present invention, was centrifuged at 10,000 rpm for 30 min to obtain about 18 L of a supernatant.

The activity of the enzyme was assayed by dissolving panose in 100 mM acetate buffer (pH 6.0) to give a concentration of two percent (w/v) for a substrate solution, adding a 0.5 ml of an enzyme solution to a 0.5 ml of the substrate solution, enzymatically reacting the mixture solution at 35° C. for 30 min, suspending the reaction mixture by boiling for 10 min, and quantifying glucose by the glucose oxidation method. One unit activity of the α-isomaltosyl-transferring enzyme is defined as the enzyme amount that forms one micromole of glucose per minute under the above enzymatic reaction conditions. Throughout the specification, the enzymatic activity of the α-isomaltosyl-transferring enzyme means the unit(s) assayed as above.

Experiment 4

Purification of α-isomaltosyl-transferring Enzyme from *Bacillus globisporus* C9

About 18 L of the supernatant in Experiment 3 was salted out with 80% saturated ammonium sulfate and allowed to stand at 4° C. for 24 hours, and the formed sediments were collected by centrifugation at 10,000 rpm for 30 min, dissolved in 10 mM phosphate buffer (pH 7.5), and dialyzed against a fresh preparation of the same buffer to obtain about 400 ml of a crude enzyme solution with 24,700 units of the present enzyme. The crude enzyme solution was subjected to ion-exchange chromatography using 1,000 ml of "SEPABEADS FP-DA13" gel, an ion-exchange resin commercialized by Mitsubishi Chemical Industries, Ltd., Tokyo, Japan. The enzyme was eluted as non-adsorbed fractions without adsorbing on the ion-exchange resin. The resulting enzyme solution was dialyzed against 10 mM phosphate buffer (pH 7.0) with 1 M ammonium sulfate, and the dialyzed solution was centrifuged to remove impurities. The supernatant was subjected to affinity chromatography using 500 ml of "SEPHACRYL HR S-200", a gel commercialized by Amersham Corp., Div. Amersham Biosciences K.K., Tokyo, Japan. The enzyme adsorbed on the gel and eluted with a linear gradient decreasing from 1 M to 0 M of ammonium sulfate, followed by the elution of the enzyme from the gel at a concentration of around 0 M and collecting fractions with the enzymatic activity. The fractions were pooled and dialyzed against 10 mM phosphate buffer (pH 7.0) containing 1 M ammonium sulfate, and the dialyzed solution was centrifuged to remove insoluble substances, followed by subjecting the resulting supernatant to hydrophobic column chromatography using 350 ml of "BUTYL-TOYOPEARL 650M", a gel commercialized by Tosoh Corporation, Tokyo, Japan. The enzyme of the present invention adsorbed on the above gel and eluted therefrom with a linear gradient decreasing from 1 M to 0 M of ammonium sulfate, followed by eluting the enzyme from the gel at a concentration of around 0.3 M and collecting fractions with the enzymatic activity. The fractions were pooled and dialyzed against 10 mM phosphate buffer (pH 7.0) containing 1 M ammonium sulfate, and the dialyzed solution was centrifuged to remove insoluble substances, followed by purifying the resulting supernatant on affinity column chromatography using "SEPHACRYL HR S-200" to obtain a purified α-isomaltosyl-transferring enzyme. The activity and the specific activity of α-isomaltosyl-transferring enzyme in each purification step are in Table 1.

TABLE 1

| Purification step | Enzyme* activity (unit) | Specific activity of enzyme* (unit/mg protein) | Yield (%) |
|---|---|---|---|
| Culture supernatant | 26,900 | 0.41 | 100 |
| Dialyzed solution after salting out with ammonium sulfate | 24,700 | 1.85 | 91.8 |
| Eluate from ion-exchange column chromatography | 19,400 | 3.41 | 72.1 |
| Eluate from affinity column chromatography | 13,400 | 18.6 | 49.8 |
| Eluate from hydrophobic column chromatography | 10,000 | 21.3 | 37.2 |
| Eluate from affinity column chromatography | 6,460 | 26.9 | 24.0 |

Note:
The symbol "*" means the α-isomaltosyl-transferring enzyme.

The purity of a purified specimen of α-isomaltosyl-transferring enzyme, obtained in this Experiment, was determined on SDS-PAGE using a 7.5% (w/v) of polyacrylamide gel and revealed to be a single protein band, i.e., a relatively high purity specimen.

Experiment 5

Property of α-isomaltosyl-transferring Enzyme

A purified specimen of α-isomaltosyl-transferring enzyme, obtained by the method in Experiment 4, was subjected to SDS-PAGE using a 7.5% (w/v) of sodium dodecyl sulfate polyacrylamide gel and then determined for molecular weight by comparing with the dynamics of standard molecular markers, commercialized by Bio-Rad Laboratories Inc., Brussels, Belgium, electrophoresed in parallel, revealing that the enzyme had a molecular weight of about 112,000±20,000 daltons.

A fresh preparation of the above purified specimen was subjected to isoelectrophoresis using a gel containing two percent (w/v) ampholine commercialized by Amersham Corp., Div. Amersham International, Arlington Heights, Ill., USA, and then measured for pHs of protein bands and gels to determine the isoelectric point of the enzyme, revealing that the enzyme had an isoelectric point of about 5.5±0.5.

Figure 5:
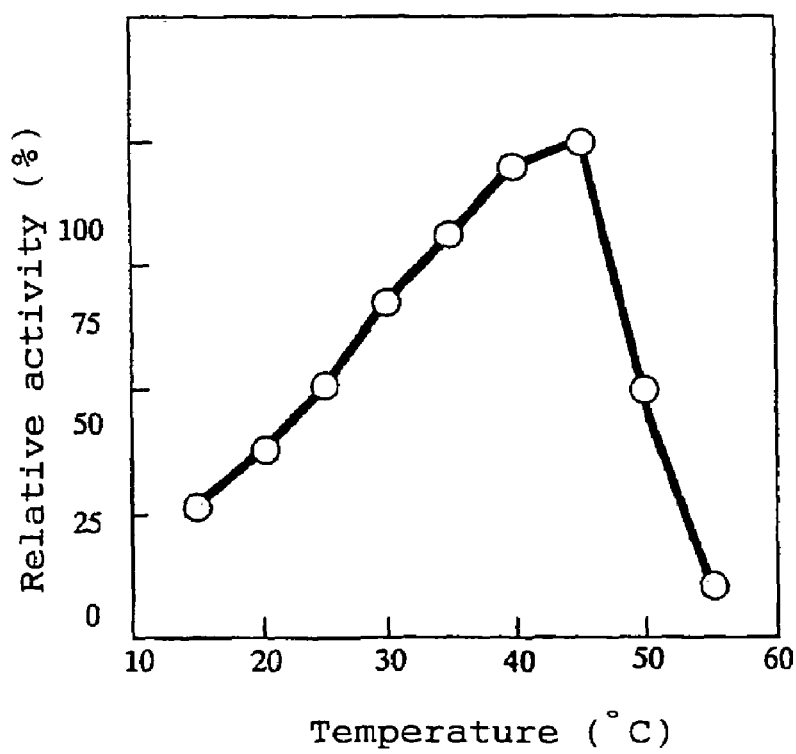
FIG. 5 shows the thermal influence on the enzymatic activity of α-isomaltosyl-transferring enzyme from a microorganism of the species *Bacillus globisporus* C9 strain.
Figure 6:
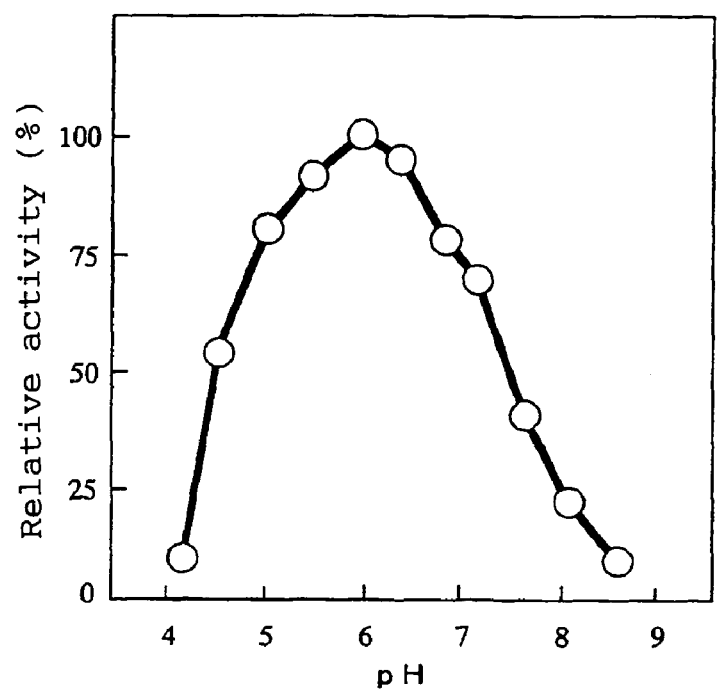
FIG. 6 shows the pH influence on the enzymatic activity of α-isomaltosyl-transferring enzyme from a microorganism of the species *Bacillus globisporus* C9 strain.
Figure 7:
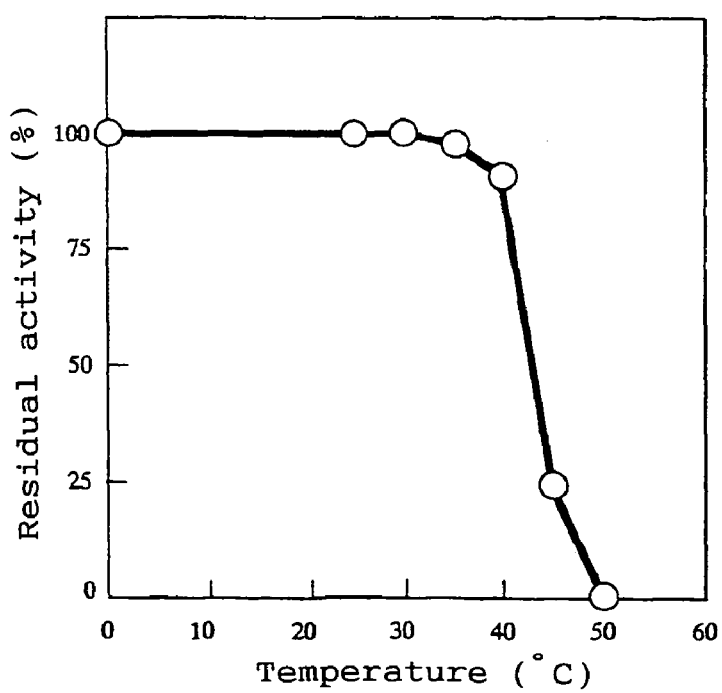
FIG. 7 shows the thermal stability of α-isomaltosyl-transferring enzyme from a microorganism of the species *Bacillus globisporus* C9 strain.
Figure 8:
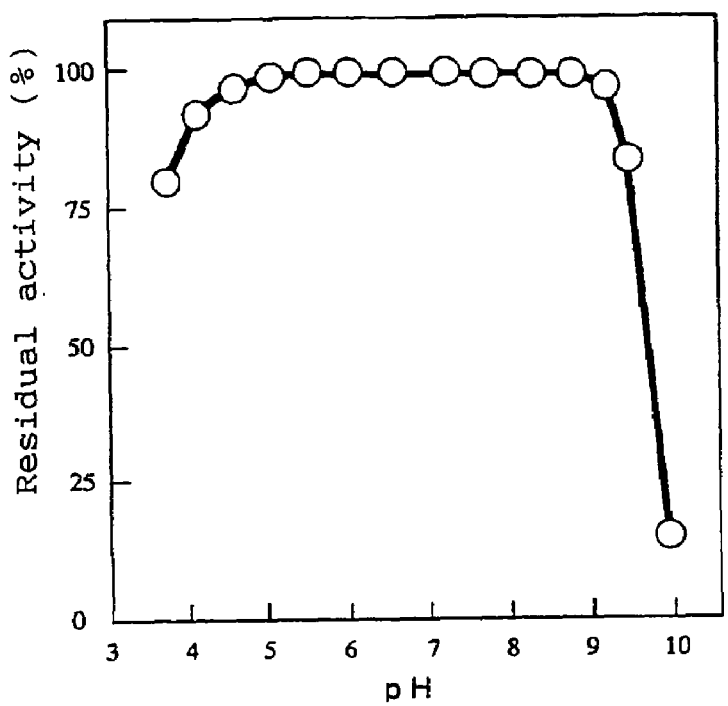
FIG. 8 shows the pH stability of α-isomaltosyl-transferring enzyme from a microorganism of the species *Bacillus globisporus* C9 strain.

The influence of temperature and pH on the activity of α-isomaltosyl-transferring enzyme was examined in accordance with the assay for the enzyme activity. The results are in FIG. 5 (influence of temperature) and FIG. 6 (influence of pH). The optimum temperature of the enzyme was about 45° C. when reacted at pH 6.0 for 30 min, and the optimum pH of the enzyme was about 6.0 when reacted at 35° C. for 30 min. The thermal stability of the enzyme was determined by incubating the testing enzyme solutions in 20 mM acetate buffer (pH 6.0) at prescribed temperatures for 60 min, cooling the resulting enzyme solutions with water, and assaying the remaining enzyme activity of each solution. The pH stability of the enzyme was determined by keeping the testing enzyme solutions in 50 mM buffers having different pHs at 4° C. for 24 hours, adjusting the pH of each solution to 6.0, and assaying the remaining enzyme activity of each solution. These results are respectively in FIG. 7 (thermal stability) and FIG. 8 (pH stability). As a result, the enzyme had thermal stability of up to about 40° C. and pH stability of about 4.0 to about 9.0.

The influence of metal ions on the activity of α-isomaltosyl-transferring enzyme was examined in the presence of 1 mM of each metal-ion according to the assay for the enzyme activity. The results are in Table 2.

TABLE 2

| Metal ion | Relative activity (%) | Metal ion | Relative activity (%) |
|---|---|---|---|
| None | 100 | $Hg^{2+}$ | 1 |
| $Zn^{2+}$ | 88 | $Ba^{2+}$ | 102 |
| $Mg^{2+}$ | 98 | $Sr^{2+}$ | 101 |
| $Ca^{2+}$ | 101 | $Pb^{2+}$ | 89 |
| $Co^{2+}$ | 103 | $Fe^{2+}$ | 96 |
| $Cu^{2+}$ | 57 | $Fe^{3+}$ | 105 |
| $Ni^{2+}$ | 102 | $Mn^{2+}$ | 106 |
| $Al^{3+}$ | 103 | EDTA | 104 |

As evident form the results in Table 2, the enzyme activity was greatly inhibited by $Hg^{2+}$ and was also inhibited by $Cu^{2+}$. It was also found that the enzyme was neither activated by $Ca^{2+}$ nor inhibited by EDTA.

Amino acid analysis of the N-terminal amino acid sequence of the enzyme by "PROTEIN SEQUENCER MODEL 473A", an apparatus of Applied Biosystems, Inc., Foster City, USA, revealed that the enzyme had a partial amino acid sequence of SEQ ID NO:9, i.e, isoleucine-aspartic acid-glycine-valine-tyrosine-histidine-alanine-proline-asparagine-glycine in the N-terminal region.

Experiment 6

Production of α-isomaltosyl-transferring Enzyme from *Bacillus globisporus* C11

A liquid nutrient culture medium, consisting of 4.0% (w/v) of "PINE-DEX #4", a partial starch hydrolysate, 1.8% (w/v) of "ASAHIMEAST", a yeast extract, 0.1% (w/v) of dipotassium phosphate, 0.06% (w/v) of sodium phosphate dodecahydrate, 0.05% (w/v) magnesium sulfate heptahydrate, and water was placed in 500-ml Erlenmeyer flasks in respective volumes of 100 ml, and the sequentially autoclaved at 121° C. for 20 minutes to effect sterilization, cooled, inoculated with a stock culture of *Bacillus globisporus* C11, FERM BP-7144, and incubated at 27° C. for 48 hours under rotary shaking conditions of 230 rpm. The resulting cultures were pooled for a seed culture.

About 20 L of a fresh preparation of the same nutrient culture medium as used in the above culture were placed in a 30-L fermentor, sterilized by heating, cooled to 27° C., inoculated with 1% (v/v) of the seed culture, and incubated for about 48 hours while stirring under aeration-agitation conditions at 27° C. and a pH of 6.0–8.0. The resultant culture, having about 1.8 units/ml of α-isomaltosyl-transferring enzyme activity, was centrifuged at 10,000 rpm for 30 min to obtain an about 18 L supernatant with about 1.7 units/ml of α-isomaltosyl-transferring enzyme activity in a total enzyme activity of about 30,400 units.

Experiment 7

Purification of α-Isomaltosyl-transferring Enzyme from *Bacillus globisporus* C11

An 18 L of the supernatant obtained in Experiment 6 was salted out with an 80% saturated ammonium sulfate solution and allowed to stand at 4° C. for 24 hours. Then the salted out sediments were collected by centrifugation at 10,000 for 30 min, dissolved in 10 mM phosphate buffer (pH 7.5), dialyzed against a fresh preparation of the same buffer to obtain about 416 ml of a crude enzyme solution with about 28,000 units of α-isomaltosyl-transferring enzyme. When subjected to ion-exchange column chromatography using 1,000 ml of "SEPABEADS FP-DA13", a gel commercialized by Mitsubishi Chemical Industries, Ltd., Tokyo, Japan. The enzyme did not adsorb on the gel and eluted therefrom as non-adsorbed fractions. The non-adsorbed fractions with the enzyme were pooled and dialyzed against 10 mM phosphate buffer (pH 7.0) containing 1 M ammonium sulfate, and the dialyzed solution was centrifuged to remove impurities. The resulting supernatant was fed to affinity column chromatography using 500 ml of "SEPHACRYL HR S-200" gel to purify the enzyme. The enzyme, adsorbed on the above gel, was eluted therefrom with a linear gradient decreasing from 1 M to 0 M of ammonium sulfate, followed by collecting fractions eluted at a concentration of about 0.3 M ammonium sulfate. The collected fractions were pooled and dialyzed against 10 mM phosphate buffer (pH 7.0) containing 1 M ammonium sulfate, and the dialyzed solution was centrifuged to remove insoluble substances, followed by subjecting the resulting supernatant to hydrophobic column chromatography using 350 ml of "BUTYL-TOYOPEARL 650M". The enzyme of the present invention adsorbed on the above gel and eluted therefrom with a linear gradient decreasing from 1 M to 0 M of ammonium sulfate, followed by eluting the enzyme from the gel at a concentration of around 0.3 M and collecting fractions with the enzymatic activity. The fractions were pooled and dialyzed against 10 mM phosphate buffer (pH 7.0) containing 1 M ammonium sulfate, and the dialyzed solution was centrifuged to remove insoluble substances, followed by purifying the resulting supernatant on affinity column chromatography using "SEPHACRYL HR S-200" to obtain a purified α-isomaltosyl-transferring enzyme. The amount of enzyme activity, specific activity, and yield of the α-isomaltosyl-transferring enzyme in each purification step are in Table 3.

TABLE 3

| Purification step | Enzyme* activity (unit) | Specific activity of enzyme* (unit/mg protein) | Yield (%) |
|---|---|---|---|
| Culture supernatant | 30,400 | 0.45 | 100 |
| Dialyzed solution after salting out with ammonium sulfate | 28,000 | 1.98 | 92.1 |
| Eluate from ion-exchange column chromatography | 21,800 | 3.56 | 71.7 |
| Eluate from affinity column chromatography | 13,700 | 21.9 | 45.1 |
| Eluate from hydrophobic column chromatography | 10,300 | 23.4 | 33.9 |
| Eluate from affinity column chromatography | 5,510 | 29.6 | 18.1 |

Note:
The symbol "*" means α-isomaltosyl-transferring enzyme.

The purified α-isomaltosyl-transferring enzyme specimen was assayed for purity on gel electrophoresis using a 7.5% (w/v) sodium dodecyl sulfate polyacrylamide gel and detected as a single protein band, i.e., a high purity enzyme specimen.

Experiment 8

Property of α-isomaltosyl-transferring Enzyme

A purified specimen of α-isomaltosyl-transferring enzyme, obtained by the method in Experiment 7, was subjected to SDS-PAGE using a 7.5% (w/v) of sodium dodecyl sulfate polyacrylamide gel and then determined for molecular weight by comparing with the dynamics of standard molecular markers, commercialized by Bio-Rad Laboratories Inc., Brussels, Belgium, electrophoresed in parallel, revealing that the enzyme had a molecular weight of about 102,000±20,000 daltons.

A fresh preparation of the above purified specimen was subjected to isoelectrophoresis using a gel containing 2% (w/v) ampholine commercialized by Amersham Corp., Div. Amersham International, Arlington Heights, Ill., USA, and then measured for pHs of protein bands and gels to determine the isoelectric point of the enzyme, revealing that the enzyme had an isoelectric point of about 5.6±0.5.

Figure 9:
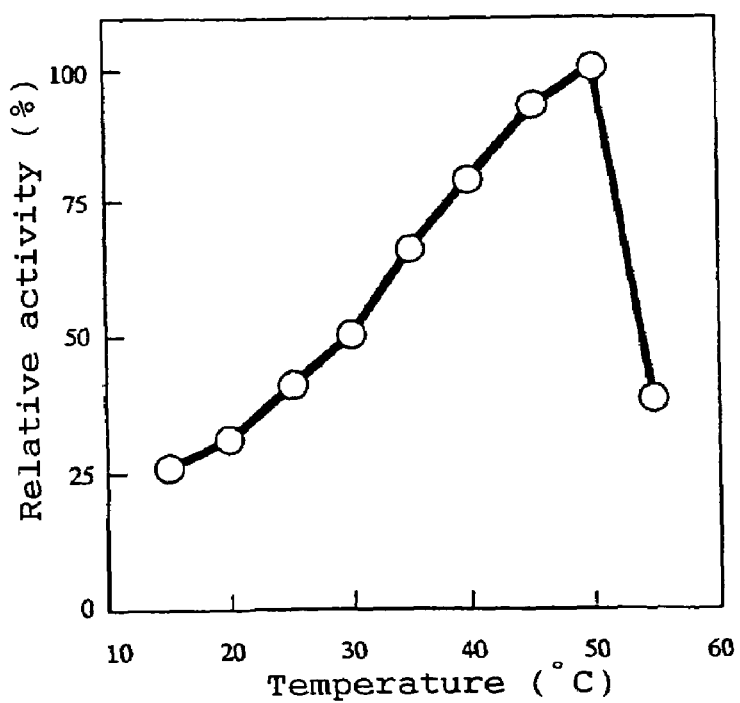
FIG. 9 shows the thermal influence on the enzymatic activity of α-isomaltosyl-forming enzyme from a microorganism of the species *Bacillus globisporus* C11 strain.
Figure 10:
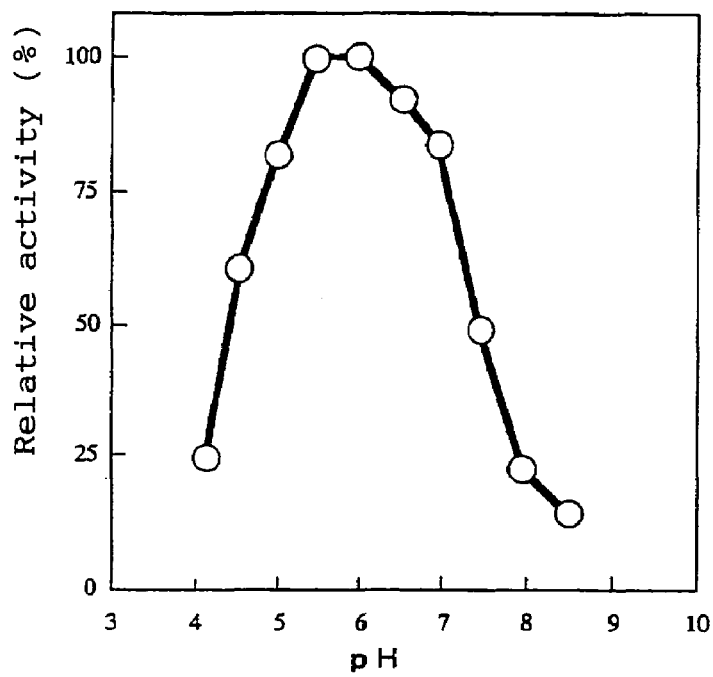
FIG. 10 shows the pH influence on α-isomaltosyl-transferring enzyme from a microorganism of the species *Bacillus globisporus* C11 strain.
Figure 11:
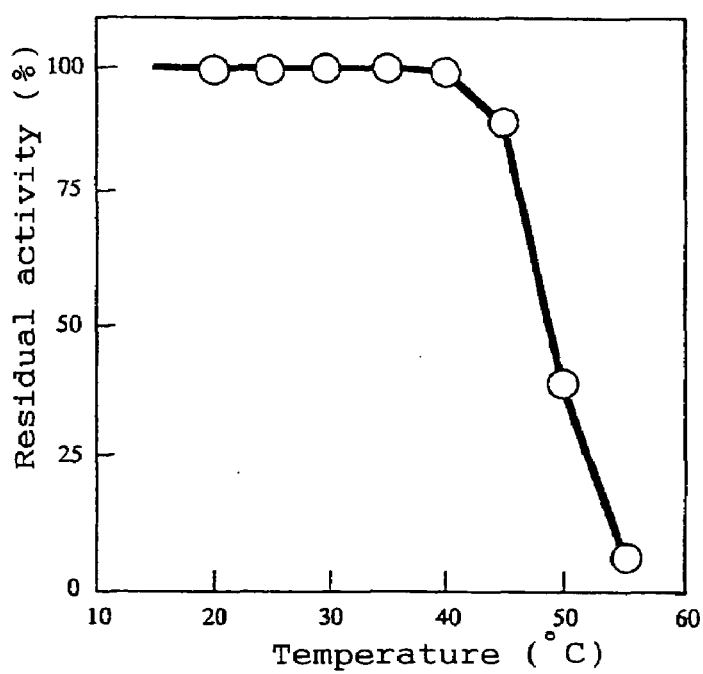
FIG. 11 shows the thermal stability of α-isomaltosyl-transferring enzyme from a microorganism of the species *Bacillus globisporus* C11 strain.
Figure 12:
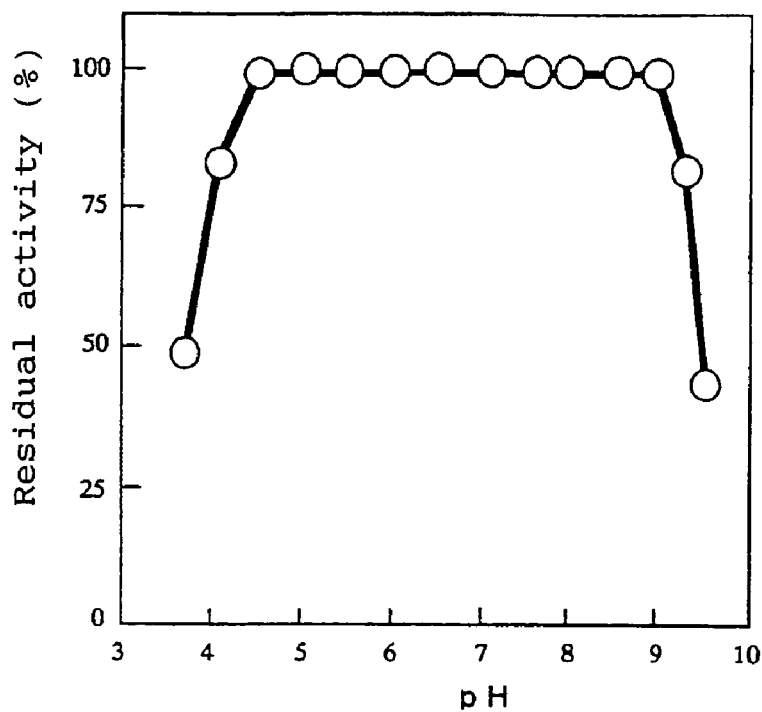
FIG. 12 shows the pH stability of α-isomaltosyl-transferring enzyme from a microorganism of the species *Bacillus globisporus* C11 strain.

The influence of temperature and pH on the activity of α-isomaltosyl-transferring enzyme was examined in accordance with the assay for the enzyme activity. The results are in FIG. 9 (influence of temperature) and FIG. 10 (influence of pH). The optimum temperature of the enzyme was about 50° C. when reacted at pH 6.0 for 30 min. The optimum pH of the enzyme was about 5.5 to about 6.0 when reacted at 35° C. for 30 min. The thermal stability of the enzyme was determined by incubating the testing enzyme solutions in 20 mM acetate buffer (pH 6.0) at prescribed temperatures for 60 min, cooling the resulting enzyme solutions with water, and assaying the remaining enzyme activity of each solution. The pH stability of the enzyme was determined by keeping the enzyme in 50 mM buffers having different pHs at 4° C. for 24 hours, adjusting the pH of each solution to 6.0, and assaying the remaining enzyme activity of each solution. The results are respectively in FIG. 11 (thermal stability) and FIG. 12 (pH stability). As a result, the enzyme had thermal stability of up to about 40° C. and pH stability of about 4.5 to about 9.0.

The influence of metal ions on the activity of α-isomaltosyl-transferring enzyme was examined in the presence of 1 mM of a metal ion according to the assay for the enzyme activity. The results are in Table 4.

TABLE 4

| Metal ion | Relative activity (%) | Metal ion | Relative activity (%) |
|---|---|---|---|
| None | 100 | $Hg^{2+}$ | 2 |
| $Zn^{2+}$ | 83 | $Ba^{2+}$ | 90 |
| $Mg^{2+}$ | 91 | $Sr^{2+}$ | 93 |
| $Ca^{2+}$ | 91 | $Pb^{2+}$ | 74 |
| $Co^{2+}$ | 89 | $Fe^{2+}$ | 104 |
| $Cu^{2+}$ | 56 | $Fe^{3+}$ | 88 |
| $Ni^{2+}$ | 89 | $Mn^{2+}$ | 93 |
| $Al^{3+}$ | 89 | EDTA | 98 |

As evident form the results in Table 4, the enzyme activity was greatly inhibited by $Hg^{2+}$ and was also inhibited by $Cu^{2+}$. It was also found that the enzyme was neither activated by $Ca^{2+}$ nor inhibited by EDTA.

Amino acid analysis of the N-terminal amino acid sequence of the enzyme by "PROTEIN SEQUENCER MODEL 473A", an apparatus of Applied Biosystems, Inc., Foster City, USA, revealed that the enzyme had a partial amino acid sequence of SEQ ID NO:10, i.e., isoleucine-aspartic acid-glycine-valine-tyrosine-histidine-alanine-proline-tyrosine-glycine in the N-terminal region.

Experiment 9

Internal Amino Acid Sequence of α-isomaltosyl-transferring Enzyme

A part of a purified specimen of α-isomaltosyl-transferring enzyme, obtained by the method in Experiment 8, was dialyzed against 10 mM Tris-HCl buffer (pH 9.0), and the dialyzed solution was diluted with a fresh preparation of the same buffer to give a concentration of about one milligram per milliliter. One milliliter of the dilute as a test sample was admixed with 10 μg of "Lysyl Endopeptidase" commercialized by Wako Pure Chemical Industries, Ltd., Tokyo, Japan, and allowed to react at 30° C. for 22 hours to form peptides. The resultant mixture was subjected to reverse-phase HPLC to separate the peptides using "μ-Bondapak C18 column" having a diameter of 2.1 mm and a length of 150 mm, a product of Waters Chromatography Div., MILLIPORE Corp., Milford, USA, at a flow rate of 0.9 ml/min and at ambient temperature, and using a liner gradient of acetonitrile increasing from 8% (v/v) to 40% (v/v) in 0.1% (v/v) trifluoroacetate over 120 min. The peptides eluted from the column were detected by monitoring the absorbency at a wavelength of 210 nm. Three peptide specimens named P22 with a retention time of about 22 min, P63 with a retention time of about 63 min. and P71 with a retention time of about 71 min, which had been well separated from other peptides, were separately collected and dried in vacuo and then dissolved in 200 μl of a solution of 50% (v/v) acetonitrile in 0.1% (v/v) trifluoroacetate. Each peptide specimen was subjected to a protein sequencer for analyzing amino acid sequence up to eight amino acid residues to obtain amino acid sequences of SEQ ID NOs:2 to 4. The analyzed internal partial amino acid sequences are in Table 5.

TABLE 5

| Peptide name | Internal partial amino acid sequence |
| --- | --- |
| P22 | glycine-asparagine-glutamic acid-methionine-arginine-asparagine-glutamine-tyrosine (SEQ ID NO: 2) |
| P63 | isoleucine-threonine-threonine-tryptophane-proline-isoleucine-glutamic acid-serine (SEQ ID NO: 3) |
| P71 | tryptophane-alanine-phenylalanine-glycine-leucine-tryptophane-methionine-serine (SEQ ID NO: 4) |

Experiment 10

Production of α-isomaltosyl-transferring Enzyme from *Bacillus globisporus* N75

A liquid nutrient culture medium, consisting of 4.0% (w/v) of "PINE-DEX #4", a partial starch hydrolysate, 1.8% (w/v) of "ASAHIMEAST", a yeast extract, 0.1% (w/v) of dipotassium phosphate, 0.06% (w/v) of sodium phosphate dodecahydrate, 0.05% (w/v) magnesium sulfate heptahydrate, and water was placed in 500-ml Erlenmeyer flasks in respective volumes of 100 ml, and then sequentially autoclaved at 121° C. for 20 minutes to effect sterilization, cooled, inoculated with a stock culture of *Bacillus globisporus* N75, FERM BP-7591, and incubated at 27° C. for 48 hours under rotary shaking conditions of 230 rpm to obtain a seed culture.

About 20 L of a fresh preparation of the same nutrient culture medium as used in the above culture were placed in a 30-L fermentor, sterilized by heating, cooled to 27° C., inoculated with 1% (v/v) of the seed culture, and incubated for about 48 hours while stirring under aeration-agitation conditions at 27° C. and pH 6.0–8.0. The resultant culture, having about 1.1 units/ml of α-isomaltosyl-transferring enzyme activity, was centrifuged at 10,000 rpm for 30 min to obtain about 18 L of a supernatant. Measurement of the supernatant revealed that it had about 1.1 units/ml of α-isomaltosyl-transferring enzyme activity, i.e., a total enzyme activity of about 19,800 units.

Experiment 11

Purification of α-isomaltosyl-transferring Enzyme from *Bacillus globisporus* N75

An 18 L of the supernatant obtained in Experiment 10 was salted out with a 60% saturated ammonium sulfate solution and allowed to stand at 4° C. for 24 hours. The salted out sediments were collected by centrifugation at 10,000 for 30 min, dissolved in 10 mM Tris-HCl buffer (pH 8.3), dialyzed against a fresh preparation of the same buffer to obtain about 450 ml of a crude enzyme solution containing about 15,700 units of α-isomaltosyl-transferring enzyme, which was then subjected to ion-exchange column chromatography using 1,000 ml of "SEPABEADS FP-DA13" gel and eluted from the column as non-adsorbed fractions without adsorbing on the gel. The non-adsorbed fractions were pooled and dialyzed against 10 mM phosphate buffer (pH 7.0) containing 1 M ammonium sulfate, and the dialyzed inner solution was centrifuged to remove insoluble substances. The resulting supernatant was subjected to affinity chromatography using 500 ml of "SEPHACRYL HR S-200" gel. The enzyme, adsorbed on the gel, was eluted at around 0.3 M ammonium sulfate when eluted with a linear gradient decreasing from 1 M to 0 M ammonium sulfate, and fractions with the enzymatic activity were collected, pooled, and dialyzed against 10 mM Tris-HCl buffer (pH 7.0) containing 1 M ammonium sulfate. The dialyzed inner solution was centrifuged to remove insoluble substances, and the resulting supernatant was subjected to hydrophobic column chromatography using 380 ml of "BUTYL-TOYOPEARL 650M" gel. The enzyme, adsorbed on the gel, was eluted at around 0.3 M ammonium sulfate when eluted with a linear gradient decreasing from 1 M to 0 M ammonium sulfate. The fractions with the enzymatic activity were collected, pooled, and dialyzed against 10 mM Tris-HCl buffer (pH 8.0), and the dialyzed inner solution was centrifuged to remove insoluble substances. The resulting supernatant was subjected to ion-exchange column chromatography using 380 ml of "SUPER Q-TOYOPEARL 650C" gel. The enzyme was eluted as non-adsorbed fractions without adsorbing on the gel and collected for use as a purified enzyme specimen. The amount of enzyme activity, specific activity, and yield of the α-isomaltosyl-transferring enzyme in each purification step are in Table 6.

TABLE 6

| Purification step | Enzyme* activity (unit) | Specific activity of enzyme* (unit/mg protein) | Yield (%) |
| --- | --- | --- | --- |
| Culture supernatant | 19,000 | 0.33 | 100 |
| Dialyzed solution after salting out with ammonium sulfate | 15,700 | 0.64 | 82.6 |
| Eluate from ion-exchange column chromatography | 12,400 | 3.56 | 65.3 |
| Eluate from affinity column chromatography | 8,320 | 11.7 | 43.8 |
| Eluate from hydrophobic column chromatography | 4,830 | 15.2 | 25.4 |
| Eluate from ion-exchange column chromatography | 3,850 | 22.6 | 20.3 |

Note:
The symbol "*" means α-isomaltosyl-transferring enzyme.

The finally purified α-isomaltosyl-transferring enzyme specimen was assayed for purity on gel electrophoresis using a 7.5% (w/v) sodium dodecyl sulfate polyacrylamide gel and detected as a single protein band, i.e., a high purity enzyme specimen.

Experiment 12

Property of α-isomaltosyl-transferring Enzyme

A purified specimen of α-isomaltosyl-transferring enzyme, obtained by the method in Experiment 11, was subjected to SDS-PAGE using a 7.5% (w/v) of sodium dodecyl sulfate polyacrylamide gel and then determined for molecular weight by comparing with the dynamics of standard molecular markers, commercialized by Bio-Rad Laboratories Inc., Brussels, Belgium, electrophoresed in parallel, revealing that the enzyme had a molecular weight of about 112,000±20,000 daltons.

A fresh preparation of the above purified specimen was subjected to isoelectrophoresis using a gel containing 2% (w/v) ampholine commercialized by Amersham Corp., Div. Amersham International, Arlington Heights, Ill., USA, and then measured for pHs of protein bands and gel to determine the isoelectric point of the enzyme, revealing that the enzyme had an isoelectric point of about 7.8±0.5.

Figure 13:
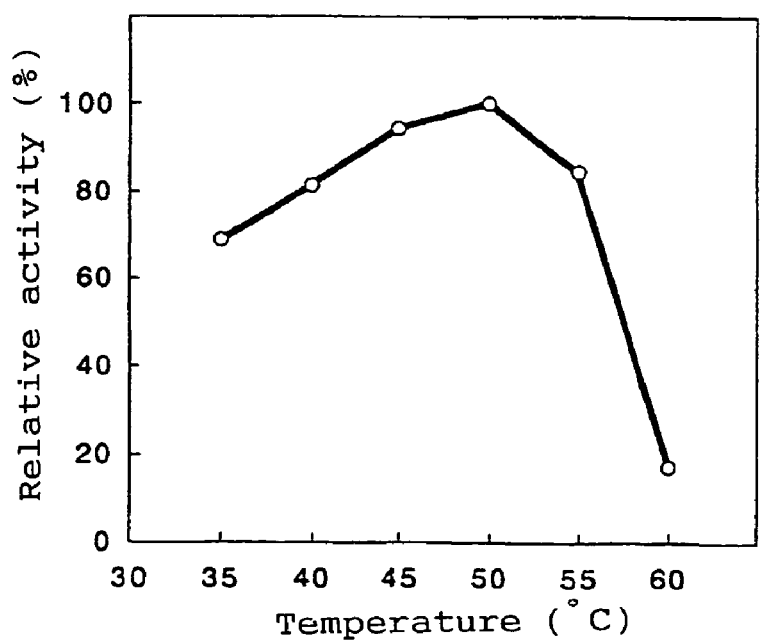
FIG. 13 shows the thermal influence on the enzymatic activity of α-isomaltosyl-transferring enzyme from a microorganism of the species *Bacillus globisporus* N75 strain.
Figure 14:
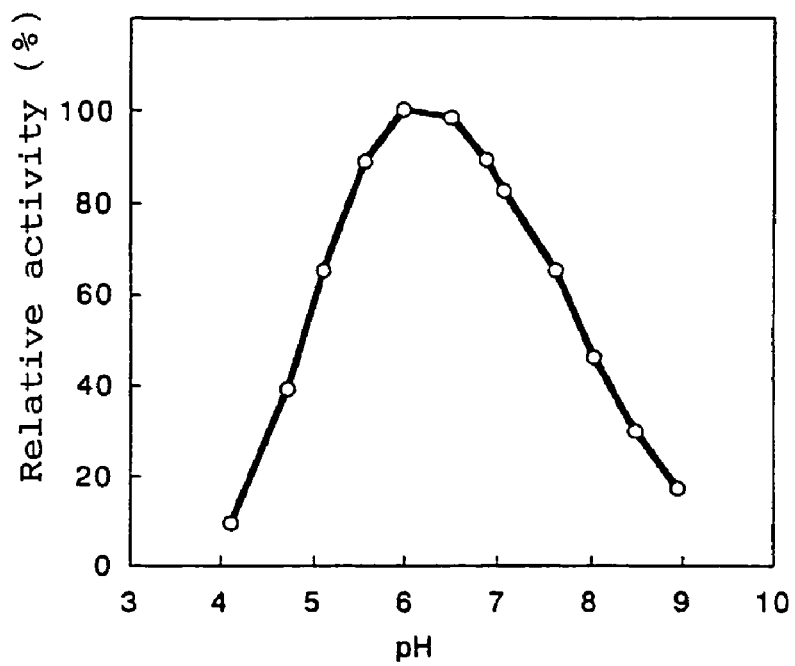
FIG. 14 shows the pH influence on the enzymatic activity of α-isomaltosyl-transferring enzyme from a microorganism of the species *Bacillus globisporus* N75 strain.
Figure 15:
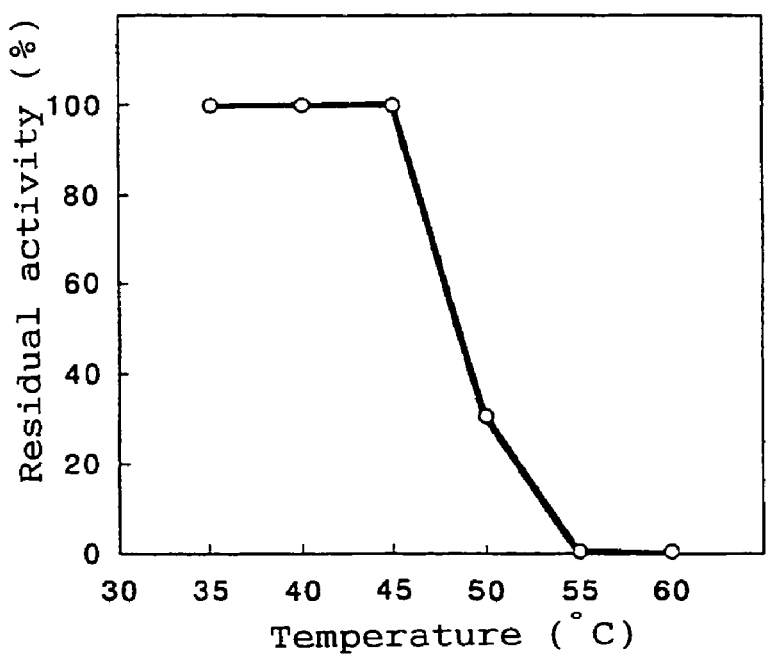
FIG. 15 shows the thermal stability of α-isomaltosyl-transferring enzyme from a microorganism of the species *Bacillus globisporus* N75 strain.
Figure 16:
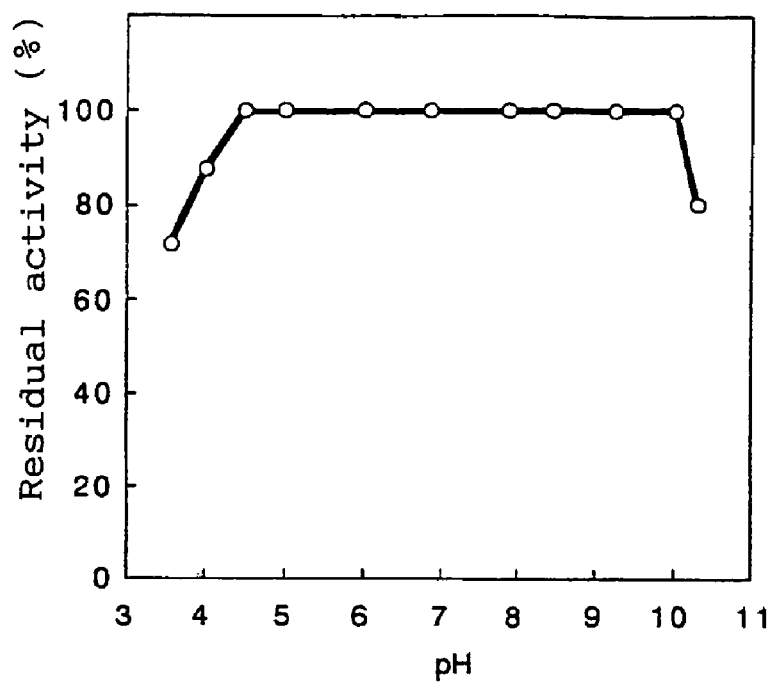
FIG. 16 shows the pH stability of α-isomaltosyl-transferring enzyme from a microorganism of the species *Bacillus globisporus* N75 strain.

The influence of temperature and pH on the activity of α-isomaltosyl-transferring enzyme was examined in accordance with the assay for the enzyme activity. These results are in FIG. 13 (influence of temperature) and FIG. 14 (influence of pH). The optimum temperature of the enzyme was about 50° C. The optimum pH of the enzyme was about 6.0 when reacted at 35° C. for 30 min. The thermal stability of the enzyme was determined by incubating the testing enzyme solutions in 20 mM acetate buffer (pH 6.0) at a prescribed temperature for 60 min, cooling with water the resulting enzyme solutions, and assaying the remaining enzyme activity of each solution. The pH stability of the enzyme was determined by keeping the enzyme in 50 mM buffers having different pHs at 4° C. for 24 hours, adjusting the pH of each solution to 6.0, and assaying the remaining enzyme activity for each solution. These results are respectively in FIG. 15 (thermal stability) and FIG. 16 (pH stability). As a result, the enzyme had thermal stability of up to about 45° C. and had pH stability of about 4.5 to about 10.0.

The influence of metal ions on the activity of α-isomaltosyl-transferring enzyme was examined in the presence of 1 mM of a metal ion according to the assay for the enzyme activity. The results are in Table 7.

TABLE 7

| Metal ion | Relative activity (%) | Metal ion | Relative activity (%) |
|---|---|---|---|
| None | 100 | $Hg^{2+}$ | 0.5 |
| $Zn^{2+}$ | 75 | $Ba^{2+}$ | 102 |
| $Mg^{2+}$ | 95 | $Sr^{2+}$ | 91 |
| $Ca^{2+}$ | 100 | $Pb^{2+}$ | 69 |
| $Co^{2+}$ | 92 | $Fe^{2+}$ | 97 |
| $Cu^{2+}$ | 15 | $Fe^{3+}$ | 90 |
| $Ni^{2+}$ | 91 | $Mn^{2+}$ | 101 |
| $Al^{3+}$ | 94 | EDTA | 92 |

As evident form the results in Table 7, the enzyme activity was greatly inhibited by $Hg^{2+}$ and was also inhibited by $Cu^{2+}$. It was also found that the enzyme was neither activated by $Ca^{2+}$ nor inhibited by EDTA.

Amino acid analysis of the N-terminal amino acid sequence of the enzyme using "PROTEIN SEQUENCER MODEL 473A", an apparatus of Applied Biosystems, Inc., Foster City, USA, revealed that it had isoleucine-aspartic acid-glycine-valine-tyrosine-histidine-alanine-proline-tyrosine-glycine at the N-terminal region, identical to the N-terminal amino acid sequence (SEQ ID NO:8) of the enzyme of Strain C11 in Experiment 8.

Considering totally the results of the above partial amino acid sequence at the N-terminal region and those at the N-terminal region of the α-isomaltosyl-transferring enzymes from *Bacillus globisporus* C9 and C11 in Experiments 5 and 8, the enzymes from microorganisms of the genus *Bacillus* have a common amino acid sequence of SEQ ID NO:1 at their N-terminal regions.

Experiment 13

Internal Amino Acid Sequence of α-isomaltosyl-transferring Enzyme

A part of a purified specimen of α-isomaltosyl-transferring enzyme, obtained by the method in Experiment 11, was dialyzed against 10 mM Tris-HCl buffer (pH 9.0), and the dialyzed solution was diluted with a fresh preparation of the same buffer to give a concentration of about one milligram per milliliter. One milliliter of the dilute as a test sample was admixed with 10 μg of "Lysyl Endopeptidase" commercialized by Wako Pure Chemical Industries, Ltd., Tokyo, Japan, and allowed to react at 30° C. for 22 hours to form peptides. The resultant mixtures were subjected to reverse-phase HPLC to separate the peptides using "μ-Bondasphere C18 column" having a diameter of 2.1 mm and a length of 150 mm, a product of Waters Chromatography Div., MILLIPORE Corp., Milford, USA, at a flow rate of 0.9 ml/min and at ambient temperature, and using a liner gradient of acetonitrile increasing from 4% (v/v) to 42.4% (v/v) in 0.1% (v/v) trifluoroacetate over 120 min. The peptides eluted from the column were detected by monitoring the absorbency at a wavelength of 210 nm. Three peptide specimens named PN21 with a retention time of about 21 min, PN38 with a retention time of about 38 min, and PN69 with a retention time of about 69 min, which had been well separated from other peptides, were separately collected and dried in vacuo and then dissolved in 200 μl of a solution of 50% (v/v) acetonitrile in 0.1% (v/v) trifluoroacetate. Each peptide specimen was subjected to a protein sequencer for analyzing amino acid sequence up to six or eight amino acid residues to obtain amino acid sequences of SEQ ID NOs:5 to 7. The analyzed internal partial amino acid sequences are in Table 8.

TABLE 8

| Peptide name | Internal partial amino acid sequence |
|---|---|
| PN21 | asparagine-tryptophane-tryptophane-methionine-serine-lysine (SEQ ID NO: 5) |
| PN38 | threonine-aspartic acid-glycine-glycine-glutamic acid-methionine-valine-tryptophane (SEQ ID NO: 6) |
| PN69 | asparagine-isoleucine-tyrosine-leucine-proline-glutamine-glycine-aspartic acid (SEQ ID NO: 7) |

Experiment 14

Production of α-isomaltosyl-transferring Enzyme from *Arthrobacter ramosus* S1

A liquid nutrient culture medium, consisting of 4.0% (w/v) of "PINE-DEX #4", a partial starch hydrolysate, 1.8% (w/v) of "ASAHIMEAST", a yeast extract, 0.1% (w/v) of dipotassium phosphate, 0.06% (w/v) of sodium phosphate dodecahydrate, 0.05% (w/v) magnesium sulfate heptahydrate, and water was placed in 500-ml Erlenmeyer flasks in respective volumes of 100 ml, and then sequentially autoclaved at 121° C. for 20 minutes to effect sterilization, cooled, inoculated with a stock culture of *Arthrobacter*

*ramosus* S1, FERM BP-7592, and incubated at 27° C. for 48 hours under rotary shaking conditions of 230 rpm to obtain a seed culture.

About 20 L of a fresh preparation of the same nutrient culture medium as used in the above culture were placed in a 30-L fermentor, sterilized by heating, cooled to 27° C., inoculated with 1% (v/v) of the seed culture, and incubated for about 48 hours while stirring under aeration-agitation conditions at 27° C. and a pH of 6.0–8.0. The resultant culture, having about 0.45 unit/ml of α-isomaltosyl-transferring enzyme activity, was centrifuged at 10,000 rpm for 30 min to obtain about 18 L of a supernatant having about 0.44 unit/ml of α-isomaltosyl-transferring enzyme activity in a total enzyme activity of about 7,920 units.

Experiment 15

Purification of α-isomaltosyl-transferring Enzyme from *Arthrobacter ramosus* S1

Eighteen liters of a supernatant obtained in Experiment 14 were salted out with a 80% (w/v) ammonium sulfate solution at 4° C. for 24 hours, and the resulting sediments were collected by centrifugation at 10,000 rpm for 30 min and dialyzed against 10 mM phosphate buffer (pH 7.0) to obtain about 380 ml of a crude enzyme solution having 6,000 units of α-isomaltosyl-transferring enzyme. The crude enzyme solution was dialyzed against 10 mM phosphate buffer (pH 7.0) containing 1 M ammonium sulfate, and the dialyzed solution was centrifuged to remove impurities. The resulting supernatant was fed to affinity column chromatography using 500 ml of "SEPHACRYL HR S-200" gel. The enzyme, adsorbed on the gel, was eluted sequentially with a linear gradient decreasing from 1 M to 0 M of ammonium sulfate and with a linear gradient increasing from 0% (w/v) to 5% (w/v) of maltotetraose, resulting in an elution of the enzyme from the gel at a concentration of about 2% (w/v) of maltotetraose and collecting fractions with the enzyme activity. The fractions were pooled and dialyzed against 10 mM phosphate buffer (pH 7.0) containing 1 M ammonium sulfate, and the dialyzed solution was centrifuged to remove impurities. The supernatant thus obtained was fed to hydrophobic column chromatography using 380 ml of "BUTYL-TOYOPEARL 650M" gel. When eluted with a linear gradient decreasing from 1 M to 0 M ammonium sulfate, the α-isomaltosyl-transferring enzyme adsorbed on the gel was eluted therefrom at about 0.3 M ammonium sulfate, followed by collecting fractions with the enzyme activity for a purified enzyme specimen. The amount of enzyme activity, specific activity, and yield of the α-isomaltosyl-transferring enzyme in each purification step are in Table 9.

TABLE 9

| Purification step | Enzyme* activity (unit) | Specific activity of enzyme* (unit/mg protein) | Yield (%) |
|---|---|---|---|
| Culture supernatant | 7,920 | 0.47 | 100 |
| Dialyzed solution after salting out with ammonium sulfate | 6,000 | 3.36 | 75.8 |
| Eluate from affinity column chromatography | 5,270 | 29.9 | 66.5 |
| Eluate from hydrophobic column chromatography | 4,430 | 31.1 | 55.9 |

Note:
The symbol "*" means α-isomaltosyl-transferring enzyme.

The purified α-isomaltosyl-transferring enzyme specimen in this experiment was assayed for purity on gel electrophoresis using a 7.5% (w/v) sodium dodecyl sulfate polyacrylamide gel and detected as a single protein band, i.e., a high purity enzyme specimen.

Experiment 16

Property of α-isomaltosyl-transferring Enzyme

A purified specimen of α-isomaltosyl-transferring enzyme, obtained by the method in Experiment 15, was subjected to SDS-PAGE using a 7.5% (w/v) of sodium dodecyl sulfate polyacrylamide gel and then determined for molecular weight by comparing with the dynamics of standard molecular markers, commercialized by Bio-Rad Laboratories Inc., Brussels, Belgium, electrophoresed in parallel, revealing that the enzyme had a molecular weight of about 116,000±20,000 daltons.

A fresh preparation of the above purified specimen was subjected to isoelectrophoresis using a polyacrylamide gel containing 2% (w/v) ampholine commercialized by Amersham Corp., Div. Amersham International, Arlington Heights, Ill., USA, and then measured for pHs of protein bands and gels to determine the isoelectric point of the enzyme, revealing that the enzyme had an isoelectric point of about 4.2±0.5.

Figure 17:
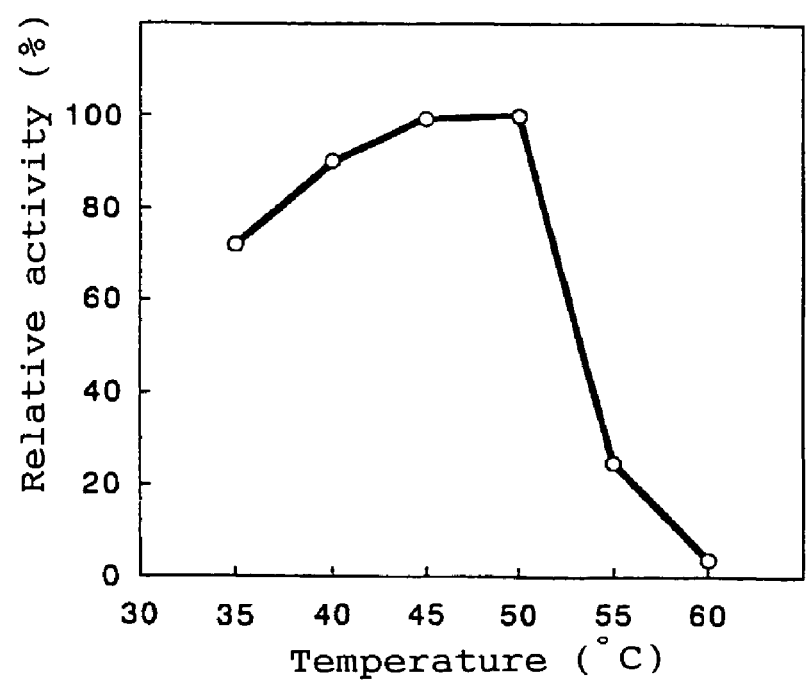
FIG. 17 shows the thermal influence on the enzymatic activity of α-isomaltosyl-transferring enzyme from a microorganism of the species *Arthrobacter ramosus* S1 strain.
Figure 18:
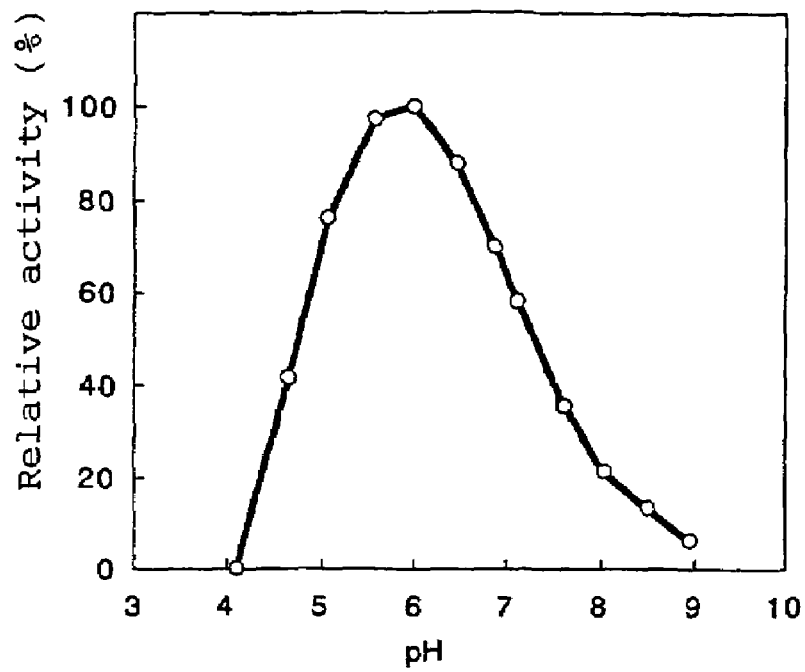
FIG. 18 shows the pH influence on the enzymatic activity of α-isomaltosyl-transferring enzyme from a microorganism of the species *Arthrobacter ramosus* S1 strain.
Figure 19:
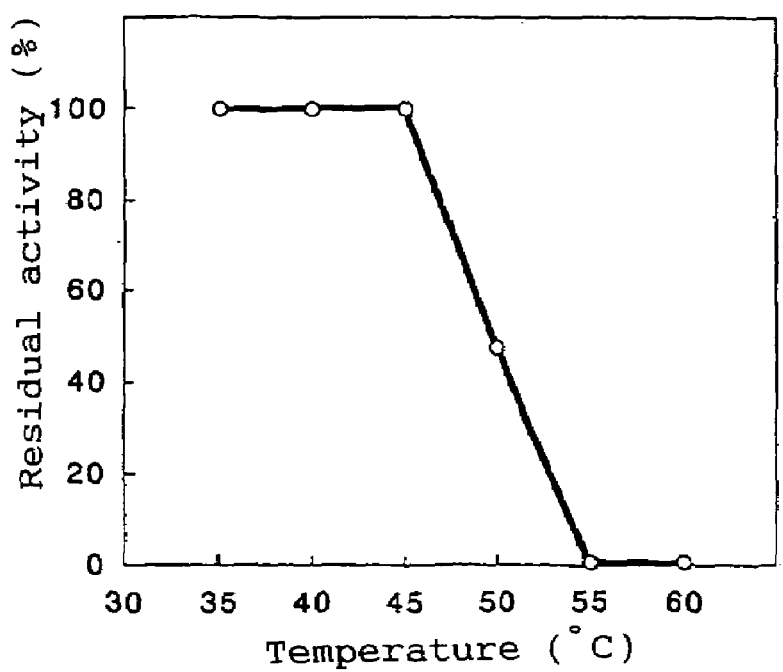
FIG. 19 shows the thermal stability of α-isomaltosyl-transferring enzyme from a microorganism of the species *Arthrobacter ramosus* S1 strain.
Figure 20:
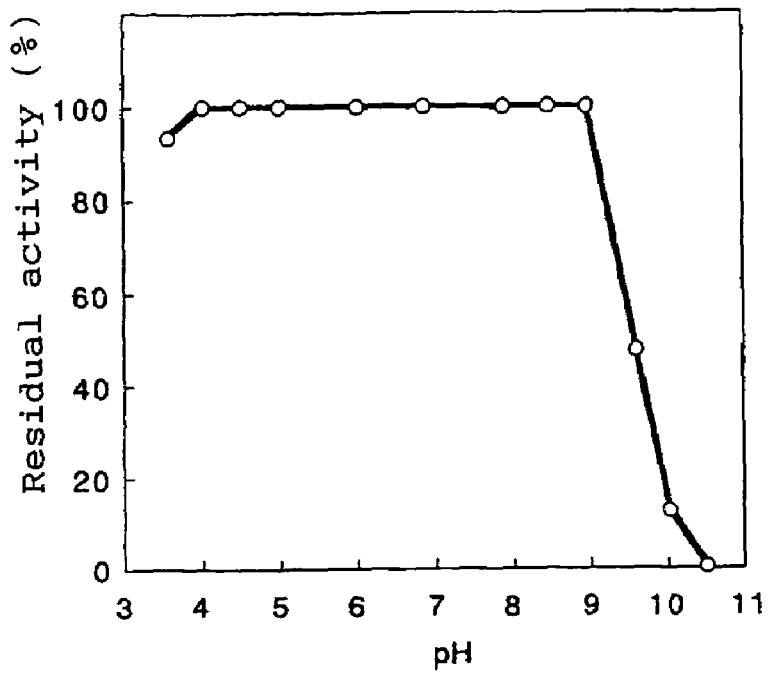
FIG. 20 shows the pH stability of α-isomaltosyl-transferring enzyme from a microorganism of the species *Arthrobacter ramosus* S1 strain.

The influence of temperature and pH on the activity of α-isomaltosyl-transferring enzyme was examined in accordance with the assay for the enzyme activity. The results are in FIG. 17 (influence of temperature) and FIG. 18 (influence of pH). The optimum temperature of the enzyme was about 50° C. when reacted at pH 6.0 for 30 min. The optimum pH of the enzyme was about 6.0 when reacted at 35° C. for 30 min. The thermal stability of the enzyme was determined by incubating the testing enzyme solutions at prescribed temperatures for 60 min in 20 mM acetate buffer (pH 6.0), cooling the resulting enzyme solutions with water, and assaying the remaining enzyme activity of each solution. The pH stability of the enzyme was determined by keeping the enzyme in 50 mM buffers having different pHs at 4° C. for 24 hours, adjusting the pH of each solution to 6.0, and assaying the remaining enzyme activity of each solution. These results are respectively in FIG. 19 (thermal stability) and FIG. 20 (pH stability). As shown in these figures, the enzyme had thermal stability of up to about 45° C. and had pH stability of about 3.6 to about 9.0 under the above conditions.

The influence of metal ions on the activity of α-isomaltosyl-transferring enzyme was examined in the presence of 1 mM of a metal ion according to the assay for the enzyme activity. The results are in Table 10.

TABLE 10

| Metal ion | Relative activity (%) | Metal ion | Relative activity (%) |
|---|---|---|---|
| None | 100 | $Hg^{2+}$ | 0.1 |
| $Zn^{2+}$ | 78 | $Ba^{2+}$ | 97 |
| $Mg^{2+}$ | 99 | $Sr^{2+}$ | 101 |
| $Ca^{2+}$ | 103 | $Pb^{2+}$ | 85 |
| $Co^{2+}$ | 91 | $Fe^{2+}$ | 105 |
| $Cu^{2+}$ | 2 | $Fe^{3+}$ | 75 |
| $Ni^{2+}$ | 87 | $Mn^{2+}$ | 98 |
| $Al^{3+}$ | 93 | EDTA | 91 |

As evident form the results in Table 10, it was revealed that the enzyme activity was greatly inhibited by $Hg^{2+}$ and was also inhibited by $Cu^{2+}$. It was also found that the enzyme was neither activated by $Ca^{2+}$ nor inhibited by EDTA.

Amino acid analysis of the N-terminal amino acid sequence of the enzyme by "PROTEIN SEQUENCER MODEL 473A", an apparatus of Applied Biosystems, Inc., Foster City, USA, revealed that the enzyme had a partial amino acid sequence of SEQ ID NO:8, i.e., aspartic acid-threonine-leucine-serine-glycine-valine-phenylalanine-histidine-glycine-proline at the N-terminal region.

Experiment 17

Production of α-isomaltosyl-transferring Enzyme from *Arthrobacter globiformis* A19

A liquid nutrient culture medium, consisting of 4.0% (w/v) of "PINE-DEX #4", a partial starch hydrolysate, 1.8% (w/v) of "ASAHIMEAST", a yeast extract, 0.1% (w/v) of dipotassium phosphate, 0.06% (w/v) of sodium phosphate dodecahydrate, 0.05% (w/v) magnesium sulfate heptahydrate, and water was placed in 500-ml Erlenmeyer flasks in respective volumes of 100 ml, and then sequentially autoclaved at 121° C. for 20 minutes to effect sterilization, cooled, inoculated with a stock culture of *Arthrobacter globiformis* A19, FERM BP-7590, and incubated at 27° C. for 48 hours under rotary shaking conditions of 230 rpm to obtain a seed culture.

About 20 L of a fresh preparation of the same nutrient culture medium as used in the above culture were placed in a 30-L fermentor, sterilized by heating, cooled to 27° C., inoculated with one percent (v/v) of the seed culture, and incubated for about 48 hours while stirring under aeration-agitation conditions at 27° C. and a pH of 6.0–9.0. The resultant culture, having about 1.7 units/ml of α-isomaltosyl-transferring enzyme activity, was centrifuged at 10,000 rpm for 30 min to obtain about 18 L of a supernatant. Measurement of the supernatant revealed that it had about 1.6 units/ml of α-isomaltosyl-transferring enzyme activity, i.e., a total enzyme activity of about 28,800 units.

Experiment 18

Partial Purification of α-isomaltosyl-transferring Enzyme from *Arthrobacter globiformis* A19

About 18 L of the supernatant, obtained in Experiment 17, was salted out with a 60% saturated ammonium sulfate solution and allowed to stand at 4° C. for 24 hours. Then, the salted out sediments were collected by centrifugation at 10,000 for 30 min, dissolved in 10 mM phosphate buffer (pH 7.0), dialyzed against a fresh preparation of the same buffer to obtain about 850 ml of a crude enzyme solution having about 15,700 units of α-isomaltosyl-transferring enzyme, followed by subjecting the crude enzyme solution to ion-exchange column chromatography using 380 ml of "DEAE-TOYOPEARL 650S" gel. When eluted with a linear gradient increasing from 0 M to 0.5 M NaCl, the above enzyme adsorbed on the gel was eluted from therefrom at a concentration of about 0.3 M NaCl, followed by collecting fractions with the enzyme activity. The fractions were pooled and dialyzed against 10 mM phosphate buffer (pH 7.0) containing 1 M ammonium sulfate, and the dialyzed solution was centrifuged to remove impurities. The resulting supernatant was fed to affinity column chromatography using 500 ml of "SEPHACRYL HR S-200" gel, a gel commercialized by Amersham Corp., Div. Amersham International, Arlington Heights, Ill., USA. The enzyme, adsorbed on the gel, was eluted with a linear gradient decreasing from 1 M to 0 M of ammonium sulfate, resulting in an elution of the enzyme from the gel at a concentration of about 0 M ammonium sulfate and collecting fractions with the enzyme activity for a partially purified specimen. The amount of enzyme activity, specific activity, and yield of the α-isomaltosyl-transferring enzyme in each purification step are in Table 11.

TABLE 11

| Purification step | Enzyme* activity (unit) | Specific activity of enzyme* (unit/mg protein) | Yield (%) |
| --- | --- | --- | --- |
| Culture supernatant | 28,800 | 0.18 | 100 |
| Dialyzed solution after salting out with ammonium sulfate | 15,700 | 0.97 | 54.5 |
| Eluate from ion-exchange column chromatography | 7,130 | 4.01 | 24.8 |
| Eluate from affinity column chromatography | 1,800 | 11.9 | 6.3 |

Note:
The symbol "*" means α-isomaltosyl-transferring enzyme.

The partially-purified α-isomaltosyl-transferring enzyme specimen was assayed for purity on gel electrophoresis using a 7.5% (w/v) sodium dodecyl sulfate polyacrylamide gel and detected as a main protein band along with three minor protein bands.

Experiment 19

Property of α-Isomaltosyl-transferring Enzyme

Figure 21:
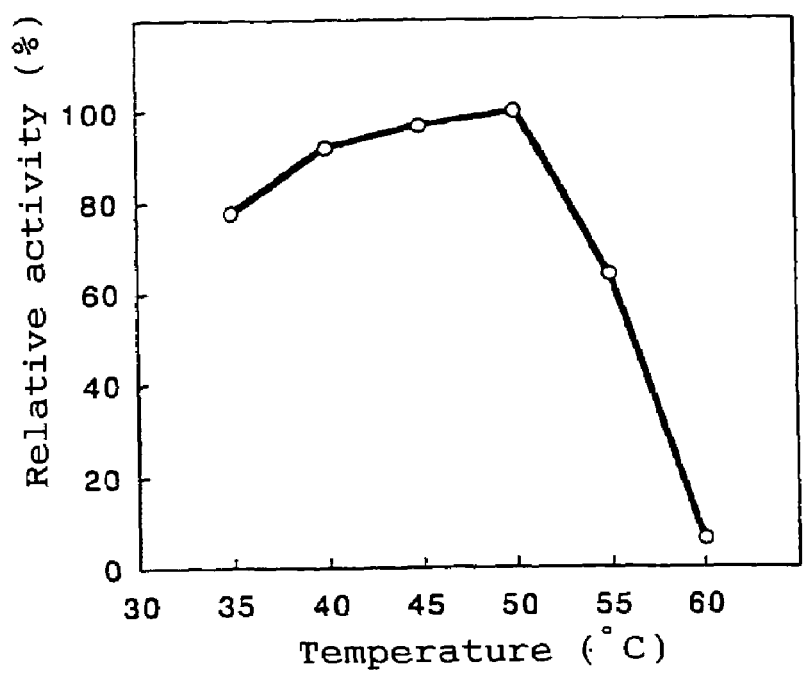
FIG. 21 shows the thermal influence on the enzymatic activity of α-isomaltosyl-transferring enzyme from a microorganism of the species *Arthrobacter globiformis* A19 strain.
Figure 22:
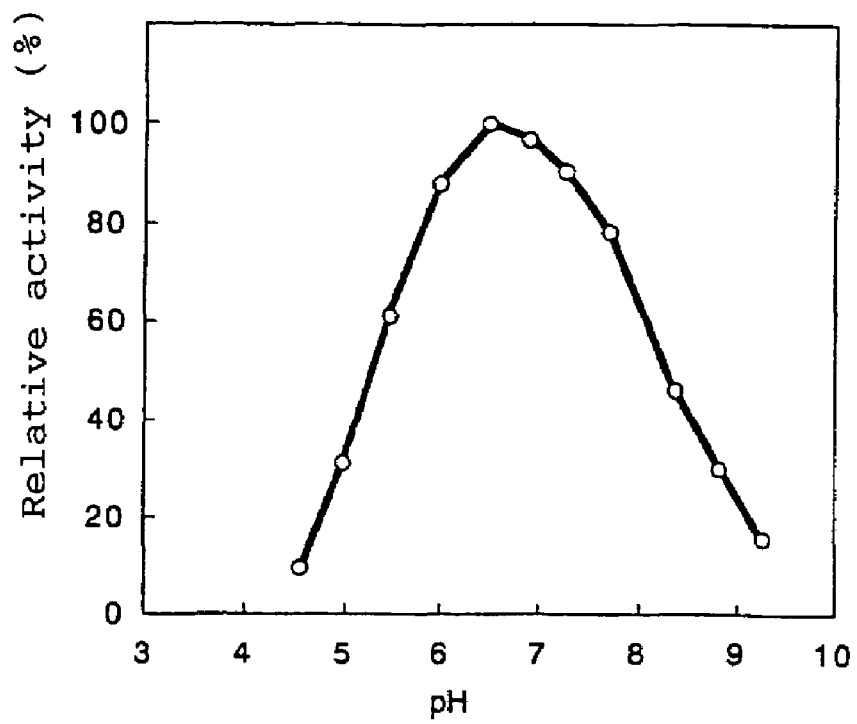
FIG. 22 shows the pH influence on the enzymatic activity of α-isomaltosyl-transferring enzyme from a microorganism of the species *Arthrobacter globiformis* A19 strain.
Figure 23:
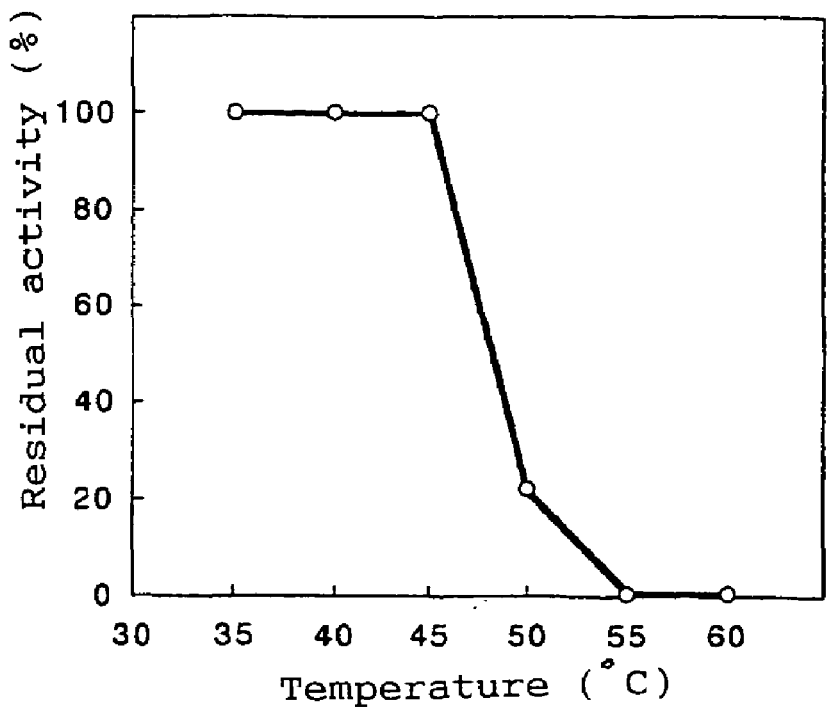
FIG. 23 shows the thermal stability of α-isomaltosyl-transferring enzyme from a microorganism of the species *Arthrobacter globiformis* A19 strain.
Figure 24:
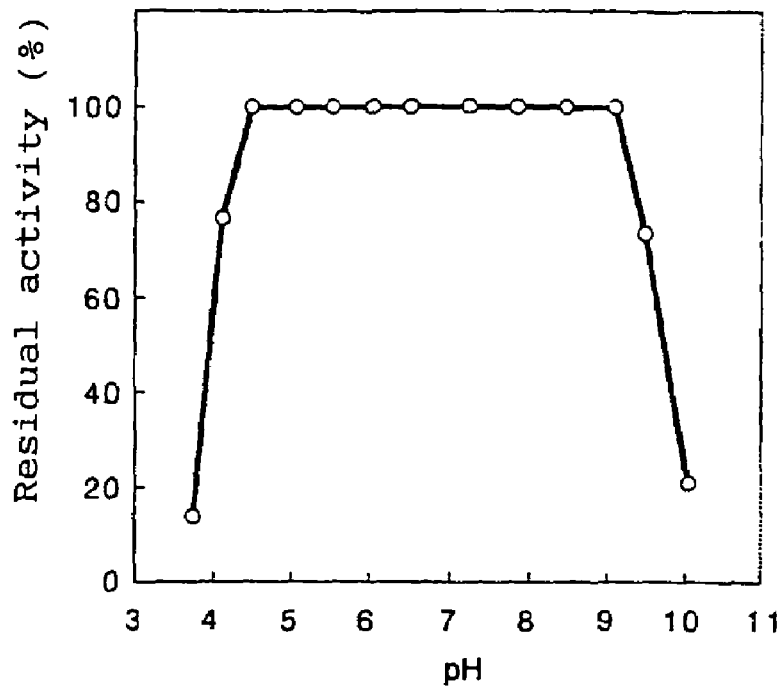
FIG. 24 shows the pH stability of α-isomaltosyl-transferring enzyme from a microorganism of the species *Arthrobacter globiformis* A19 strain.

Using a partially-purified specimen of α-isomaltosyl-transferring enzyme, obtained by the method in Experiment 18, the influence of temperature and pH on the enzyme was examined in accordance with the assay for the enzyme activity. The results are in FIG. 21 (influence of temperature) and FIG. 22 (influence of pH). The optimum temperature of the enzyme was about 50° C. when reacted at pH 6.0 for 30 min. The optimum pH of the enzyme was about 6.5 when reacted at 35° C. for 30 min. The thermal stability of the enzyme was determined by incubating the testing enzyme solutions in 20 mM acetate buffer (pH 6.0) at prescribed temperatures for 60 min, cooling with water the resulting enzyme solutions, and assaying the remaining enzyme activity of each solution. The pH stability of the enzyme was determined by keeping the enzyme in 50 mM buffers having different pHs at 4° C. for 24 hours, adjusting the pH of each solution to 6.0, and assaying the remaining enzyme activity of each solution. These results are respectively in FIG. 23 (thermal stability) and FIG. 24 (pH stability). As shown in these figures, the enzyme had thermal stability of up to about 45° C. and pH stability of about 4.5 to about 9.0 under the above conditions.

Experiment 20

Action on Saccharides

It was tested whether saccharides can be used as substrates for the α-isomaltosyl-transferring enzyme. For the purpose, a solution of maltose, maltotriose, maltotetraose, maltopentaose, maltohexaose, maltoheptaose, isomaltose, isomaltotriose, panose, isomaltosylmaltose, isopanose, α,α-trehalose, kojibiose, nigerose, α,β-trehalose, cellobiose, gentibiose, maltitol, maltotriitol, lactose, sucrose, α-cyclodextrin, β-cyclodextrin, γ-cyclodextrin, soluble starch, pullulan, or dextran was prepared. To each of the above solutions was added two units/g substrate of a purified specimen of either α-isomaltosyl-transferring enzyme from *Bacillus globisporus* C9 obtained by the method in Experiment 4, *Bacillus globisporus* C11 obtained by the method in Experiment 7, *Bacillus globisporus* N75 obtained by the method in Experiment 11, or *Arthrobacter ramosus* S1 obtained by the method in Experiment 15, or a partially purified α-isomaltosyl-transferring enzyme from *Arthrobacter globiformis* A19 obtained by the method in Experiment 15. The resulting each solution was adjusted to give a substrate concentration of 2% (w/v) and incubated at 30° C. and pH 6.0 for 24 hours. The enzyme solutions before and after the enzymatic reactions were respectively analyzed on TLC as disclosed in Experiment 1 to confirm whether the enzymes acted on these substrates. The results are in Table 12.

TABLE 12

Enzymatic action for forming cyclotetrasaccharide

| Substrate | Enzyme of Strain C9 | Enzyme of Strain C11 | Enzyme of Strain N75 | Enzyme of Strain S1 | Enzyme of Strain A19 |
|---|---|---|---|---|---|
| Maltose | – | – | – | – | – |
| Maltotriose | – | – | – | – | – |
| Maltotetraose | – | – | – | – | – |
| Maltopentaose | – | – | – | – | – |
| Maltohexaose | – | – | – | – | – |
| Maltoheptaose | – | – | – | – | – |
| Isomaltose | – | – | – | – | – |
| Isomaltotriose | – | – | – | – | – |
| Panose | + | + | + | + | + |
| Isomaltosylmaltose | + | + | + | + | + |
| Isopanose | – | – | – | – | – |
| α,α-Trehalose | – | – | – | – | – |
| Kojibiose | – | – | – | – | – |
| Nigerose | – | – | – | – | – |
| α,β-trehalose (neotrehalose) | – | – | – | – | – |
| Cellobiose | – | – | – | – | – |
| Gentibiose | – | – | – | – | – |
| Maltitol | – | – | – | – | – |
| Maltotriitol | – | – | – | – | – |
| Lactose | – | – | – | – | – |
| Sucrose | – | – | – | – | – |
| α-Cyclodextrin | – | – | – | – | – |
| β-Cyclodextrin | – | – | – | – | – |
| γ-Cyclodextrin | – | – | – | – | – |
| Soluble starch | – | – | – | – | – |
| Pullulan | – | – | – | – | – |
| Dextran | – | – | – | – | – |

Note:
The symbol "–" means that there was found no substrate change before and after the enzymatic reaction, while the symbol "+" means that there were found both the reduction of substrate and the formation of cyclotetrasaccharide after the enzymatic reaction.

As evident from the Table 12, it was revealed that the α-isomaltosyl-transferring enzyme of the present invention formed cyclotetrasaccharide through the action on panose (alias isomaltosylglucose) and isomaltosylmaltose, among the saccharides tested, both of which are a saccharide having a glucose polymerization degree of at least three, and which have an isomaltosyl residue having both the α-1,6 glucosidic linkage at their non-reducing ends and the α-1,4 glucosidic linkage other than the linkage at their non-reducing end. When the yield of cyclotetrasaccharide formed from the above-identified saccharides was calculated based on the saccharide composition assayed on HPLC in accordance with the method in Experiment 1, all the enzymes used in this experiment gave a yield of about 43 to about 44% from panose and a yield of about 31% from isomaltosylmaltose.

It was revealed that the α-isomaltosyl-transferring enzyme of the present invention does not act on isomaltotriose which has the α-1,6 glucosidic linkage at its non-reducing end and further has the α-1,6 glucosidic linkage other than the linkage at the non-reducing end. In the above experiment, no detectable amount of a lower molecular weight saccharide such as cyclotetrasaccharide detectable on TLC was formed from soluble starch, pullulan and dextran as high molecular glucans. The following test was carried out to confirm that the α-isomaltosyl-transferring enzyme of the present invention neither increase the reducing power of the above high molecular glucans nor hydrolyze them. To a solution of soluble starch, pullulan or dextran was added 12 units/g substrate of a purified specimen of α-isomaltosyl-transferring enzyme from either *Bacillus globisporus* C9 obtained by the method in Experiment 4, *Bacillus globisporus* C11 obtained by the method in Experiment 7, *Bacillus globisporus* N75 obtained by the method in Experiment 11, or *Arthrobacter ramosus* S1 obtained by the method in Experiment 15. The resulting each solution was adjusted to give a substrate concentration of one percent (w/v) and incubated at 35° C. and pH 6.0 for four hours. The reducing saccharide contents and the total sugar contents in the resulting reaction mixtures after the enzymatic reactions were respectively quantified by the Somogyi-Nelson's method and the anthrone-sulfuric acid reaction method. The percentage of forming reducing power was calculated by the following equation, and the results are in Table 13:

Equation:

$$\text{Percentage of forming reducing power (\%)} = \left(\frac{AR}{AT} - \frac{BR}{BT}\right) \times 100$$

AR: Reducing sugar content after enzymatic reaction.

AT: Total sugar content after enzymatic reaction.

BR: Reducing sugar content before enzymatic reaction.

BT: Total sugar content before enzymatic reaction.

TABLE 13

| Enzyme | Substrate | Percentage of forming reducing power (%) | | | | |
|---|---|---|---|---|---|---|
| | | 0 hr* | 1 hr* | 2 hr* | 3 hr* | 4 hr* |
| Enzyme of Strain C9 | Soluble starch | 0.0 | 0.0 | 0.0 | 0.0 | 0.0 |
| | Pullulan | 0.0 | 0.0 | 0.0 | 0.0 | 0.0 |
| | Dextran | 0.0 | 0.0 | 0.0 | 0.1 | 0.0 |
| Enzyme of Strain C11 | Soluble starch | 0.0 | 0.1 | 0.0 | 0.0 | 0.0 |
| | Pullulan | 0.0 | 0.0 | 0.0 | 0.0 | 0.0 |
| | Dextran | 0.0 | 0.0 | 0.0 | 0.0 | 0.0 |
| Enzyme of Strain N75 | Soluble starch | 0.0 | 0.0 | 0.0 | 0.0 | 0.0 |
| | Pullulan | 0.0 | 0.0 | 0.0 | 0.0 | 0.0 |
| | Dextran | 0.0 | 0.0 | 0.0 | 0.0 | 0.0 |
| Enzyme of Strain N75 | Soluble starch | 0.0 | 0.0 | 0.0 | 0.0 | 0.0 |
| | Pullulan | 0.0 | 0.0 | 0.0 | 0.0 | 0.0 |
| | Dextran | 0.0 | 0.0 | 0.0 | 0.0 | 0.0 |

Note:
The symbol "*" means the time after the initiation of enzymatic reaction.

As evident from the results in Table 13, there was found no substantial increase of the reducing power of soluble starch, pullulan, and dextran, revealing that the α-isoamltosyl-transferring enzyme does not substantially hydrolyze these high molecular saccharides.

As evident from the results in Tables 12 and 13, it can be judged that the α-isoamltosyl-transferring enzyme of the present invention forms cyclotetrasaccharide by acting on saccharides which have a glucose polymerization degree of at least three and have both the α-1,6 glucosidic linkage at their non-reducing ends and the α-1,4 glucosidic linkage other than the linkange at their non-reducing ends.

Experiment 21

Product from Panose

To a five percent aqueous panose solution was added four units/g substrate of a purified specimen of either α-isomaltosyl-transferring enzyme from *Bacillus globisporus* C9 obtained by the method in Experiment 4, *Bacillus globisporus* C11 obtained by the method in Experiment 7, *Bacillus globisporus* N75 obtained by the method in Experiment 11, or *Arthrobacter ramosus* S1 obtained by the method in Experiment 15, or a partially purified specimen of α-isomaltosyl-transferring enzyme from *Arthrobacter globiformis* A19 obtained by the method in Experiment 18, and the resulting mixtures were allowed to react at 30° C. and pH 6.0 for 1 to 12 hours. The saccharide composition of the resulting reaction mixtures were assayed on HPLC. The results are in Table 14.

TABLE 14

| Enzyme | Reaction time (hr) | Saccharide composition (%) | | | | | |
|---|---|---|---|---|---|---|---|
| | | Glc* | Pan* | CTS* | A* | B* | C* | Others |
| Enzyme of Strain C9 | 1 | 5.3 | 80.4 | 4.1 | 4.5 | 3.3 | 2.0 | 0.4 |
| | 12 | 31.9 | 5.0 | 43.0 | 0.0 | 6.0 | 2.4 | 11.7 |
| Enzyme of Strain C11 | 1 | 5.2 | 80.5 | 4.0 | 4.6 | 3.3 | 1.9 | 0.5 |
| | 12 | 32.2 | 4.6 | 43.5 | 0.0 | 5.8 | 2.3 | 11.6 |
| Enzyme of Strain N75 | 1 | 5.5 | 80.0 | 4.2 | 4.4 | 3.5 | 2.0 | 0.4 |
| | 12 | 31.8 | 4.4 | 43.2 | 0.0 | 6.5 | 2.4 | 11.7 |
| Enzyme of Strain S1 | 1 | 5.0 | 81.1 | 3.8 | 4.2 | 3.8 | 1.9 | 0.2 |
| | 12 | 32.5 | 4.0 | 43.0 | 0.0 | 6.8 | 2.3 | 11.4 |
| Enzyme of Strain A19 | 1 | 5.2 | 80.7 | 4.0 | 4.3 | 3.6 | 1.9 | 0.3 |
| | 12 | 32.2 | 4.2 | 43.1 | 0.0 | 6.6 | 2.3 | 11.6 |

Note of the symbol "*":
"Glc", "Pan" and "CTS" mean glucose, panose, and cyclotetrasaccharide, respectively. "A", "B" and "C" mean unidentified components A, B and C, respectively.

As evident from the result in Table 14, the reduction of the content of panose as a substrate and the increase of the yield of glucose and cyclotetrasaccharide were found through the action of the α-isomaltosyl-transferring enzyme. Based on this, it was concluded that the α-isomaltosyl-transferring enzyme of the present invention cuts the linkage between the isomaltosyl residue of panose as a substrate and the glucose positioning at the non-reducing end of panose to release glucose from panose, and forms cyclotetrasaccharide from panose by catalyzing a reaction including isomaltosyl-transferring reaction.

Referring to the other components formed during the above reaction, three unidentified components A, B and C were detected at the initiation of reaction, i.e., one hour after the initiation of reaction. Each of the components A, the components B, and the components C in each reaction mixtures, prepared with five different enzymes, were well coincided with each other in view of their retention times on HPLC. Based on the result, each of the components A, the components B, and the components C, formed in five different reaction mixtures, were respectively identified as the same substance. Among the three components, the components A diminished in the reaction mixtures at 12 hours after the initiation of the reaction, while the components B and the components C were still remained. From these results, it can be speculated that cyclotetrasaccharide is formed from panose via the components A as an intermediate, while the components B and the components C are intermediates that are formed by the action of the enzyme of the present invention but are not easily converted into cyclotetra-saccharide.

To identify the unidentified components A, B and C, these components were respectively separated from the reaction mixture with the enzyme from Strain C9 at one hour after the initiation of the reaction using "YMC-PACK ODS-A R355-15S-15 12A", a column commercialized by YMC Co., Ltd., Tokyo, Japan, and subjected to methyl analysis (Table 15) and $^{13}$C-NMR analysis (Table 16) in a usual manner.

TABLE 15

| Methylated alditol acetate | Composition ratio (molar ratio) | | |
|---|---|---|---|
| | A | B | C |
| 2,3,4-trimethyl compound | 2.00 | 2.00 | 2.00 |
| 2,3,6-trimethyl compound | 1.00 | 2.12 | 1.00 |
| 2,4,6-tetramethyl compound | 1.03 | 0.00 | 0.00 |
| 2,3,4,6-tetramethyl compound | 0.74 | 0.81 | 1.78 |

TABLE 16

| Glucose number | Carbon number | NMR chemical shift (ppm) | | |
|---|---|---|---|---|
| | | Component A | Component B | Component C |
| a | 1a | 100.8 | 100.8 | 100.7 |
| | 2a | 74.3 | 74.4 | 74.0 |
| | 3a | 75.8 | 75.8 | 75.8 |
| | 4a | 72.3 | 72.2 | 72.2 |
| | 5a | 74.5 | 74.5 | 74.5 |
| | 6a | 63.2 | 63.2 | 63.2 |
| b | 1b | 102.5 | 102.7 | 102.7 |
| | 2b | 74.3 | 74.1 | 74.2 |
| | 3b | 75.8 | 75.8 | 75.8 |
| | 4b | 72.6 | 72.2 | 71.8 |
| | 5b | 74.0 | 74.1 | 74.2 |
| | 6b | 67.9 | 68.6 | 67.8 |

TABLE 16-continued

| Glucose number | Carbon number | NMR chemical shift (ppm) | | |
|---|---|---|---|---|
| | | Component A | Component B | Component C |
| c | 1c | 100.6 | 100.6 | 100.7 |
| | 2c | 72.8 | 74.2 | 74.0 |
| | 3c | 83.1 | 76.1 | 75.8 |
| | 4c | 72.0 | 80.1 | 72.2 |
| | 5c | 73.1 | 73.0 | 74.5 |
| | 6c | 63.0 | 63.2 | 63.2 |
| d | 1d | 102.2 | 102.7 | 102.4 |
| | 2d | 74.3 | 74.0 | 74.3 |
| | 3d | 75.8 | 75.8 | 75.8 |
| | 4d | 72.1 | 72.1 | 72.1 |
| | 5d | 74.3 | 73.9 | 74.2 |
| | 6d | 68.4 | 69.0 | 68.5 |
| e | 1e | 94.6 (α) | 94.6 (α) | 105.3 |
| | | 98.5 (β) | 98.5 (β) | |
| | 2e | 74.3 (α) | 74.3 (α) | 75.7 |
| | | 76.7 (β) | 76.7 (β) | |
| | 3e | 75.8 (α) | 75.9 (α) | 78.5 |
| | | 78.9 (β) | 78.9 (β) | |
| | 4e | 80.0 (α) | 80.3 (α) | 79.4 |
| | | 79.9 (β) | 80.1 (β) | |
| | 5e | 72.6 (α) | 72.7 (α) | 77.4 |
| | | 77.2 (β) | 77.3 (β) | |
| | 6e | 63.5 (α) | 63.6 (α) | 63.2 |
| | | 63.4 (β) | 63.6 (β) | |

Based on these results, it was revealed that the component A is a penta saccharide where an isomaltosyl residue is bound to the hydroxyl group positioning at C-3 of glucose at the non-reducing end of panose via the α-linkage, i.e., 3-O-α-isomaltosylpanose represented by the following Chemical Formula 1, and that the α-isomaltosyl-transferring enzyme of the present invention has an action of transferring an isomaltosyl residue to the hydroxyl group at C-3 of glucose positioning at the non-reducing end of panose.

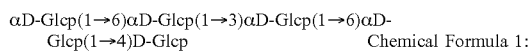
  Glcp(1→4)D-Glcp    Chemical Formula 1:

It was revealed that the component B is a penta saccharide where an isomaltosyl residue is bound to the hydroxyl group positioning at C-4 of glucose at the non-reducing end of panose via the α-linkage, i.e., 4-O-α-isomaltosylpanose represented by the following Chemical Formula 2, and that the α-isomaltosyl-transferring enzyme of the present invention has an action of transferring an isomaltosyl residue to the hydroxyl group at C-4 of glucose positioning at the non-reducing end of panose.

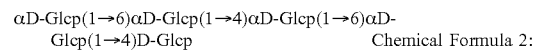
  Glcp(1→4)D-Glcp    Chemical Formula 2:

It was revealed that the component C is a penta saccharide where an isomaltosyl residue is bound to the hydroxyl group positioning at C-1 of glucose at the reducing end of panose via the α-linkage, i.e., 1-O-α-isomaltosyl-β-panoside represented by the following Chemical Formula 3, and that the α-isomaltosyl-transferring enzyme of the present invention has an action of transferring an isomaltosyl residue to the hydroxyl group at C-1 of glucose positioning at the reducing end of panose.

Chemical Formula 3:

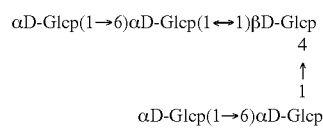

Using a purified α-isomaltosyl-transferring enzyme, the formation of cyclotetrasaccharide from the above-identified components A, B and C was examined as follows: One percent (w/v) of an aqueous solution (pH 6.0) of the component A (3-O-α-isomaltosylpanose represented by Chemical Formula 1), the component B (4-O-α-isomaltosylpanose represented by Chemical Formula 2), or the component C (1-O-α-isomaltosyl-β-panoside represented by Chemical Formula 3) was prepared into a substrate solution. To each of the resulting solutions was added one unit/g substrate of a purified specimen of α-isomaltosyl-transferring enzyme from *Bacillus globisporus* C9 obtained by the method in Experiment 4, or *Bacillus globisporus* C11 obtained by the method in Experiment 7, followed by enzymatic reaction at 35° C. for eight hours. Thereafter, the resulting mixtures were analyzed on HPLC for saccharide composition (%). The results are in Table 17.

TABLE 17

| | | Saccharide composition[*3] (%) | | | |
|---|---|---|---|---|---|
| Enzyme | Substrate[*1] | Substrate[*2] | Glucose | Cyclotetrasaccharide | Others |
| Enzyme of Strain C9 | Component A | 9.3 | 17.2 (1.00) | 67.6 (1.09) | 5.9 |
| | Component B | 77.1 | 0.7 | 5.1 | 17.1 |
| | Component C | 55.8 | 0.2 | 6.0 | 38.0 |
| Enzyme of Strain C11 | Component A | 9.0 | 17.4 (1.00) | 67.4 (1.08) | 6.2 |
| | Component B | 77.0 | 0.6 | 5.0 | 17.4 |
| | Component C | 56.0 | 0.2 | 5.9 | 37.9 |

Note:
The symbol "[*1]" shows that the component A means 3-0-α-isomaltosylpanose represented by Chemical Formula 1; the component B, 4-0-α-isomaltosylpanose represented by Chemical Formula 2; or the component C, 1-0-α-isomaltosyl-β-panoside represented by Chemical Formula 3.
The symbol "[*2]" shows that each numeral means a percentage to the total saccharide content of the remaining substrates of the components A, B and C after the enzymatic reaction.
The symbol "[*3]" means that the numeral in each parenthesis represents a molar ratio of the formed glucose and cyclotetrasaccharide.

As evident from the result in Table 17, the α-isomaltosyl-transferring enzyme of the present invention predominantly acted on the component A to form equimolar glucose and cyclotetrasaccharide. While the enzyme relatively less acted on the components B and C and formed a lesser amount of cyclotetrasaccharide than that with the component A but formed a relatively larger amount of other oligosaccharides which were estimated to be another by-products formed by the α-isomaltosyl transferring reaction. Based on these results, it was estimated that cyclotetrasaccharide was formed from panose by the action of the enzyme of the present invention via the component A as a main intermediate and partly via the components B and C.

These data concluded that the α-isomaltosyl-transferring enzyme of the present invention mainly acts on panose as follows:

(1) The enzyme acts on panose, cuts the α-1,4 glucosidic linkage between the isomaltosyl residue and the glucose positioning at the reducing end of panose, and transfers the released isomaltosyl residue either to the hydroxyl group at C-3 or C-4 of the glucose positioning at the non-reducin end of another panose through intermolecular isomaltosyl-transferring reaction, or to the hydroxyl group at C-1 of the glucose positioning at the reducing end of another panose to form 3-O-α-isomaltosylpanose (the above-identified component A with Chemical Formula 1) and 4-O-α-isomaltosylpanose (the above-identified component B with Chemical Formula 2), respectively; and (2) The enzyme also acts on the above components per se and forms cyclotetrasaccharide as a cyclic saccharide by an intramolecular cyclization reaction, for example, by acting on 3-O-α-isomaltosylpanose to cut the α-1,4 glucosidic linkage between the α-isomaltosyl-(1→3)-isomaltosyl group and the glucose positioning at the reducing end of the component A and transferring for cyclization C-1 of the glucose positioning at the reducing end of the α-isomaltosyl-(1→3)-isomaltosyl group to the hydroxyl group at C-3 of the glucose positioning at the non-reducing end of the α-isomaltosyl-(1→3)-isomaltosyl group per se.

Thus, it was revealed that the α-isomaltosyl-transferring enzyme of the present invention has two intermolecular- and intramolecular-transferring actions, where the former is an intermolecular isomaltosyl-transferring action which acts on the α-1,4 glucosidic linkage adjacent to the isomaltosyl group at the non-reducing end of panose and transfers the released isomaltosyl group either to the hydroxyl group at C-3 or C-4 of the glucose positioning at the non-reducing end of another panose, or to the hydroxyl group at C-1 of the glucose positioning at the reducing end of another panose; and the latter is an intramolecular α-isomaltosyl-transferring action which mainly acts on the α-1,4 glucosidic linkage adjacent to the α-isomaltosyl-(1→3)-isomaltosyl group and transfers intramolecularly the reducing end of the α-isomaltosyl-(1→3)-isomaltosyl group to the hydroxyl group at C-3 of the glucose positioning at the non-reducing end of the α-isomaltosyl-(1→3)-isomaltosyl group.

Based on the results in Experiments 20 and 21, it is judged that the α-isomaltosyl-transferring enzyme of the present invention acts on saccharides with a glucose polymerization degree of at least three, which have, as a bonding fashion, both the α-1,6 glucosidic linkage at the non-reducing end and the α-1,4 glucosidic linkage other than the α-1,6 glucosidic linkage.

Experiment 22

Specificity to Transferring Acceptor

Saccharides were tested as follows to examine whether they can be used as transferring acceptors for the α-isomaltosyl-transferring enzyme of the present invention. A solution of D-glucose, D-xylose, L-xylose, D-galactose, D-fructose, D-mannose, D-arabinose, D-fucose, L-sorbose, L-rhamnose, methyl-α-glucoside (or methyl-α-glucopyranoside), methyl-β-glucoside (or methyl-β-glucopyranoside), N-acetyl-D-glucosamine, D-ribose, L-ribose, D-psicose, sorbitol, xylitol, mannitol, arabitol, ribitol, erythritol, maltose, maltotriose, maltotetraose, maltopentaose, isomaltose, isomaltotriose, α,α-trehalose, α,β-trehalose, kojibiose, nigerose, cellobiose, gentibiose, isopanose, maltitol, maltotriitol, lactose, sucrose, erlose, isomaltosylglucoside, α-cyclodextrin, β-cyclodextrin, γ-cyclodextrin, or L-ascorbic acid was prepared. To each solution was added panose as a saccharide donor to give an equal concentration, admixed with 10 units/g substrate of a purified specimen of either α-isomaltosyl-transferring enzyme from *Bacillus globisporus* C9 obtained by the method in Experiment 4, *Bacillus globisporus* C11 obtained by the method in Experiment 7, *Bacillus globisporus* N75 obtained by the method in Experiment 11, or *Arthrobacter ramosus* S1 obtained by the method in Experiment 15, or a partially purified specimen of α-isomaltosyl-transferring enzyme from *Arthrobacter globiformis* A19 obtained by the method in Experiment 18, followed by adjusting the saccharide concentration to 3.2% (w/v). The mixtures thus obtained were enzymatically reacted at 30° C. and Ph 6.0 for 24 hours. The saccharide composition of the resulting reaction mixtures were analyzed on gas chromatography (abbreviated as "GLC" hereinafter) for monosaccharides and disaccharides as testing saccharides, and on HPLC for tri- or higher-saccharides as testing saccharides to confirm whether these saccharides can be used as transferring acceptors for the above enzymes with an index of the positive or negative formation of a saccharide transferred product. In performing GLC, the following apparatuses and conditions were used: GLC apparatus, "GC-16A" commercialized by Shimadzu Corporation, Tokyo, Japan; column, a stainless-steel column, 3 mm in diameter and 2 m in length, packed with 2% "SILICONE OV-17/CHROMOSOLV W", commercialized by GL Sciences Inc., Tokyo, Japan; carrier gas, nitrogen gas at a flow rate of 40 ml/min under temperature conditions of increasing from 160° C. to 320° C. at an increasing temperature rate of 7.5° C./min; and detection, a hydrogen flame ionization detector. In the case of HPLC analysis, the apparatuses and conditions used were: HPLC apparatus, "CCPD" commercialized by Tosoh Corporation, Tokyo, Japan; column, "ODS-AQ-303" commercialized by YMC Co., Ltd., Tokyo, Japan; eluent, water at a flow rate of 0.5 ml/min; and detection, a differential refractometer. The results are in Table 18.

TABLE 18

| Saccharide | Product of transferring reaction | | | | |
|---|---|---|---|---|---|
| | Enzyme of Strain C9 | Enzyme of Strain C11 | Enzyme of Strain N75 | Enzyme of Strain S1 | Enzyme of Stain A19 |
| D-Glucose | ++ | ++ | ++ | ++ | ++ |
| D-Xylose | ++ | ++ | ++ | ++ | ++ |
| L-Xylose | ++ | ++ | ++ | ++ | ++ |
| D-Galactose | − | − | − | + | ± |
| D-Fructose | − | − | − | + | ± |
| D-Mannose | − | − | − | − | − |
| D-Arabinose | ± | ± | ± | + | ± |
| D-Fucose | ± | ± | ± | + | ± |
| L-Sorbose | + | + | + | + | + |
| L-Rhamnose | ± | ± | ± | + | ± |
| Methyl-α-glucoside | ++ | ++ | ++ | ++ | ++ |
| Methyl-β-glucoside | ++ | ++ | ++ | + | + |
| N-Acetyl-glucosamine | − | − | − | − | − |
| D-Ribose | − | − | − | + | ± |
| L-Ribose | − | − | − | ++ | ± |
| D-Psicose | − | − | − | ± | ± |
| Sorbitol | − | − | − | ± | ± |
| Xylitol | − | − | − | ± | ± |
| Mannitol | − | − | − | − | − |
| Arabitol | − | − | − | ± | − |
| Ribitol | − | − | − | ± | − |
| Erythritol | + | + | + | + | ± |
| Maltose | + | + | + | + | + |
| Maltotriose | + | + | + | ++ | + |
| Maltotetraose | + | + | + | + | + |
| Maltopentaose | + | + | ± | ± | + |
| Isomaltose | ++ | ++ | ++ | ++ | ++ |
| Isomaltotriose | + | + | + | ++ | + |
| α,α-Trehalose | + | + | + | + | + |
| Neotrehalose | ++ | ++ | ++ | ++ | ++ |
| Kojibiose | + | + | + | + | + |
| Nigerose | + | + | + | + | + |
| Cellobiose | + | + | + | + | + |
| Gentibiose | ++ | ++ | ++ | + | + |
| Isopanose | + | + | + | + | + |
| Maltitol | + | + | + | + | + |
| Maltotriitol | + | + | + | + | + |
| Lactose | + | + | + | + | + |
| Sucrose | + | + | + | + | + |
| Erlose | + | + | + | + | + |
| Isomaltosylglucoside | ++ | ++ | ++ | ++ | ++ |
| α-Cyclodextrin | − | − | − | − | − |
| β-Cyclodextrin | − | − | − | − | − |
| γ-Cyclodextrin | − | − | − | − | − |
| L-Ascorbic acid | ++ | ++ | ++ | ++ | + |

Note:
In the table, the symbols "−", "±", "+", and "++" mean that no saccharide transferred product was formed, a saccharide-transferred product formed in an amount of less than one percent to the total sugars, a saccharide-transferred product was formed in an amount of over one percent but below 10% to the total sugars, and a saccharide-transferred product was formed in an amount of over 10% to the total sugars, respectively.

As evident from the results in Table 18, it was revealed that the α-isomaltosyl-transferring enzyme of the present invention acts on different types of saccharides as transfer acceptors; the α-isomaltosyl-transferring enzymes from Strains C9, C11 and N75 advantageously transfer, particularly, to D-glucose, D-/L-xylose, methyl-α-glucoside, methyl-β-glucoside, isomaltose, neotrehalose, gentibiose, isomaltosylglucoside, and L-ascorbic acid; next to L-sorbose, maltose, trehalose, kojibiose, nigerose, cellobiose, lactose, sucrose, maltotriose, isomaltotriose, isopanose, erlose, maltotetraose, maltopentaose, erythritol, maltitol, and maltotriitol; and then to D-arabinose, D-fucose, and L-rhamnose. It was revealed that the above enzyme from *Arthrobacter ramosus* S1 well transfers, particularly, to D-glucose, D-/L-xylose, methyl-α-glucoside, L-ribose, iso- maltose, neotrehalose, maltotriose, isomaltotriose, isomaltosylglucoside, and L-ascorbic acid; next to D-galactose, D-fructose, D-arabinose, D-fucose, L-sorbose, L-rhamnose, methyl-β-glucoside, D-ribose, maltose, trehalose, kojibiose, nigerose, cellobiose, gentibiose, lactose, sucrose, isopanose, erlose, maltotetraose, erythritol, maltitol, and maltotriitol; and then to D-psicose, maltopentaose, sorbitol, xylitol, arabitol, and ribitol. While the above enzyme from *Arthrobacter globiformis* A19 well transfers, particularly, to D-glucose, D-/L-xylose, methyl-α-glucoside, isomaltose, neotrehalose, and isomaltosylglucoside; next to L-sorbose, methyl-β-glucoside, maltose, maltotriose, maltotetraose, maltopentaose, isomaltotriose, trehalose, kojibiose-, nigerose, cellobiose, gentibiose, isopanose, maltitol, maltotriitol, lactose, sucrose, erlose, and L-ascorbic acid; and then to D-galactose, D-fructose, D-arabinose, D-fucose, L-rhamnose, D-ribose, L-ribose, D-psicose, sorbitol, xylitol, and erythritol.

Among the α-isomaltosyl-transferring enzymes according to the present invention, the properties of these enzymes in a purified form were compared with those of a previously reported alternanase, a hydrolyzing enzyme, that forms a cyclic tetrasaccharide from alternan, disclosed in "*European Journal of Biochemistry*", Vol. 226, pp. 633–639 (1994). The results are in Table 19.

TABLE 19

|  | α-Isomaltosyl-transferring enzyme | | | | |
| --- | --- | --- | --- | --- | --- |
| Property | Strain C9 | Strain C11 | Strain N75 | Strain S1 | Alternanase |
| Type of enzyme | Transferring enzyme | Transferring enzyme | Transferring enzyme | Transferring enzyme | Hydrolase |
| Isoelectric point (pI) | 5.5 ± 0.5 | 5.6 ± 0.5 | 7.8 ± 0.5 | 4.2 ± 0.5 | About 4 |
| Optimum pH | About 6.0 | About 5.5–6.0 | About 6.0 | About 6.0 | About 7 |
| Activation by $Ca^{2+}$ | Negative | Negative | Negative | Negative | Positive |
| Inhibition by $Fe^{2+}$, $Mn^{2+}$, or EDTA | Negative | Negative | Negative | Negative | Positive |
| Hydrolysis of soluble starch or pullulan | Negative | Negative | Negative | Negative | Slight but detectable |

As evident from Table 19, the α-isomaltosyl-transferring enzyme of the present invention is a novel enzyme having properties completely different from alternanase.

Experiment 23

Preparation of Cyclotetrasaccharide

About 100 L of a 4% (w/v) aqueous panose solution was prepared using panose commercialized by Hayashibara Biochemical Laboratories, Inc., Okayama, Japan, adjusted to pH 6.0 and 30° C., and then admixed with two units/g panose of a purified enzyme specimen of α-isomaltosyl-transferring enzyme obtained by the method in Experiment 7, followed by incubating the mixture for 48 hours and heating the resulting mixture at 100° C. for 10 min to inactivate the remaining enzyme. Thereafter, a portion of the reaction mixture was sampled and then quantified on HPLC for determining the formation yield of cyclotetrasaccharide, revealing that it contained about 44% cyclotetrasaccharide, on a saccharide composition basis. Similarly as in Experiment 1, the reaction mixture was adjusted to pH 5.0 and 45° C., and then treated for 24 hours with 1,500 units/g solids of α-glucosidase and 75 units/g solids of "GLUCOZYME", a glucoamylase commercialized by Nagase Biochemicals, Ltd., Kyoto, Japan, to hydrolyze the remaining reducing oligosaccharides, etc. The resulting mixture was adjusted to pH 5.8 by the addition of sodium hydroxide and then incubated at 90° C. for one hour to inactivate the remaining enzymes and filtered to remove insoluble substances. The filtrate was concentrated using a reverse osmosis membrane to give a concentration of about 16%, d.s.b., and the concentrate was in a usual manner decolored, desalted, filtered, and concentrated to obtain about 6.1 kg of a saccharide solution containing about 3,650 g solids. The saccharide solution was fed to a column packed with about 225 L of "AMBERLITE CR-1310 (Na-form)", an ion-exchange resin commercialized by Japan Organo Co., Ltd., Tokyo, Japan, and chromatographed at a column temperature of 60° C. and a flow rate of about 45 L/h. While the saccharide composition of the eluate from the column was monitored by HPLC as described in Experiment 1, fractions with at least 98% pure cyclotetrasaccharide were collected, and then in a usual manner decolored, desalted, filtered, and concentrated to obtain about 3 kg of a saccharide solution containing about 1,000 g solids. HPLC measurement for saccharide composition of the saccharide solution revealed that it contained about 99.2% pure cyclotetrasaccharide.

Experiment 24

Crystallization of Cyclotetrasaccharide in Aqueous Solution

Figure 25:
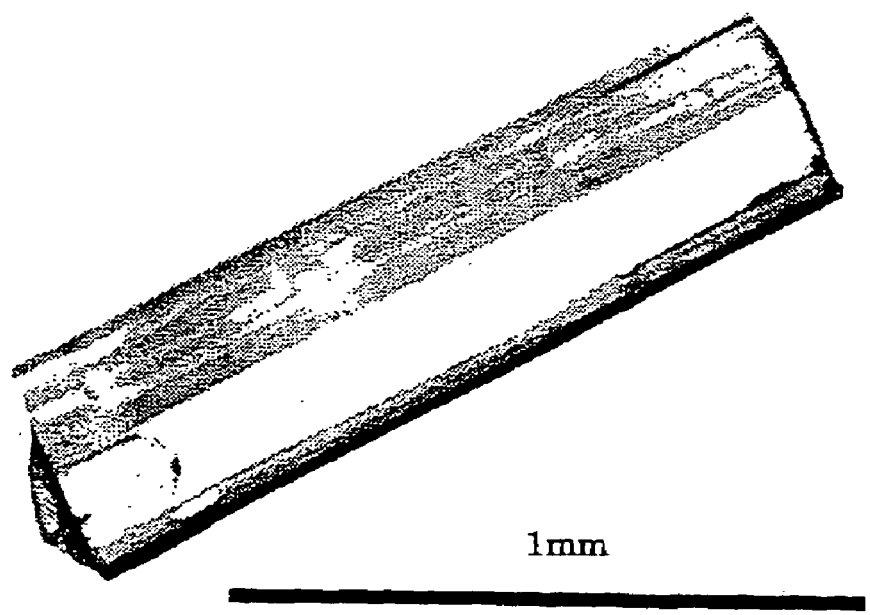
FIG. 25 is a visualized intermediate image, displayed on a screen, of a microscopic photo for the cyclotetrasaccharide crystal, penta- to hexa-hydrate, in a crystalline powdery form, obtained by the α-isomaltosyl-transferring enzymatic reaction according to the present invention.

An aqueous cyclotetrasaccharide solution, obtained by the method in Experiment 23, was concentrated by an evaporator into an about 50%, d.s.b., solution. About two kilograms of the concentrate was placed in a cylindrical plastic vessel and then crystallized by lowering the temperature of the concentrate from 65° C. to 20° C. over about 20 hours under gentle rotatory conditions, and then dried to obtain a white crystalline powder. FIG. 25 is an image of a microscopic photograph of the powder. The above crystallized concentrate was separated with a centrifugal filter to obtain 542 g of a crystalline product by wet weight, which was further dried at 60° C. for three hours to obtain 456 g of a crystalline cyclotetrasaccharide powder. HPLC measurement of the powder revealed that it contained cyclotetrasaccharide with an extremely high purity of 99.9% or higher.

Figure 26:
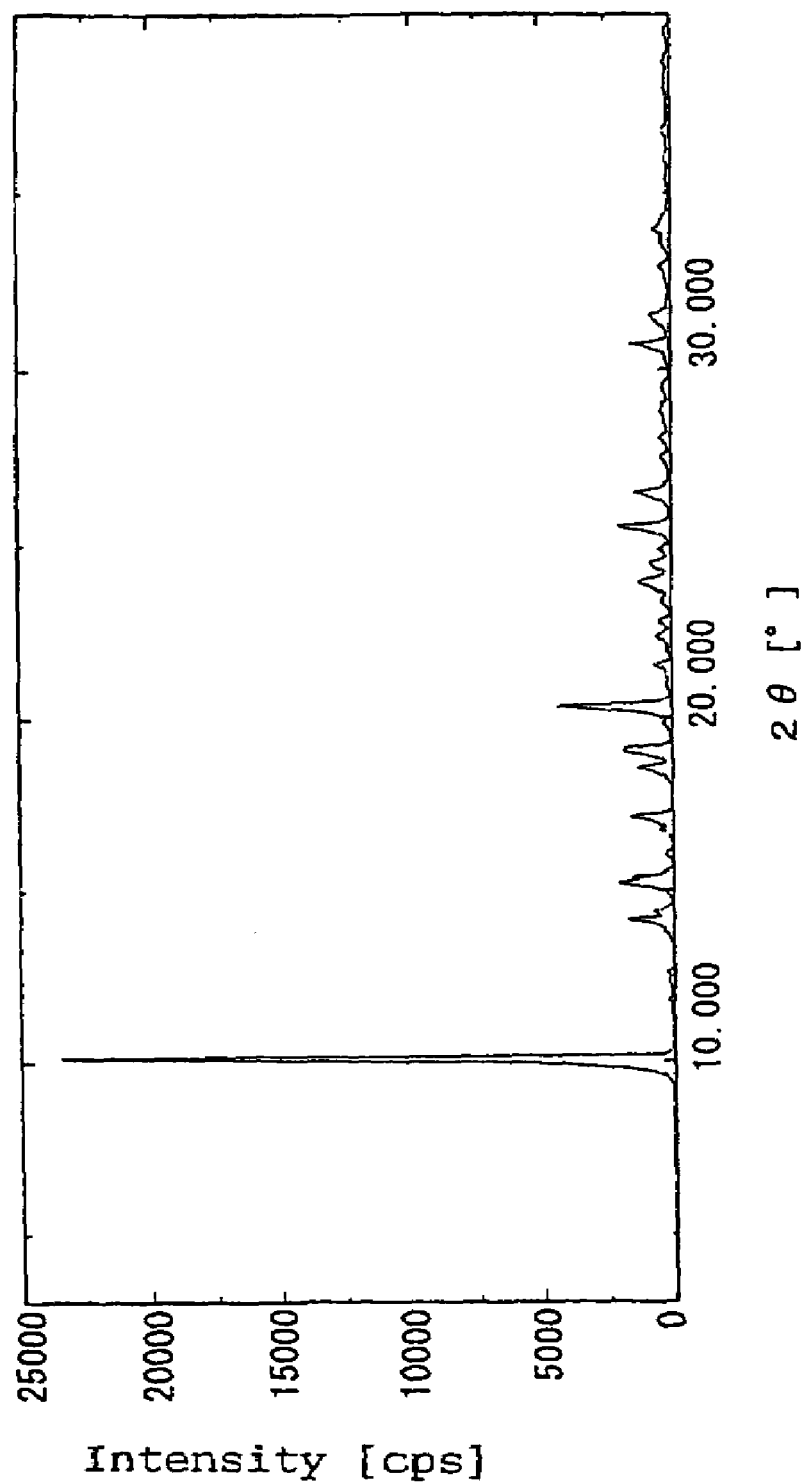
FIG. 26 is an x-ray diffraction spectrum for the cyclotetrasaccharide, penta- to hexa-hydrate, in a crystalline powdery form, obtained by the α-isomaltosyl-transferring enzymatic reaction according to the present invention, when determined on x-ray powder diffraction analysis.

When analyzed on powder x-ray diffraction analysis, the cyclotetrasaccharide in a crystalline powder form had a diffraction spectrum having characteristic main diffraction angles (2θ) of 10.1°, 15.2°, 20.3°, and 25.5° in FIG. 26. The Karl Fischer method of the crystalline powder revealed that it had a moisture content of 13.0% and that it was a crystal of cyclotetrasaccharide having five to six moles of water per one mole of the cyclotetrasaccharide.

Figure 27:
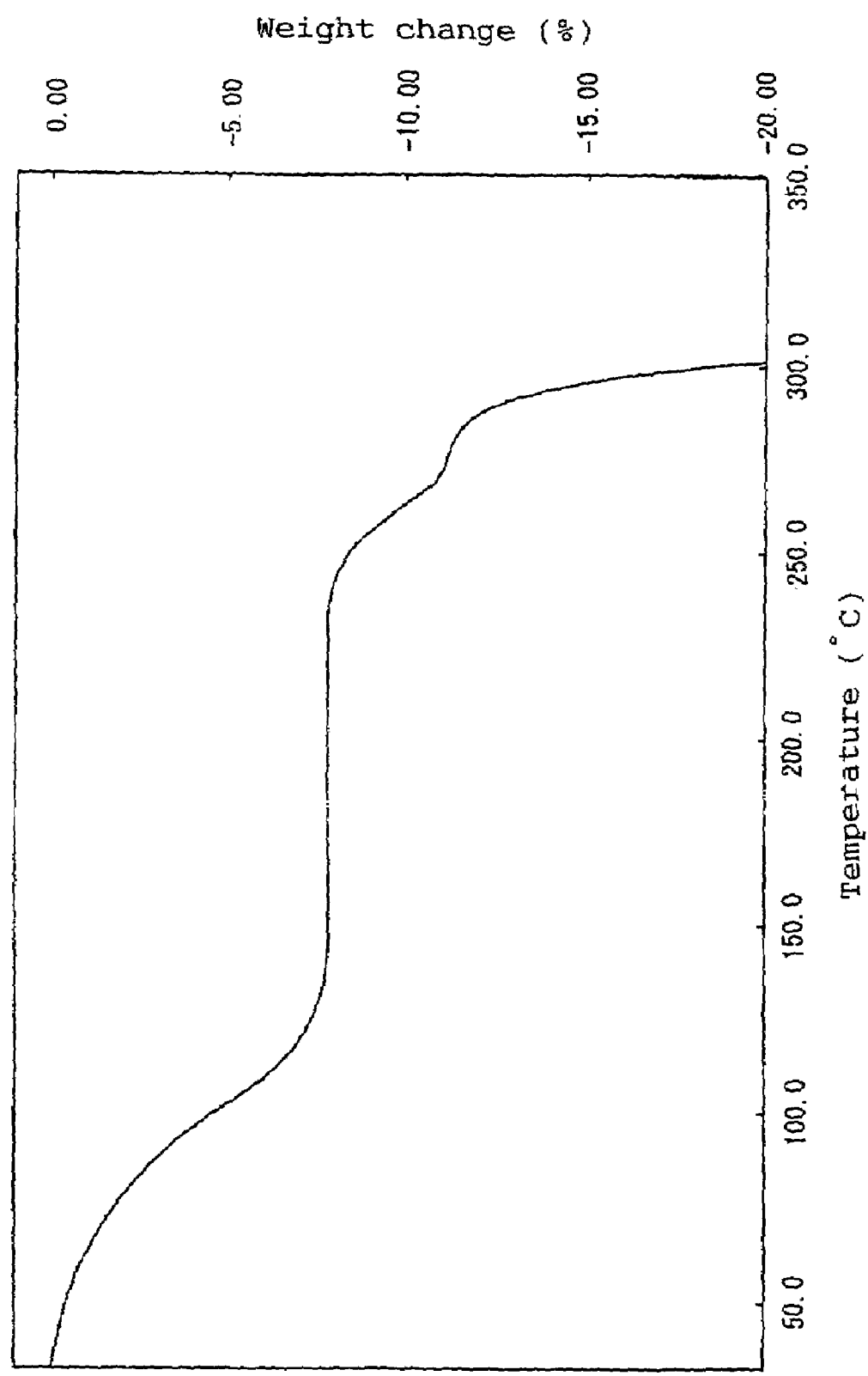
FIG. 27 is a thermogravimetric curve for the cyclotetrasaccharide, penta- to hexa-hydrate, in a crystalline powdery form, of the present invention, when determined on thermogravimetric analysis.

The thermogravimetric analysis of the cyclotetrasaccharide in a crystalline powder form gave a thermogravimetric curve in FIG. 27. Based on the relationship between the weight change and the temperature, it was successively found that the weight reduction corresponding to four to five moles of water was observed when heated up to a temperature of 150° C., the weight reduction corresponding to one mole of water at around 250° C., and the weight reduction corresponding to the decomposition of cyclotetrasaccharide at a temperature of about 280° C. or higher. These results confirmed that the cyclotetrasaccharide crystal, penta- to hexa-hydrate, of the present invention releases four to five moles of water to change into a monohydrate crystal when heated up to 150° C. at normal pressure, and further releases one mole of water to change into an anhydrous crystal at a temperature around 250° C.

Experiment 25

Conversion into Cyclotetrasaccharide, Monohydrate

Figure 28:
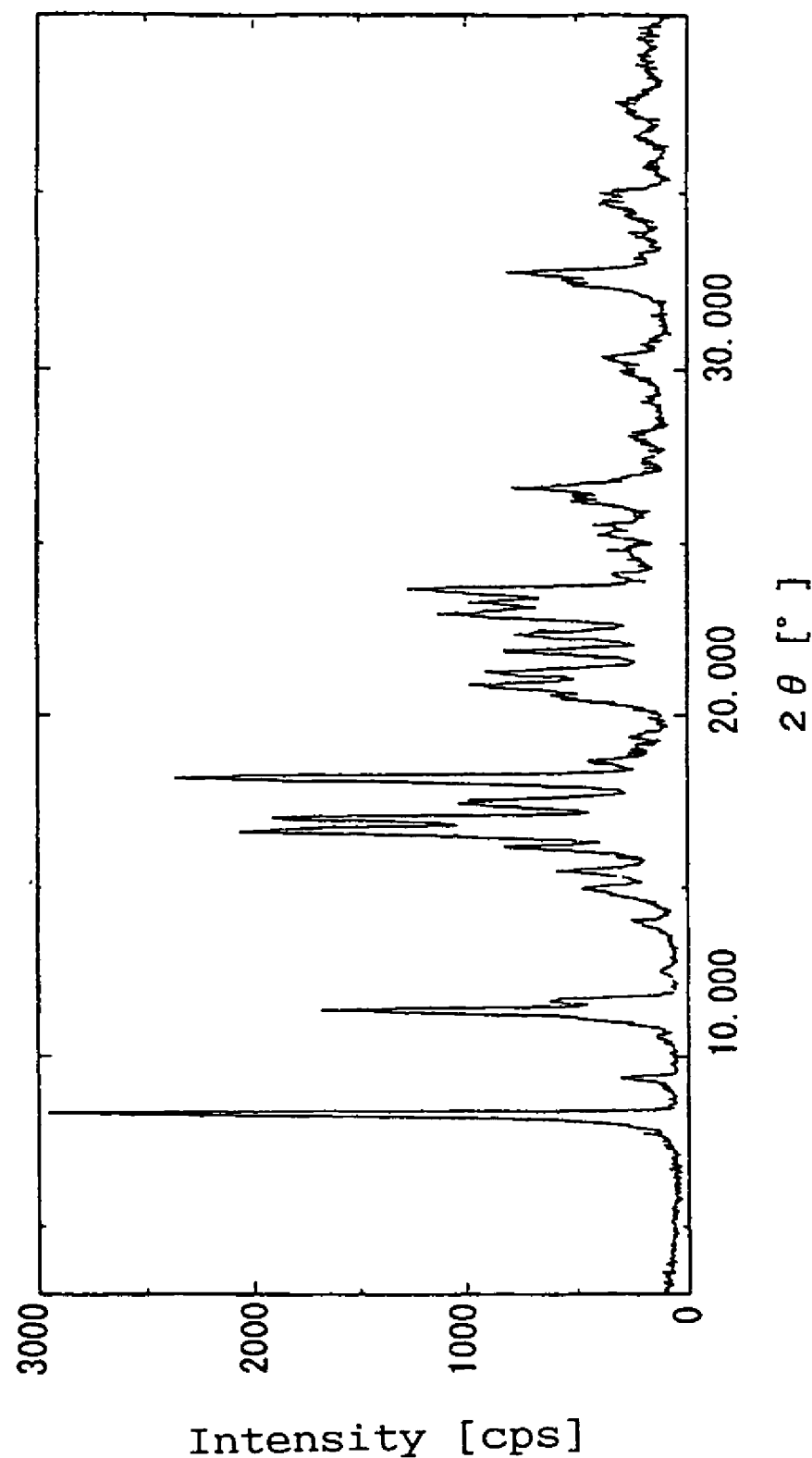
FIG. 28 is an x-ray diffraction spectrum for the cyclotetrasaccharide, monohydrate, in a crystalline powdery form, according to the present invention, when determined on x-ray powder diffraction analysis.
Figure 29:
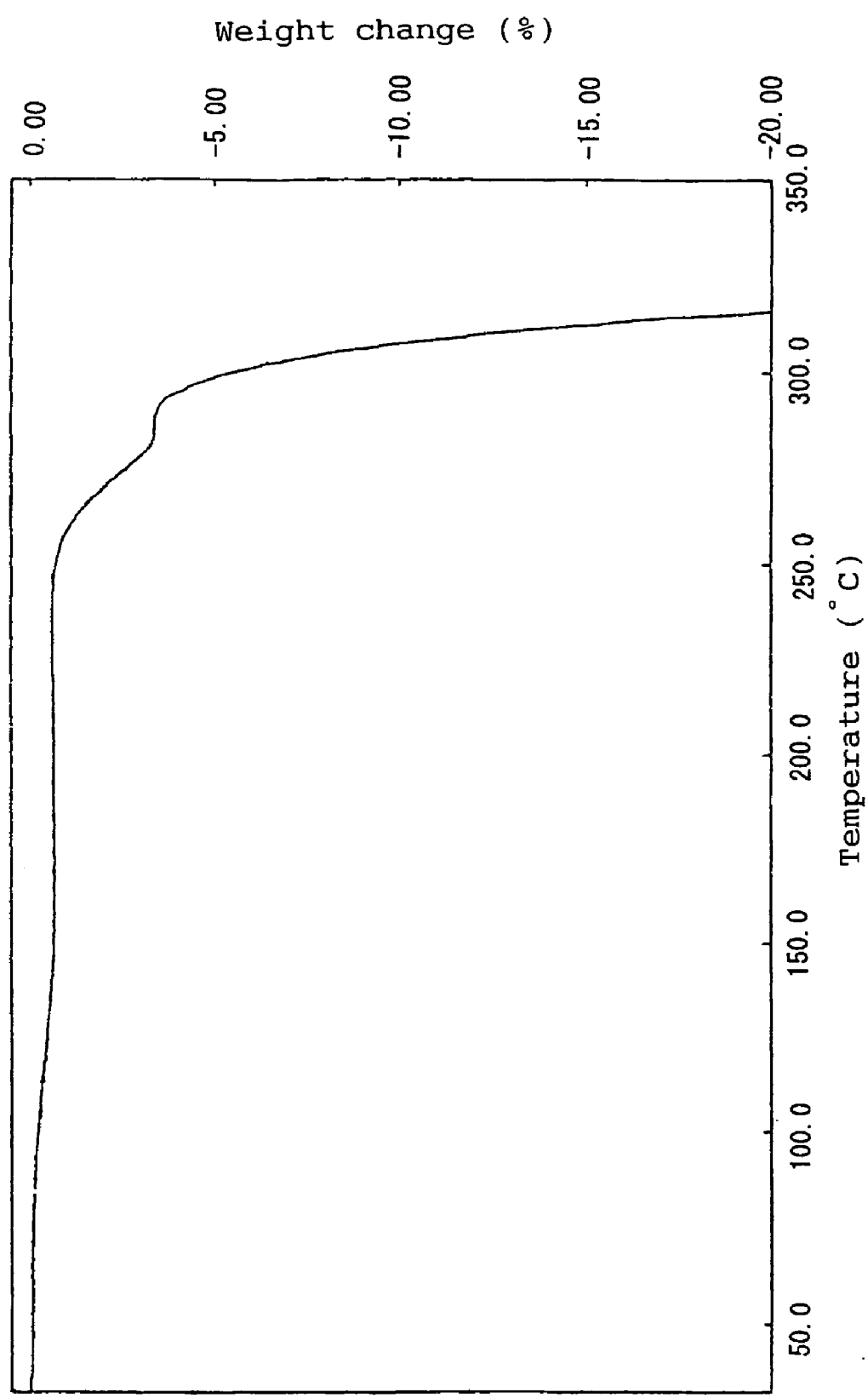
FIG. 29 is a thermogravimetric curve for the cyclotetrasaccharide, monohydrate, in a crystalline powdery form, according to the present invention, when determined on thermogravimetric analysis.

Cyclotetrasaccharide, penta- to hexa-hydrate, in a crystalline powder form, obtained by the method in Experiment 24, was placed in a glass vessel, and kept in an oil bath, which had been preheated at 140° C. for 30 min. Unlike quite different from the result from the powder x-ray diffraction analysis of the intact cyclotetrasaccharide, penta- to hexa-hydrate, the powder x-ray analysis of the cyclotetrasaccharide powder thus obtained gave a characteristic diffraction spectrum having main diffraction angles ($2\theta$) of 8.3°, 16.6°, 17.0°, and 18.2° in FIG. 28. The Karl Fischer method of the crystalline power revealed that it had a moisture content of about 2.7% and was a crystal of cyclotetrasaccharide having one mole of water per one mole of the cyclotetrasaccharide. The thermogravimetric analysis of the cyclotetrasaccharide in a crystalline powder form gave a thermogravimetric curve in FIG. 29. Based on the relationship between weight change and temperature, the weight reduction corresponding to one mole of water was observed at a temperature of about 270° C. and further the weight reduction corresponding to the decomposition of cyclotetrasaccharide per se was observed at a temperature of about 290° C. or higher. These results confirmed that the cyclotetrasaccharide crystal in this experiment was cyclotetrasaccharide, monohydrate.

Experiment 26

Conversion into Anhydrous Crystal

Figure 30:
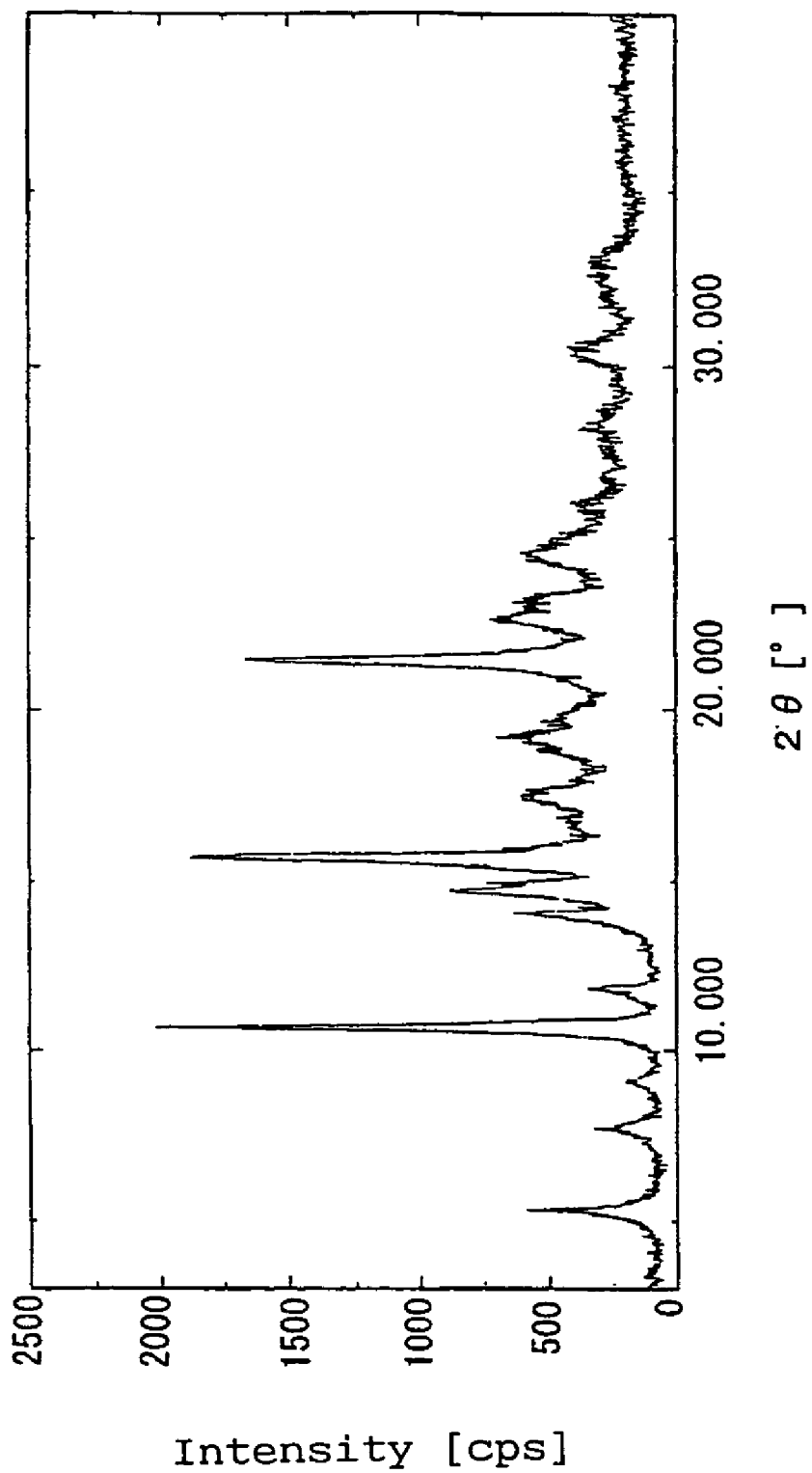
FIG. 30 is an x-ray diffraction spectrum for an anhydrous crystalline powder of cyclotetrasaccharide, obtained by drying the cyclotetrasaccharide, penta- to hexa-hydrate, according to the present invention, in vacuo at 40° C., when determined on x-ray powder diffraction analysis.
Figure 31:
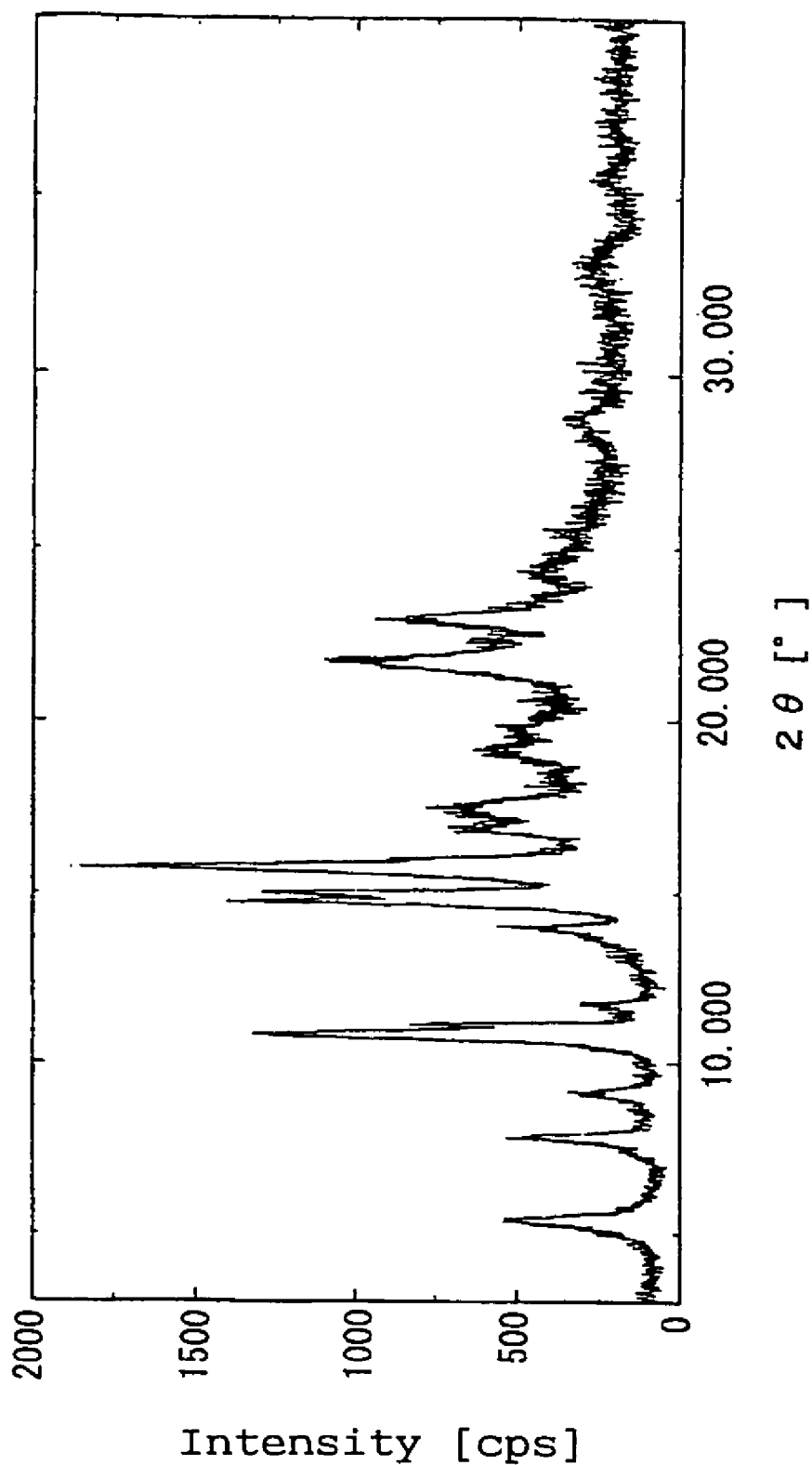
FIG. 31 is an x-ray diffraction spectrum for an anhydrous crystalline powder of cyclotetrasaccharide, obtained by drying the cyclotetrasaccharide, penta- to hexa-hydrate, according to the present invention in vacuo at 120° C., when determined on x-ray powder diffraction analysis.

Cyclotetrasaccharide, penta- to hexa-hydrate, in a crystalline powder form, obtained by the method in Experiment 24, was dried in vacuo at 40° C. or 120° C. for 16 hours. The Karl Fischer method of the resulting crystalline powders revealed that the one dried at 40° C. had a moisture content of about 4.2%, and the other dried at 120° C. had a moisture content of about 0.2%, meaning that the latter was substantially anhydrous. Unlike quite different from the results of powder x-ray diffraction analyses for the cyclotetrasaccharide, penta- to hexa-hydrate, and the cyclotetrasaccharide, monohydrate, before drying in vacuo, the powder x-ray analysis of the above cyclotetrasaccharides dried in vacuo at 40° and 120° C. gave characteristic diffraction spectra having main diffraction angles ($2\theta$) of 10.8°, 14.7°, 15.0°, 15.7°, and 21.5° in FIG. 30 for the specimen dried in vacuo at 40° C. and FIG. 31 for the specimen dried in vacuo at 120° C. Although there was found difference in peak levels between the two diffraction spectra, they had substantially the same peak diffraction angles and were crystallographically judged to be the same anhydrous crystalline. The base lines of the diffraction spectra exhibited a mountain-like pattern and the crystallinity of the anhydrous crystalline was lower than those of cyclotetrasaccharide, penta- to hexa-hydrate, and cyclotetrasaccharide, monohydrate, before being dried in vacuo, and the fact revealed that an amorphous cyclotetrasaccharide was present. Based on this, the cyclotetrasaccharide powder with a moisture content of about 4.2%, obtained by drying in vacuo at 40° C., was estimated to be a mixture powder of an amorphous cyclotetrasaccharide with the above moisture content and an anhydrous crystalline cyclotetrasaccharide.

Figure 32:
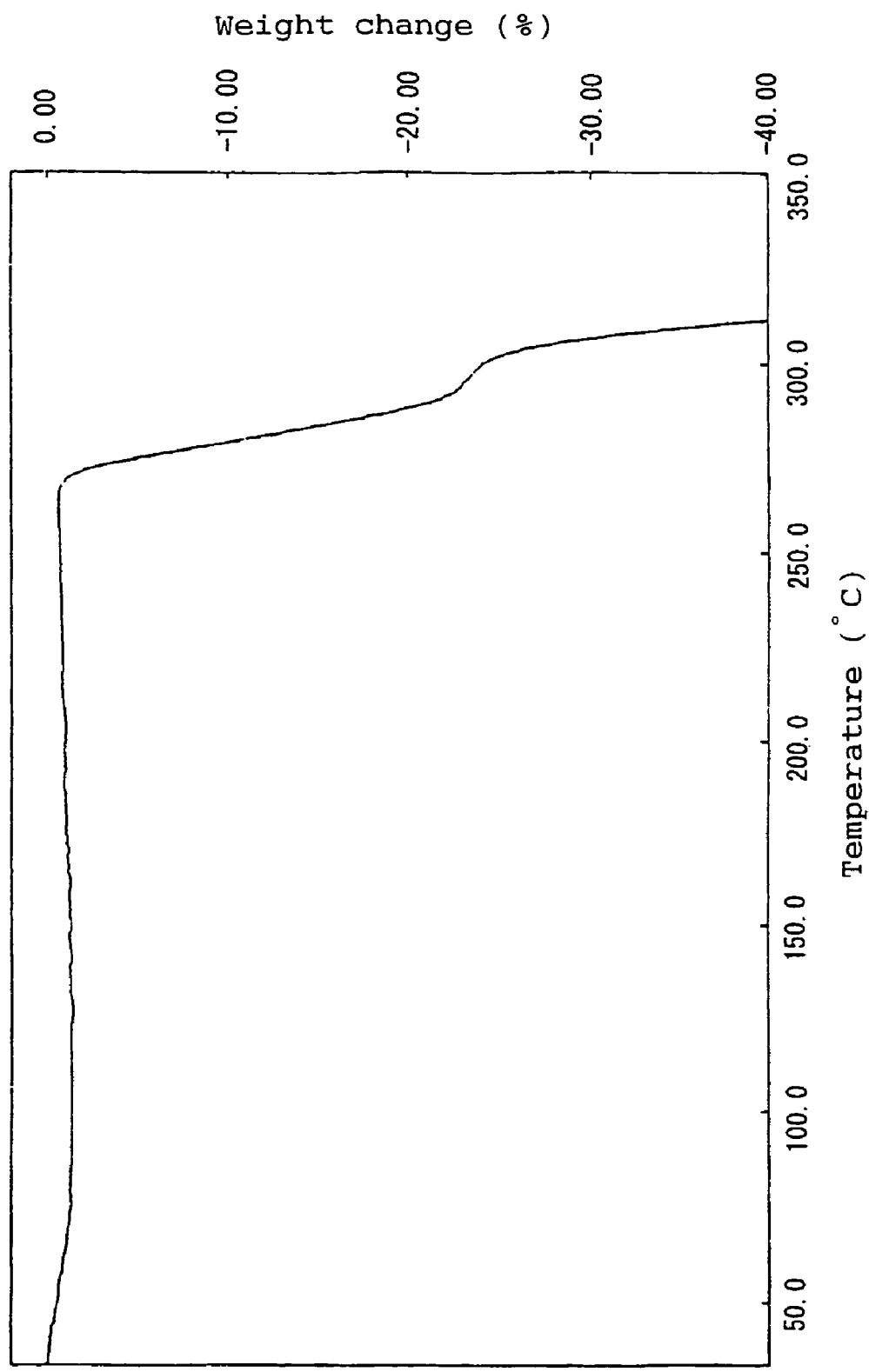
FIG. 32 is a thermogravimetric curve for the anhydrous cyclotetrasaccharide powder according to the present invention, when determined on thermogravimetric analysis.

These data revealed that cyclotetrasaccharide, penta- to hexa-hydrate, was converted into those in an amorphous- and anhydrous-forms when dehydrated by drying in vacuo. When subjected to thermogravimetric analysis similarly as in Experiment 24, the anhydrous cyclotetrasaccharide with a moisture content of 0.2% showed only the weight reduction deemed to be responsible for heat decomposition at a temperature of about 270° C. or higher in FIG. 32.

Experiment 27

Saturation Concentration of Cyclotetrasaccharide in Water

To examine the saturation concentration of cyclotetrasaccharide in water at temperatures of 10–90° C., 10 ml aliquots of water were respectively placed in glass vessels with a seal cap, and then mixed with cyclotetrasaccharide, penta- to hexa-hydrate, obtained by the method in Experiment 24, in an excessive amount over a level that dissolves completely at respective temperatures, cap-sealed, and stirred for two days while keeping at respective temperatures of 10–90° C. until being saturated. The resulting each saturated solution of cyclotetrasaccharide was membrane filtered to remove undissolved cyclotetrasaccharide, and each filtrate was then examined for moisture content by the drying loss method and determined for a saturation concentration of cyclotetrasaccharide at respective temperatures. The results are in Table 20.

TABLE 20

| Temperature (° C.) | Saturation concentration of cyclotetrasaccharide (%) | Weight of cyclotetrasaccharide dissolved in 100 g water (g) |
| --- | --- | --- |
| 10 | 30.3 | 43.5 |
| 30 | 34.2 | 51.9 |
| 50 | 42.6 | 74.2 |
| 70 | 53.0 | 112.7 |
| 90 | 70.5 | 239.0 |

Experiment 28

Thermostability

A crystalline cyclotetrasaccharide, penta- to hexa-hydrate, obtained by the method in Experiment 24, was dissolved in water into a 10% (w/v) aqueous solution of cyclotetrasaccharide, and eight milliliters of which was placed in a glass test tube, followed by sealing the test tube and heating the aqueous solution at 120° C. for 30–90 min. After the heating, the aqueous solution was cooled under atmospheric conditions and measured for coloration degree and determined for purity on HPLC in Experiment 1. The coloration degree was evaluated based on the absorbance in a cell with a 1-cm light pass at a wavelength of 480 nm. The results are in Table 21.

TABLE 21

| Heating time (min) | Coloration degree ($A_{480\ nm}$) | Purity (%) |
| --- | --- | --- |
| 0 | 0.00 | 100 |
| 30 | 0.00 | 100 |
| 60 | 0.00 | 100 |
| 90 | 0.00 | 100 |

As evident from the results in Table 21, it was revealed that cyclotetrasaccharide is a thermostable saccharide because an aqueous solution of cyclotetrasaccharide was not colored and the purity in the saccharide composition was not lowered even when heated at a high temperature of 120° C.

Experiment 29 pH Stability

A crystalline cyclotetrasaccharide, penta- to hexa-hydrate, obtained by the method in Experiment 24, was dissolved in 20 mM buffers with different pHs into 4% (w/v) cyclotetrasaccharide solutions with a pH of 2–10. Eight milliliters of each solution was placed in a glass test tube, followed by sealing the test tube and heating the solution at 100° C. for 24 hours. After cooling under atmospheric conditions, each solution was measured for coloration degree and determined for purity on HPLC. The coloration degree was evaluated based on the absorbance in a cell with a 1-cm light pass at a wavelength of 480 nm. The results are in Table 22.

TABLE 22

| pH (Buffer) | Coloration degree ($A_{480\ nm}$) | Purity (%) |
|---|---|---|
| 2.0 (Acetate buffer) | 0.00 | 93 |
| 3.0 (Acetate buffer) | 0.00 | 100 |
| 4.0 (Acetate buffer) | 0.00 | 100 |
| 5.0 (Acetate buffer) | 0.00 | 100 |
| 6.0 (Tris-HCl buffer) | 0.00 | 100 |
| 7.0 (Tris-HCl buffer) | 0.00 | 100 |
| 8.0 (Tris-HCl buffer) | 0.00 | 100 |
| 9.0 (Ammonium buffer) | 0.00 | 100 |
| 10.0 (Ammonium buffer) | 0.00 | 100 |

As evident from the results in Table 22, an aqueous solution of cyclotetrasaccharide was not colored even when heated at 120° C. for 24 hours in a wide pH range from 2 to 10, and the purity in the saccharide composition did not lower at all in a pH range from pH 3 to pH 10, even though the purity lowered slightly at pH 2. These facts revealed that cyclotetrasaccharide was highly stable in a relatively wide pH range, i.e., an acid pH range from pH 3 to pH 5, a neutral pH range from pH 6 to pH 8, and an alkaline pH range from pH 9 to pH 10.

Experiment 30

Amino Carbonyl Reaction

A crystalline cyclotetrasaccharide, penta- to hexa-hydrate, obtained by the method in Experiment 24, was dissolved in water, and then admixed with a commercialized special grade glycine and phosphate buffer, and the resulting mixture was then adjusted to pH 7.0 with 50 mM phosphate buffer to obtain a 10% (w/v) cyclotetrasaccharide solution containing 1% (w/v) glycine. Four milliliter aliquots of the resulting solution were placed in glass test tubes, sealed, and heated at 100° C. for 30 to 90 min. After allowing to stand for cooling at ambient temperature, each of the resulting solutions was measured for coloration degree to examine their amino carbonyl reactivity. The coloration degree was evaluated based on the absorbance in a cell with 1-cm light pass at a wavelength of 480 nm. The results are in Table 23.

TABLE 23

| Heating time (min) | Coloration degree ($A_{480\ nm}$) |
|---|---|
| 0 | 0.00 |
| 30 | 0.00 |
| 60 | 0.00 |
| 90 | 0.00 |

As evident from the results in Table 23, cyclotetrasaccharide was not colored even when heated in the presence of glycine, meaning that the saccharide does not induce browning with glycine, i.e., cyclotetrasaccharide is a stable saccharide which does not substantially induce the amino carbonyl reaction, alias the Maillard reaction.

Experiment 31

Amino Carbonyl Reaction

A crystalline cyclotetrasaccharide, penta- to hexa-hydrate, obtained by the method in Experiment 24, and a commercialized polypeptone, Nihonseiyaku K.K., Tokyo, Japan, were dissolved in deionized water to obtain a 10% (w/v) cyclotetrasaccharide solution containing 5% (w/v) polypeptone. Four milliliter aliquots of the resulting solution were placed in glass test tubes, sealed, and heated at 120° C. for 30 to 90 min. After allowing to stand for cooling at ambient temperature, each of the resulting solution was measured for coloration degree to examine their amino carbonyl reactivity. In parallel, as a control, a solution with only polypeptone was provided and similarly treated as above. The coloration degree was evaluated based on the level of the absorbance, measured in a cell with 1-cm light pass at a wavelength of 480 nm, minus that of the control. The results are in Table 24.

TABLE 24

| Heating time (min) | Coloration degree ($A_{480\ nm}$) |
|---|---|
| 0 | 0.00 |
| 30 | 0.00 |
| 60 | 0.00 |
| 90 | 0.00 |

As evident from the results in Table 24, it was revealed that cyclotetrasaccharide did not induce browning with polypeptone when heated in the presence of polypeptone, i.e., the saccharide is a stable saccharide which does not substantially induce the amino carbonyl reaction.

Experiment 32

Inclusion Action

A crystalline cyclotetrasaccharide, penta- to hexa-hydrate, obtained by the method in Experiment 24, was dissolved in deionized water to obtain a 20% (w/v) aqueous solution of cyclotetrasaccharide. To 100 g of the aqueous solution was added 2 g of methanol, 3 g of ethanol, or 4.6 g of acetic acid to be included by the cyclotetrasaccharide. Thereafter, each of the resulting solutions was filtered to remove non-inclusion products, and the filtrate was lyophilized. As a control, similar inclusion products were prepared by using "ISOELITE™ P", a branched cyclodextrin commercialized by Maruha K.K., Tokyo, Japan, known to have inclusion ability.

To measure the amount of the inclusion products in the resulting lyophilized powders, one gram of each powder was dissolved in five milliliters water and extracted after admixing with five milliliters of diethylether. The extraction was repeated, and the resulting extracts were pooled and quantified on gas chromatography. The results are in Table 25.

TABLE 25

| Inclusion product | Inclusion amount (mg/g lyophilized powder) | |
|---|---|---|
| | Cyclotetrasaccharide | ISOELITE P (control) |
| Methanol | 6.71 | 2.92 |
| Ethanol | 17.26 | 8.92 |
| Acetic acid | 67.74 | 30.57 |

As evident from the results in Table 25, it was revealed that cyclotetrasaccharide had inclusion ability about 2-folds higher than that of the branched cyclodextrin by weight.

Experiment 33

Sweetening Power

A crystalline cyclotetrasaccharide, penta- to hexa-hydrate, obtained by the method in Experiment 24, was dissolved in deionized water to obtain a 10% (w/v) aqueous solution of cyclotetrasaccharide as a standard test solution for sweetening power. Using aqueous solutions with different concentrations of a commercialized granulated sugar, a sensory test by five panelists was conducted. As a result, the sweetening power of cyclotetrasaccharide was about 20% of that of sucrose.

Experiment 34

Digestion Test

Using a crystalline cyclotetrasaccharide, penta- to hexa-hydrate, obtained by the method in Experiment 14, the digestibility of cyclotetrasaccharide by salivary amylase, synthetic gastric juice, amylopsin, or intestinal mucosal enzyme in a test tube, i.e., an in vitro test, was carried out in accordance with the method as reported by K. Okada et al. in *JOURNAL OF JAPANESE SOCIETY OF NUTRITION AND FOOD SCIENCE*, Vol. 43, No. 1, pp. 23–29 (1990). As a control, maltitol known as a substantially non-digestive saccharide was used. The results are in Table 26.

TABLE 26

| | Decomposition percentage (%) by digestive enzyme | |
|---|---|---|
| Digestive enzyme | Cyclotetrasaccharide | Maltitol (Control) |
| Salivary amylase | 0.0 | 0.0 |
| Synthetic gastric juice | 0.0 | 0.0 |
| Amylopsin | 0.0 | 0.0 |
| Small intestinal mucosal enzyme | 0.74 | 4.0 |

As evident from the results in Table 26, cyclotetrasaccharide was not digested by salivary amylase, synthetic gastric juice, and amylopsin, but slightly digested by intestinal mucosal enzyme in a digestibility as low as 0.74% that corresponded to ⅕ of that of maltitol, a hardly digestible saccharide, as a control. These results confirmed that cyclotetrasaccharide is a substantially undigestible saccharide.

Experiment 35

Fermentation Test

Using a crystalline cyclotetrasaccharide, penta- to hexa-hydrate, obtained by the method in Experiment 24, the fermentability of cyclotetrasaccharide by an internal content of rat cecum was tested in accordance with the method by T. Oku in "*Journal of Nutritional Science and Vitaminology*", Vol. 37, pp. 529–544 (1991). The internal content of rat cecum was collected by anesthetizing a Wister male rat with ether, allowing the rat to die, collecting the internal content under anaerobic conditions, and suspending the resultant with 4-fold volumes of a 0.1 M aqueous solution of sodium bicarbonate. Cyclotetrasaccharide was added in an amount of about 7% by weight to the weight of the internal contents of rat cecum, and the contents of cyclotetrasaccharide, which still remained just after and 12 hours after the addition of the internal contents, were quantified on gas chromatography. As a result, the contents of cyclotetrasaccharide of the former and latter were respectively 68.0 mg and 63.0 mg per one gram of the internal contents of rat cecum, revealing that 93% of the administered cyclotetrasaccharide remained without being fermented. These data confirmed that cyclotetrasaccharide is a substantially non-fermentable saccharide.

Experiment 36

Assimilation Test

Using a crystalline cyclotetrasaccharide, penta- to hexa-hydrate, obtained by the method in Experiment 24, the assimilability of cyclotetrasaccharide by different intestinal bacteria was examined in accordance with the method disclosed in "*Intestinal Flora and Dietary Factors*", edited by Tomotari MITSUOKA, published by Japan Scientific Societies Press, Tokyo, Japan, (1984). About $10^7$ CFU (colony forming units) of pre-cultured fresh microorganisms were inoculated into five milliliters of PYF medium supplemented with 0.5% cyclotetrasaccharide, and cultured at 37° C. for four days under anaerobic conditions. As a control, glucose was used as an easily assimilable saccharide. The assimilability was judged to be negative (−) when the post culture had a pH of 6.0 or higher and judged to be positive (+) when the post culture had a pH of below 6.0. The judgement of assimilability was confirmed by quantifying the saccharide remained in the culture by the anthrone method and determining the lowered content of saccharide. The results are in Table 27.

TABLE 27

| | Assimilability | |
|---|---|---|
| Strain of intestinal microorganism | Cyclotetrasaccharide | Glucose (control) |
| *Bacteroides vulgatus* JCM 5826 strain | − | + |
| *Bifidobacterium adolescentis* JCM 1275 strain | − | + |
| *Clostridium perfringens* JCM 3816 strain | − | + |
| *Escherichia coli* IFO 3301 strain | − | + |
| *Eubacterium aerofaciens* ATCC 25986 strain | − | + |
| *Lactobacillus acidophilus* JCM 1132 strain | − | + |

As evident from the results in Table 27, it was confirmed that cyclotetrasaccharide was not assimilated by any of the strains tested, but glucose as a control was assimilated by any of the strains tested. Thus, cyclotetrasaccharide was confirmed to be a substantially non-assimilable saccharide by intestinal microorganisms.

Experiment 37

Acute Toxicity Test

The acute toxicity of a crystalline cyclotetra-saccharide, penta- to hexa-hydrate, obtained by the method in Experiment 24, was tested by orally administering it to mice. As a result, it was revealed that cyclotetrasaccharide had relatively low toxicity and did not induce death of mouse even when administered at a highest possible dose. Based on this, the $LD_{50}$ of cyclotetrasaccharide was at least 50 g/kg mouse body weight.

Based on the results in Experiments 33 to 37, cyclotetrasaccharide is not substantially assimilated or absorbed by living bodies when orally taken and can be expected to be used as a non- or low-caloric edible material in diet sweeteners, fillers for sweeteners with a relatively high sweetening power, and viscosity agents, fillers and bodies for diet food products; and it can be also used as an edible fiber and food material for substituting fats.

The following Example A describes the process for producing cyclotetrasaccharide and saccharide compositions comprising the same, and Example B describes the composition comprising the cyclotetrasaccharide or the saccharide composition:

EXAMPLE A-1

A microorganism of the species *Bacillus globisporus* C11, FERM BP-7144, was cultured by a fermentor for 48 hours in accordance with the method in Experiment 6. After completion of the culture, the resulting culture was filtered with an SF membrane to remove cells, followed by collecting about 18 L of a culture supernatant. Then the culture supernatant was concentrated with a UF membrane to collect about one liter of a concentrated enzyme solution containing 30.2 units/ml of α-isomaltosyl-transferring enzyme. Panose commercialized by Hayashibara Biochemical Laboratories, Inc., Okayama, Japan, was dissolved in water to give a concentration of 10%, and the aqueous solution was adjusted to pH 6.0 and at 35° C., and admixed with two units/g panose of α-isomaltosyl-transferring enzyme, followed by enzymatic reaction for 36 hours. The reaction mixture was heated to 95° C. for 10 min, and then cooled and filtered. The filtrate was in a usual manner decolored with an activated charcoal, desalted and purified with ion exchangers in H- and OH-forms, and then concentrated, dried, and pulverized into a powder containing cyclotetrasaccharide in a yield of about 91%, d.s.b.

Since the product contains, on a dry solid basis, 34% glucose, 2.1% isomaltose, 2.3% panose, 45.0% cyclotetrasaccharide, 4.8% isomaltosylpanose, 1.8% isomaltosylpanoside, and 10.0% other saccharides, and has a mild sweetness, adequate viscosity, moisture-retaining ability, and inclusion ability, it can be advantageously used in compositions such as food products, cosmetics, and pharmaceuticals as a sweetener, taste-improving agent, quality-improving agent, syneresis-preventing agent, stabilizer, filler/excipient, inclusion agent, or base for pulverization.

EXAMPLE A-2

"SUNMALT®", a maltose powder produced by Hayashibara, Okayama, Japan, was prepared into a 30% aqueous maltose solution which was then admixed with "TRANSGLUCOSIDASE L AMANO™", an α-glucosidase commercialized by Amano Pharmaceutical Co., Ltd., Aichi, Japan, in an amount of 0.08% to the maltose, d.s.b., and adjusted to pH 5.5, followed by enzymatic reaction at 55° C. for 18 hours. Thereafter, the reaction mixture was heated to inactivate the remaining enzyme, adjusted to pH 6.0 and 35° C., admixed with two units/g solids, d.s.b., of a crude α-isomaltosyl-transferring enzyme prepared by the method in Example A-1, and enzymatically reacted for 36 hours. The resulting reaction mixture was heated to and kept at 95° C. for 10 min, and then cooled, and filtered. The filtrate was decolored with an activated charcoal in a usual manner, desalted and purified with ion-exchange resins in H and OH-forms, and concentrated into an about 70% syrup in a yield of about 92%, d.s.b.

Since the product contains, on a dry solid basis, 32.5% glucose, 15.7% maltose, 9.8% isomaltose, 4.0% maltotriose, 0.3% panose, 1.6% isomaltotriose, 17.5% cyclotetrasaccharide, 1.2% isomaltosylpanose, 0.7% isomaltosylpanoside, and 16.7% of other saccharides and has a mild sweetness, adequate viscosity, moisture-retaining ability, and inclusion ability, it can be advantageously used in compositions such as food products, cosmetics and pharmaceuticals as a sweetener, taste-improving agent, quality-improving agent, syneresis-preventing agent, stabilizer, filler/excipient, inclusion agent, or base for pulverization.

EXAMPLE A-3

Pullulan, produced by Hayashibara Co., Okayama, Japan, was prepared into a 5% aqueous pullulan solution which was then admixed with β-amylase produced by Seikagaku-Kogyo Co., Ltd., Tokyo, Japan, and pullulanase produced by Hayashibara Biochemical Laboratories, Inc., Okayama Japan, in respective amounts of 500 and 20 units/g pullulan, d.s.b., adjusted to pH 6.0, and enzymatically reacted at 45° C. for 48 hours. Thereafter, the reaction mixture was heated to inactivate the remaining enzymes, and then adjusted to pH 6.0 and 35° C., admixed with two units/g solids of a purified α-isomaltosyl-transferring enzyme prepared by the method in Experiment 4, and enzymatically reacted for 36 hours. The resulting reaction mixture was heated to and kept at 95° C. for 10 min, and then cooled, and filtered. The filtrate was decolored with an activated charcoal in a usual manner, desalted and purified with ion-exchange resins in H and OH-forms, and concentrated into an about 70% syrup in a yield of about 90%, d.s.b.

Since the product contains, on a dry solid basis, 10.7% glucose, 62.7% maltose, 0.1% maltotriose, 22.6% cyclotetrasaccharide, 1.0% isomaltosylmaltose, and 2.9% of other saccharides and has a mild sweetness, adequate viscosity, moisture-retaining ability, and inclusion ability, it can be advantageously used in compositions such as food products, cosmetics, and pharmaceuticals as a sweetener, taste-improving agent, quality-improving agent, syneresis-preventing agent, stabilizer, filler/excipient, inclusion agent, or base for pulverization.

EXAMPLE A-4

Corn starch was prepared into a 33% starch suspension which was then admixed with 0.1% calcium carbonate, adjusted to pH 6.5, admixed with 0.2%/g starch of "TERMAMYL", an α-amylase preparation, produced by Novo Industri A/S, Copenhagen, Denmark, and enzymatically reacted at 95° C. for 15 min. Thereafter, the mixture was autoclaved at 120° C. for 20 min, instantly cooled to about 55° C., admixed with 1,000 units/g starch of an isoamylase produced by Hayashibara Biochemical Laboratories, Inc., Okayama, Japan, and 60 units/g starch of β-amylase produced by Nagase Biochemicals, Ltd., Kyoto, Japan, and enzymatically reacted for 24 hours. Thereafter, the reaction mixture was heated to inactivate the remaining enzymes, adjusted to give a solid concentration of 30%, pH 5.5 and 55° C., and then admixed with 0.08% of "TRANSGLU-COSIDASE L AMANO™", an α-glucosidase, per one gram maltose, d.s.b., and enzymatically reacted for 18 hours. Thereafter, the reaction mixture was heated to inactivate the remaining enzyme, adjusted to pH 6.0 and 35° C., and then admixed with two units/g solids of a purified α-isomaltosyl-transferring enzyme prepared by the method in Experiment 7, and allowed to react for 36 hours. The resulting reaction mixture was heated to and kept at 95° C. for 10 min, and then cooled and filtered. The filtrate was in a usual manner decolored with an activated charcoal, desalted and purified with ion-exchange resins in H and OH-forms, and concentrated into an about 70% syrup in a yield of about 90%, d.s.b.

Since the product contains, on a dry solid basis, 25.1% glucose, 13.8% maltose, 13.9% isomaltose, 3.5% maltotriose, 0.2% panose, 2.0% isomaltotriose, 14.5% cyclotetrasaccharide, 2.5% isomaltosylpanose, 1.7% isomaltosylpanoside, and 22.8% of other saccharides and has a mild sweetness, adequate viscosity, moisture-retaining ability, and inclusion ability, it can be advantageously used in compositions such as food products, cosmetics, and pharmaceuticals as a sweetener, taste-improving agent, quality-improving agent, syneresis-preventing agent, stabilizer, filler/excipient, inclusion agent, or base for pulverization.

EXAMPLE A-5

A cyclotetrasaccharide powder obtained by the method in Example A-1 was prepared into a 5% solution, adjusted to give a pH of 5.0 and a temperature of 45° C., admixed with "TRANSGLUCOSIDASE L AMANO™", an α-glucosidase, and "GLUCOZYME", a glucoamylase preparation produced by Nagase Biochemicals, Ltd., Kyoto, Japan, in respective amounts of 1,500 and 75 units/g solids, and enzymatically reacted for 24 hours. The reaction mixture was heated to and kept at 95° C. for 10 min, and then cooled and filtered. The filtrate was in a usual manner decolored with an activated charcoal, desalted and purified with ion-exchange resins in H and OH-forms, and concentrated into an about 60% syrup. The saccharide solution thus obtained was fractionated by using a column packed with "AMBER-LITE CR-1310 (Na-form)", an ion-exchange resin produced by Japan Organo Co., Ltd., Tokyo, Japan. The procedure was as follows: The resin was packed in 4 jacketed-stainless steel columns having an inner diameter of 5.4 cm, and the columns were cascaded in series to give a total gel-bed depth of 20 m. The columns were heated to give an inner column temperature of 60° C., and fed with 5% (v/v) of the saccharide solution while keeping at the temperature, and the saccharide solution was fractionated by feeding to the columns with 60° C. hot water at an SV (space velocity) of 0.13 to collect fractions rich in cyclotetrasaccharide under the monitoring of the saccharide composition of eluate on HPLC. Thus a high cyclotetrasaccharide content solution was obtained in a yield of 28%, d.s.b. The solution contained about 99% cyclotetrasaccharide, d.s.b.

The above solution was concentrated into an about 70% solution, placed in a crystallizer, admixed with, as a seed, about two percent of cyclotetrasaccharide, penta- to hexa-hydrate, and then gradually cooled to obtain a massecuite with a degree of crystallization of about 45%. The massecuite was sprayed from a nozzle equipped on the top of a spraying tower at a pressure of 150 kg/cm². In the spraying step, the massecuite was simultaneously ventilated with 85° C. hot air sent from the top of the spraying tower, and the resultant crystalline powder was collected on a metal wire netting conveyer provided on the basement of the spraying tower, and gradually moved out of the tower while a stream of 45° C. hot air was passing upwards through the metal wire netting. The resultant crystalline powder was injected in an ageing tower and aged for 10 hours to complete the crystallization and drying, followed by recovering a powdered cyclotetrasaccharide, penta- to hexa-hydrate.

The product does not substantially show reducibility, cause amino carbonyl reaction, and have hygroscopicity, but has a satisfiable handleability, mild sweetness, adequate viscosity, moisture-retaining ability, inclusion ability, and insubstantial digestibility, it can be advantageously used in compositions such as food products, cosmetics, and pharmaceuticals as a sweetener, low-caloric food material, taste-improving agent, flavor-improving agent, quality-improving agent, syneresis-preventing agent, stabilizer, filler/excipient, inclusion agent, or base for pulverization.

EXAMPLE A-6

In accordance with the method in Example A-5, a cyclotetrasaccharide syrup obtained by the method in Example A-3 was treated with α-glucosidase and glucoamylase, and then in a usual manner filtered, decolored with an activated charcoal, desalted with ion-exchange resins in H- and OH-forms, and concentrated to obtain a 65% saccharide solution. In accordance with the method in Example A-5, the saccharide solution was fractionated by using a column packed with a strong-acid cation exchange resin to collect fractions rich in cyclotetra-saccharide. Thus a high cyclotetrasaccharide content solution was obtained in a yield of about 10.5%, d.s.b. The solution contained about 98% cyclotetrasaccharide, d.s.b.

The above solution was concentrated into an about 80% solution which was then placed in a crystallizer and admixed with, as a seed crystal, one percent of cyclotetrasaccharide, penta- to hexa-hydrate, followed by crystallizing the contents at 80° C. for five min while stirring. The resultant mixture was transferred to an aluminum container and aged at ambient temperature for 24 hours to form a block. The resultant block was pulverized by a cutting machine and subjected to a fluidized-bed drying to obtain a powdered cyclotetrasaccharide, penta- to hexa-hydrate.

The product does not substantially show reducibility, cause amino carbonyl reaction, and have hygroscopicity, but has a satisfiable handleability, mild sweetness, adequate viscosity, moisture-retaining ability, inclusion ability, and insubstantial digestibility, it can be advantageously used in compositions such as food products, cosmetics, and pharmaceuticals as a sweetener, low-caloric food material, taste-improving agent, quality-improving agent, syneresis-preventing agent, stabilizer, filler/excipient, inclusion agent, or base for pulverization.

EXAMPLE A-7

A high cyclotetrasaccharide content solution, obtained by the method in Example A-6, was allowed to continuously crystallize while concentrating. The resulting massecuite was separated by a basket-type centrifuge to obtain crystals which were then sprayed with a small amount of water for washing to obtain a high purity cyclotetrasaccharide, penta- to hexa-hydrate, in a yield of about 55%, d.s.b.

The product, a high purity cyclotetrasaccharide, penta- to hexa-hydrate, with a purity of 98% or higher, has a quite low reducibility, substantially neither-cause the amino carbonyl reaction nor exhibit hygroscopicity, but has a satisfactory handleability, mild low sweetness, adequate viscosity, moisture-retaining ability, inclusion ability, and insubstantial digestibility, it can be advantageously used in compositions such as food products, cosmetics, pharmaceuticals, industrial reagents, and chemical materials as a sweetener, low-caloric food material, taste-improving agent, flavor- and taste-improving agent, quality-improving agent, syneresis-preventing agent, stabilizer, discoloration-preventing agent, filler/excipient, inclusion agent, and base for pulverization.

EXAMPLE A-8

Corn starch was prepared into a 33% starch suspension, admixed with calcium carbonate to give a concentration of 0.1%, adjusted to pH 6.5, admixed with 0.2%/g starch of "TERMAMYL 60L", an α-amylase preparation, produced by Novo Industri A/S, Copenhagen, Denmark, and enzymatically reacted at 95° C. for 15 min. Thereafter, the mixture was autoclaved at 120° C. for 20 min, instantly cooled to about 55° C., adjusted to pH 5.5, admixed with 500 units/g starch of an isoamylase produced by Hayashibara Biochemical Laboratories, Inc., Okayama, Japan, and 60 units/g starch of p-amylase produced by Nagase Biochemicals, Ltd., Kyoto, Japan, and enzymatically reacted for 24 hours. Thereafter, the reaction mixture was heated to inactivate the remaining enzymes, and then admixed with 0.08% of "TRANSGLUCOSIDASE L AMANO™", an α-glucosidase preparation, per one gram of solids, d.s.b., and 1.5 units/g solids, d.s.b., of a purified α-isomaltosyl-transferring enzyme obtained by the method in Experiment 11, and enzymatically reacted for 48 hours. Thereafter, the reaction mixture was heated to and kept at 95° C. for 10 min, cooled and filtered. The filtrate was in a usual manner decolored with an activated charcoal, desalted and purified with ion-exchange resins in H and OH-forms, and concentrated into an about 70% syrup in a yield of about 90%, d.s.b.

Since the product contains, on a dry solid basis, 23.7% glucose, 13.8% maltose, 14.1% isomaltose, 3.2% maltotriose, 0.3% panose, 2.1% isomaltotriose, 14.0% cyclotetrasaccharide, 2.4% isomaltosylpanose, 1.9% isomaltosylpanoside, and 24.5% of other saccharides, and has a mild sweetness, adequate viscosity, moisture-retaining ability, and inclusion ability, it can be advantageously used in compositions such as food products, cosmetics, and pharmaceuticals as a sweetener, taste-improving agent, quality-improving agent, syneresis-preventing agent, stabilizer, filler/excipient, inclusion agent, or base for pulverization.

EXAMPLE A-9

A microorganism of the species *Arthrobacter ramosus* S1, FERM BP-7592, was cultured by a fermentor for 48 hours in accordance with the method in Experiment 14. After completion of the culture, about 20 L of the resulting culture was filtered with an SF membrane to remove cells, and the filtrate was concentrated with a UF membrane to obtain about one liter (eight units/ml) of a crude α-isomaltosyl-transferring enzyme solution of the present invention. Panose was dissolved in water into a 25% panose solution, adjusted to pH 5.5 and 45° C., admixed with the above crude enzyme solution to give 1.5 units/g panose of the enzyme, and enzymatically reacted for 48 hours. The reaction mixture was heated to and kept at 95° C. for 10 min, cooled and filtered. The filtrate was in a usual manner decolored with an activated charcoal, desalted and purified with ion-exchange resins in H and OH-forms, concentrated, dried, and pulverized to obtain a cyclotetrasaccharide-containing powder in a yield of about 93%, d.s.b.

Since the product contains, on a dry solid basis, 33.3% glucose, 2.5% isomaltose, 2.0% panose, 44.5% cyclotetrasaccharide, 5.2% isomaltosylpanose, 1.3% isomaltosylpanoside, and 11.3% of other saccharides, and has a mild sweetness, adequate viscosity, moisture-retaining ability, and inclusion ability, it can be advantageously used in a variety of compositions such as food products, cosmetics, pharmaceuticals as a sweetener, taste-improving agent, quality-improving agent, syneresis-preventing agent, stabilizer, discoloration-preventing agent, filler/excipient, inclusion agent, and base for pulverization.

EXAMPLE B-1

Sweetener

To 0.8 part by weight of a crystalline tetrasaccharide, penta- to hexa-hydrate, obtained by the method in Example A-7, were homogeneously added 0.2 part by weight of "TREHA®", a crystalline trehalose hydrate commercialized by Hayashibara Shoji Inc., Okayama, Japan, 0.01 part by weight of "αG SWEET™" (α-glycosyl stevioside commercialized by Toyo Sugar Refining Co., Tokyo, Japan), and 0.01 part by weight of "ASPARTAME" (L-aspartyl-L-phenylalanine methyl ester), and the resulting mixture was fed to a granulator to obtain a sweetener in a granule form. The product has a satisfactory sweetness and an about two-fold higher sweetening power of sucrose. Since crystalline cyclotetrasaccharide, penta- to hexa-hydrate, is hardly digestible and fermentable and is substantially free of calorie, i.e., the calorie of the product is about 1/10 of that of sucrose with respect to sweetening power. In addition, the product is stable and substantially free from quality deterioration even when stored at ambient temperature. Thus, the product can be suitably used as a high quality low-caloric and less cariogenic sweetener.

EXAMPLE B-2

Hard Candy

One hundred parts by weight of a 55% (w/v) sucrose solution was admixed while heating with 50 parts by weight of a syrup containing cyclotetrasaccharide obtained by the method in Example A-2. The mixture was then concentrated by heating under reduced pressure up to give a moisture content of less than 2%, and the concentrate was mixed with 0.6 part by weight of citric acid and an adequate amount of a lemon flavor, followed by forming in a usual manner the resultant into the desired product. The product is a stable, high quality hard candy which has a satisfactory mouth feel, taste, and flavor, less adsorbs moisture, and neither causes crystallization of sucrose nor induces melting.

EXAMPLE B-3

Chewing Gum

Three parts by weight of a gum base were melted by heating to an extent to be softened and then admixed with two parts by weight of anhydrous crystalline maltitol, two parts by weight of xylitol, two parts by weight of a crystalline cyclotetrasaccharide, penta- to hexa-hydrate, obtained by the method in Example A-7, and one part by weight of hydrous trehalose, and further mixed with adequate amounts of a flavor and a color. The mixture was in a usual manner kneaded by a roll and then shaped and packed to obtain the desired product. The product thus obtained is a relatively low cariogenic and caloric chewing gum with a satisfactory texture, taste, and flavor.

EXAMPLE B-4

Sweetened Condensed Milk

In 100 parts by weight of a fresh milk was dissolved two parts by weight of a crystalline powder of cyclotetrasaccharide, penta- to hexa-hydrate, obtained by the method in Example A-5, and two parts by weight of sucrose, and the solution was sterilized by heating using a plate heater and then concentrated to give a concentration of 70%. The concentrate was aseptically canned to obtain the desired product. Since the product has a mild sweetness and a satisfactory flavor and taste, it can be arbitrarily used for seasoning fruit, coffee, cocoa, tea, etc.

EXAMPLE B-5

Lactic Acid Beverage

One hundred and seventy-five parts by weight of a skim milk powder, 130 parts by weight of a syrup containing cyclotetrasaccharide, obtained by the method in Example A-4, and 50 parts by weight of "NYUKAOLIGO®", a high lactosucrose content powder commercialized by Hayashibara Shoji Inc., Okayama, Japan, were dissolved in 1,150 parts by weight of water. The resulting solution was sterilized at 65° C. for 30 min, then cooled to 40° C., inoculated in a usual manner with 30 parts by weight of lactic acid bacteria as a starter, and incubated at 37° C. for eight hours to obtain a beverage with lactic acid bacteria. The product can be suitably used as a lactic acid beverage which has a satisfactory flavor and taste, contains oligosaccharides and cyclotetrasaccharide, stably retains the lactic acid bacteria, promotes the growth of the bacteria for controlling the intestinal conditions.

EXAMPLE B-6

Powdered Juice

Thirty-three parts by weight of an orange juice powder, prepared by spray drying, were well mixed by stirring with 50 parts by weight of a powdered cyclotetrasaccharide, penta- to hexa-hydrate, obtained by the method in Example A-7, 10 parts by weight of anhydrous crystalline maltitol, 0.65 part by weight of anhydrous citric acid, 0.1 part by weight of malic acid, 0.2 part by weight of 2-O-α-D-glucosyl-L-ascorbic acid, 0.1 part by weight of sodium citrate, 0.5 part by weight of pullulan, and an adequate amount of a powdered flavor. The mixture was pulverized into a minute powder which was then placed in a fluidized-bed granulator adjusted to blow air to 40° C., sprayed with, as a binder, an adequate amount of a high cyclotetrasaccharide content solution obtained by the method in Example A-5, granulated for 30 min, weighed, and packed to obtain the desired product. The product is a powdered juice having about 30% of a fruit juice. Also the product has a high product value because it is a high quality, low caloric juice free from unpleasant taste and smell.

EXAMPLE B-7

Custard Cream

One hundred parts by weight of corn starch, 100 parts by weight of cyclotetrasaccharide obtained by the method in Example A-2, 60 parts by weight of hydrous trehalose, 40 parts by weight of sucrose, and one part by weight of salt were sufficiently mixed, and then further mixed with 280 parts by weight of eggs, followed by stirring. To the resulting mixture was gradually admixed with 1,000 parts by weight of a boiling milk, and then continued stirring over a fire. The heating was stopped when the corn starch completely gelatinized and the whole contents became semi-transparent, followed by cooling the resultant, admixing with an adequate amount of a vanilla flavor, and then weighing, injecting, and packing the resultant mixture to obtain the desired product. The product is a high quality custard cream having a smooth gloss and a satisfactory flavor and taste, where the retrogradation of starch is well inhibited.

EXAMPLE B-8

Chocolate

Forty parts by weight of a cacao paste, 10 parts by weight of a cacao butter, and 50 parts by weight of a crystalline cyclotetrasaccharide monohydrate, obtained by the method in Experiment 15, were mixed, and the mixture was fed to a refiner to lower the granule size and then placed in a conche and kneaded at 50° C. over two days and nights. During the processing, 0.5 part by weight of lecithin was added to and well dispersed therein. Thereafter, the resulting mixture was adjusted to 31° C. by a thermo controller, and then poured into a mold just before solidification of butter, deairated, and solidified by passing through a cooling tunnel kept at 10° C. The solidified contents were removed from the mold and packed into the desired product. The product has substantially no hygroscopicity, satisfactory color, gloss, and internal texture; smoothly melts in the mouth; and has a high quality sweetness and a mild flavor and taste. Also the product is useful as a low cariogenic, low caloric chocolate.

EXAMPLE B-9

Uiro-no-moto (a Premix of uiro (Sweet Rice Jelly))

To 90 parts by weight of rice powder were added 20 parts by weight of corn starch, 70 parts by weight of anhydrous crystalline maltitol, 50 parts by weight of a powder containing cyclotetrasaccharide obtained by the method in Example A-1, and four parts by weight of pullulan. The resulting mixture was mixed to homogeneity to obtain an uiro-no-moto. The product and adequate amounts of matcha (a green tea powder) and water were kneaded and then placed in a container and steamed up for 60 min to obtain a uiro with matcha. Since the product has a satisfactory gloss, mouth feel, and flavor and taste, it can be suitably used as a long shelf-life, low caloric uiro where the retrogradation of starch is well inhibited.

EXAMPLE B-10

An (a Bean Jam)

Ten parts by weight of adzuki beans as a material were boiled in a usual manner after the addition of water, removed the astringency, lye, and water-soluble impurities to obtain about 21 parts by weight of raw bean jam with un-pasted adzuki beans. To the raw bean jam were added 14 parts by weight of sucrose, five parts by weight of a syrup containing cyclotetrasaccharide obtained by the method in Example A-3, and four parts by weight of water, and the resulting mixture was boiled, admixed with a small amount of salad oil, and then kneaded up without pasting the remaining un-pasted adzuki beans to obtain about 35 parts by weight of the desired product of an. Since the product has a satisfactory stability, mouth feel, flavor and taste, and does not substantially cause syneresis nor induces excessive color of baking, it can be arbitrarily used as a material for confectioneries such as a bean jam bun, "manju" (a kind of Japanese confectionery with bean jam), bean-jam-filled wafer, and ice cream/candy.

EXAMPLE B-11

Bread

One hundred parts by weight of wheat flour, two parts by weight of a yeast, five parts by weight of sucrose, one part by weight of a powder containing cyclotetrasaccharide obtained by the method in Example A-1, and 0.1 part by weight of a yeast food, were kneaded with water in a usual manner, fermented at 26° C. for two hours, aged for 30 min, and then baked up. The product is a high quality bread having satisfactory color and texture, as well as adequate elasticity and mild sweetness.

EXAMPLE B-12

Ham

To one thousand parts by weight of ham meat slices were added and ground to homogeneity 15 parts by weight of salt and three parts by weight of potassium nitrate, and the resultant slices were piled and allowed to stand in a cold-storage room over a day and night. Thereafter, the resultant slices were first soaked in a salt solution, consisting of 500 parts by weight of water, 100 parts by weight of salt, three parts by weight potassium nitrate, 40 parts by weight of a powder containing cyclotetrasaccharide, penta- to hexa-hydrate, obtained by the method in Example A-5, and an adequate amount of a spice, for seven days in a cold-storage room, and then washed with cold water in a usual manner, tied up with a string, smoked, cooked, cooled, and packaged to obtain the desired product. The product is a high quality ham having a satisfactory hue, taste, and flavor.

EXAMPLE B-13

Powdery Peptide

One part by weight of 40% of "HINUTE S", a peptide solution of edible soy beans commercialized by Fuji Oil Co., Ltd., Tokyo, Japan, was mixed with two parts by weight of a powder containing cyclotetrasaccharide, hepta- to hexa-hydrate, obtained by the method in Example A-6, and the resultant mixture was placed in a plastic vessel, dried in vacuo at 50° C., and pulverized into a powdery peptide. The product having a satisfactory flavor and taste can be arbitrary used as a material for confectioneries such as premixes, sherbets and ice creams/candies, as well as a substantially non-digestible edible fiber and a material for controlling intestinal conditions which are used for fluid diets for oral administration and intubation feeding.

EXAMPLE B-14

Powdery Egg Yolk

Egg yolks prepared from fresh eggs were sterilized at 60–64° C. by a plate-heat sterilizer, and one part by weight of the resultant liquid was mixed with four parts by weight of a powder containing anhydrous crystalline cyclotetrasaccharide powder, obtained in accordance with the method in Experiment 16. The resultant mixture was transferred to a vessel and allowed to stand overnight to form a block while the cyclotetra-saccharide was allowing to be converted into crystalline cyclotetrasaccharide, hepta- to hexa-hydrate. The block thus obtained was pulverized by a cutter into a powdery egg yolk.

The product can be arbitrary used as a material for low caloric confectioneries for premixes, ice creams/sherbets, and emulsifiers, as well as a substantially non-digestible edible fiber and a material for controlling intestinal conditions which are used for fluid diets for oral administration and intubation feeding. Also the product can be arbitrarily used as a skin-beautifying agent, hair restorer, etc.

EXAMPLE B-15

Bath Salt

One part by weight of a peel juice of "yuzu" (a Chinese lemon) was admixed with 10 parts by weight of a powder containing anhydrous crystalline cyclotetrasaccharide obtained in accordance with the method in Experiment 16, followed by crystallizing to form crystalline cyclotetrasaccharide, hepta- to hexa-hydrate, ageing the formed crystal, and pulverizing the aged crystal to obtain a powder of crystalline cyclotetra-saccharide, hepta- to hexa-hydrate, containing a yuzu peel extract.

A bath salt was obtained by mixing five parts by weight of the above powder with 90 parts by weight of grilled salt, two parts by weight of hydrous crystalline trehalose, one part by weight of silicic anhydride, and 0.5 part by weight of "αG HESPERIDIN", α-glucosyl hesperidin commercialized by Hayashibara Shoji, Inc., Okayama, Japan.

The product is a high quality bath salt enriched with yuzu flavor and used by diluting with hot water by 100–10,000 times, and it moisturizes and smooths the skin and effectively prevents you from feeling coldness after a bath.

EXAMPLE B-16

Cosmetic Cream

Two parts by weight of polyoxyethylene glycol monostearate, five parts by weight of glyceryl monostearate, self-emulsifying, two parts by weight of a powder of crystalline cyclotetrasaccharide, hepta- to hexa-hydrate, obtained by the method in Example A-5, one part by weight of "αG RUTIN", α-glucosyl rutin commercialized by Hayashibara Shoji, Inc., Okayama, Japan, one part by weight of liquid petrolatum, 10 parts by weight of glyceryl tri-2-ethylhexanoate, and an adequate amount of an antiseptic were dissolved by heating in a usual manner. The resultant solution was admixed with two parts by weight of L-lactic acid, five parts by weight of 1,3-butylene glycol, and 66 parts by weight of refined water, and the resultant mixture was emulsified by a homogenizer and admixed with an adequate amount of a flavor under stirring conditions to obtain a cosmetic cream. Since the product exhibits an antioxidant activity and has a relatively high stability, it can be advantageously used as a high quality sunscreen, skin-refining agent, skin-whitening agent, etc.

EXAMPLE B-17

Toothpaste

A toothpaste was obtained by mixing 45 parts by weight of calcium secondary phosphate, 1.5 parts by-weight of sodium lauryl sulfate, 25 parts by weight of glycerine, 0.5 part by weight of polyoxyethylene sorbitan laurate, 15 parts by weight of a syrup containing cyclotetrasaccharide obtained by the method in Example A-2, 0.02 part by weight of saccharine, 0.05 part by weight of an antiseptic, and 13 parts by weight of water. The product, where the inherent unpleasant taste has been improved, has a satisfactory feeling after use without lowering the detergent power of the surfactant.

EXAMPLE B-18

Solid Preparation for Fluid Diet

One hundred parts by weight of a power of crystalline cyclotetrasaccharide, penta- to hexa-hydrate, obtained by the method in Example A-6, 200 parts by weight of hydrous crystalline trehalose, 200 parts by weight of a high maltotetraose content powder, 270 parts by weight of an egg yolk powder, 209 parts by weight of a skim milk powder, 4.4 parts by weight of sodium chloride, 1.8 parts by weight of potassium chloride, four parts by weight of magnesium sulfate, 0.01 part by weight of thiamine, 0.1 part by weight of sodium L-ascorbate, 0.6 part by weight of vitamin E acetate, and 0.04 part by weight of nicotinamide were mixed. Twenty-five gram aliquots of the resulting composition were injected into moisture-proof laminated small bags which were then heat sealed to obtain the desired product.

The product, a fluid diet enriched with substantially non-digestible edible fiber due to cyclotetra-saccharide, has a satisfactory intestinal-controlling action. One bag of the product is dissolved in about 150–300 ml of water into a fluid diet and arbitrarily used by administering orally or intubationally into nasal cavity, stomach, intestines, etc., to supplement energy to living bodies.

EXAMPLE B-19

Dermal External Lotion

The following ingredients as indicated below were mixed in a usual manner to prepare lotion:

| | |
|---|---|
| One percent of an aqueous hyaluronic acid solution | 18 parts by weight |
| A powder containing crystalline cyclotetrasaccharide, hepta- to hexa-hydrate, obtained by the method in Example A-6 | 1 part by weight |
| DL-Serine | 0.05 part by weight |
| Maltitol | 0.2 part by weight |
| Glycerine | 2 parts by weight |
| p-Oxymethyl benzoate | 0.05 part by weight |
| Potassium hydroxide | 0.01 part by weight |
| Polyoxyethylene oleyl ether (15 E.O.) | 0.3 part by weight |
| Ethanol | 3 parts by weight |
| Flavor | An adequate amount |
| Refined water | q.s. |
| Total | 100 parts by weight |

The product, having an improved water-penetrating ability and moisture-retaining ability to the skin, is useful as a basic skin care. Since the product exerts a relatively significant action on softening the skin corneum, it is useful as a cosmetic for cold season or for middle and old-age generations.

EXAMPLE B-20

Dermal External Cream

A solution "A" was prepared by mixing to homogeneity under stirring conditions 0.3 part by weight of methylpolysiloxane, six parts by weight of stearic acid, 3.5 parts by weight of oil-soluble glyceryl monostearate, 2.5 parts by weight of squalane, 5.5 parts by weight of cetyl 2-ethyl hexanoate, three parts by weight of polyoxyethylene monostearate (20 E.O.). While a solution "B" was prepared by adding an adequate amount of water to two parts by weight of 95% glycerin, two parts by weight of maltitol, and 3.5 parts by weight of a powder containing crystalline cyclotetrasaccharide, hepta- or hexa-hydrate obtained by the method in Example A-7, and the mixture was heated at 70° C. for dissolving the contents sufficiently. The solutions "A" and "B" were mixed and stirred sufficiently, and then admixed with 34 parts by weight of refined water and emulsified by an emulsifying mixer in a usual manner. The resulting emulsion was cooled to 35° C., admixed with two parts by weight of 2-O-α-D-glucosyl-L-ascorbic acid and an adequate amount of citric acid, and then adjusted to pH of about 6, and further admixed with refined water to make a total volume of 100 parts by weight for obtaining a cream.

The product is useful as a basic skin care because it exerts an advantageous moisture-retaining ability on the skin and does not substantially stimulate the skin. Also the product has a feature that it stably keeps its emulsified-condition and stands for a relatively long period of time for storing.

EXAMPLE B-21

Liquid Composition for Skin Cleaning

Twenty parts by weight of 30% sodium N-cocoyl-N-methyl taurate, five parts by weight of 2-alkyl-N-carboxymethyl-N-hydroxyethylimidazolinium betaine, and four parts by weight of polyoxyethylene dioleate methyl glucoside were mixed for dissolving under a heating condition of 70° C., and further admixed with two parts by weight of a powder containing crystalline cyclotetrasaccharide, penta- to hexa-hydrate, obtained by the method in Example A-6, 0.2 part by weight of propylparaben, one part by weight of 10% aqueous citric acid solution, and water in an amount sufficient to give a total amount of 100 parts by weight. Thus, a liquid composition was obtained.

Since the composition advantageously, effectively cleans the skin and satisfactory imparts moisture to the skin, it is useful as a daily usable body soap.

EXAMPLE B-22

Bath Composition

Sixty parts by weight of dried sodium sulfate, 30 parts by weight of sodium bicarbonate, five parts by weight of trehalose, five parts by weight of a powder containing crystalline cyclotetrasaccharide, penta- to hexa-hydrate, obtained by the method in Example A-6, one part by weight of a citrus seasoning flavor, and 0.5 part by weight of food blue No. 2 (indigo carmine) were mixed to homogeneity to obtain a powdered deodorant according to the present invention.

In use, about 20 g of the product are added to and dissolved in 100 L of hot water in a bath tab. Since the product effectively moistens the skin, satisfactorily inhibits

EXAMPLE B-23

Tablet

To 50 parts by weight of aspirin (acetylsalicylic acid) were added 14 parts by weight of a crystalline cyclotetrasaccharide, penta- to hexa-hydrate, obtained by the method in Example A-7, and four parts by weight of corn starch, and the mixture was sufficiently mixed. Thereafter, the resulting mixture was tabletted by a tabletting machine in a usual manner to obtain a tablet, 5.25 mm in thickness, 680 mg weight.

The product, prepared by employing the property of cyclotetrasaccharide as an excipient, has substantially no hygroscopicity and a satisfactory physical strength and degradability in water.

EXAMPLE B-24

Sugar Coated Tablet

A crude tablet as a core, 150 mg weight, was sugar coated with a first solution consisting of 40 parts by weight of a crystalline cyclotetrasaccharide, penta- to hexa-hydrate, obtained by the method in Example A-7, two parts by weight of pullulan having an average molecular weight of 200,000, 30 parts by weight of water, 25 parts by weight of talc, and three parts by weight of titanium oxide until the total weight increased to about 230 mg. The resultant was then sugar coated with a second solution consisting of 65 parts by weight of a fresh preparation of the same powder of crystalline cyclotetrasaccharide, penta- to hexa-hydrate, one part by weight of pullulan, and 34 parts by weight of water, and glossed with a liquid wax to obtain a sugar coated tablet having a satisfactory gloss and appearance. The product has a relatively high shock-tolerance and retains its high quality for a relatively-long period of time.

EXAMPLE B-25

Ointment for Treating Trauma

To 100 parts by weight of a powder of crystalline cyclotetrasaccharide, penta- to hexa-hydrate, obtained by the method in Example A-6, and 300 parts by weight of maltose was added 50 parts by weight of methanol dissolving three parts by weight of iodine, and further added 200 parts by weight of a 10% (w/v) aqueous pullulan solution to obtain the desired product with an adequate extensibility and adhesiveness. The product is a high-valued ointment which the dispersion of iodine and methanol is well inhibited by cyclotetrasaccharide and which relatively less changes during storage.

Because the product exerts a sterilizing action by iodine and, based on maltose, acts as an energy-supplementing agent to living cells, it shortens the curing term and well cures the affected parts and surfaces.

INDUSTRIAL APPLICABILITY

As described above, the present invention relates to a novel α-isomaltosyl-transferring enzyme, and its process and uses. By using the novel α-isomaltosyl-transferring enzyme of the present invention, an industrially useful cyclotetra-saccharide having the structure of cyclo{→6)-α-D-glucopyranosyl-(1→3)-α-D-glucopyranosyl-(1→46)-α-D-glucopyranosyl-(1→3)-α-D-glucopyranosyl-(1→}, as well as saccharides and compositions which both comprise the cyclotetrasaccharide can be easily produced on an industrial scale. The cyclotetrasaccharide per se and the saccharides comprising the cyclotetrasaccharide do not substantially have reducibility or have only a lesser reducibility, neither cause the amino carbonyl reaction nor exhibit hygroscopicity, but have a mild sweetness, adequate viscosity, inclusion ability, and insubstantial assimilability. Thus, they can be advantageously used in compositions such as food products, cosmetics, pharmaceuticals as a sweetener, material for low caloric foods, taste-improving agent, flavor-retaining ability, quality-improving agent, syneresis-preventing agent, stabilizer, filler/excipient, inclusion agent, and base for pulverization.

The present invention, having these outstanding functions and effects, is a significantly important invention that greatly contributes to this art.

---

The invention claimed is:

1. An isolated α-isomaltosyl-transferring enzyme which forms a cyclotetrasaccharide having the structure of cyclo{→6)-α-D-glucopyranosyl-(1→3)-α-D-glucopyranosyl-(1→6)-α-D-glucopyranosyl-(1→3)-α-D-glucopyranosyl-(1→} from a saccharide having a glucose polymerization degree of at least three and having both the α-1,6 glucosidic linkage as a linkage at the non-reducing end and the α-1,4 glucosidic linkage other than the linkage at the non-reducing end, said enzyme being not activated by $Ca^{2+}$ and not inhibited by EDTA.

2. The isolated α-isomaltosyl-transferring enzyme of claim 1, wherein said saccharide is one or more saccharides selected from the group consisting of panose and isomaltosylmaltose.

3. The isolated α-isomaltosyl-transferring enzyme of claim 1 or 2, which is derived from a microorganism.

4. An isolated α-isomaltosyl-transferring enzyme of claim 1 which has the following physicochemical properties:

(1) Action

Forming a cyclotetrasaccharide having the structure of cyclo{→6)-α-D-glucopyranosyl-(1→3)-α-D-glucopyranosyl-(1→6)-α-D-glucopyranosyl-(1→3)-α-D-glucopyranosyl-(1→} from a saccharide having a glucose polymerization degree of at least three and having both the α-1,6 glucosidic linkage as a linkage at the non-reducing end and the α-1,4 glucosidic linkage other than the linkage at the non-reducing end;

(2) Molecular weight

About 82,000 to about 136,000 daltons when determined on sodium dodecyl sulfate (SDS) polyacrylamide gel electrophoresis (PAGE);

(3) Isoelectric point (pI)

About 3.7 to about 8.3 when determined on isoelectrophoresis using ampholine;

(4) Optimum temperature

About 45° C. to about 50° C. when reacted at a pH of 6.0 for 30 min;

(5) Optimum pH

About 5.5 to about 6.5 when reacted at 35° C. for 30 min;

(6) Thermal stability

Substantially not inactivated at temperatures of about 45° C. or lower when reacted at a pH of 6.0 for 60 min; and (7) pH Stability Substantially not inactivated at pHs about 4.5 to about 9.0 when reacted at 4° C. for 24 hours.

5. The isolated α-isomaltosyl-transferring enzyme of claim 1, which has one or more amino acid sequences selected from the group consisting of SEQ ID NOs:1 to 8.

6. The isolated α-isomaltosyl-transferring enzyme of claim 1, which is a purified or crude enzyme.

7. A process for producing α-isomaltosyl-transferring enzyme, of claim 1, which comprises the steps of:

culturing in a nutrient culture medium a microorganism capable of genus *Bacillus* or *Arthrobacter*, capable of producing the α-isomaltosyl-transferring enzyme of claim 1 to produce said enzyme; and collecting the produced α-isomaltosyl-transferring enzyme from the resulting culture.

8. A method of α-isomaltosyl-transferring reaction, which comprises a step of contacting the α-isomaltosyl-transferring enzyme of claim 1 with a solution comprising a saccharide having a glucose polymerization degree of at least three and having both the α-1,6 glucosidic linkage as a linkage at the non-reducing end and the α-1,4 glucosidic linkage other than the linkage at the non-reducing end.

9. The method of claim 8, wherein said saccharide is one or more saccharides selected from the group consisting of panose and isomaltosylmaltose.

10. The method of claim 8, wherein said enzyme is allowed to act on said saccharide to form a saccharide-transferred product in the presence of one or more acceptors selected from the group consisting of D-glucose, D-xylose, L-xylose, D-galactose, D-fructose, D-arabinose, D-fucose, L-sorbose, L-rhamnose, methyl-α-glucopyranoside, methyl-α-glucopyranoside, D-ribose, L-sorbose, D-psicose, sorbitol, xylitol, arabitol, ribitol, erythritol, maltose, maltotriose, maltotetraose, maltopentaose, isomaltose, isomaltotriose, α,α-trehalose, α,α-trehalose, kojibiose, nigerose, cellobiose, gentibiose, isopanose, maltitol, maltotriitol, lactose, sucrose, erlose, isomaltosylglucoside, and L-ascorbic acid.

11. A process for producing a cyclotetrasaccharide having the structure of cyclo{→6)-α-D-glucopyranosyl-(1→3)-α-D-glucopyranosyl-(1→6)-α-D-glucopyranosyl-(1→3)-α-D-glucopyranosyl-(1→} or a saccharide composition comprising the same, which comprises a step of:

contacting the α-isomaltosyl-transferring enzyme of claim 1 with a solution comprising a saccharide having a glucose polymerization degree of at least three and having both the α-1,6 glucosidic linkage as a linkage at the non-reducing end and the α-1,4 glucosidic linkage other than the linkage at the non-reducing end.

12. The process of claim 11, wherein said saccharide is one or more saccharides selected from the group consisting of panose and isomaltosylmaltose.

13. The process of claim 11, wherein one or more enzymes selected from the group consisting of α-amylase, α-amylase, glucoamylase, and α-glucosidase are allowed to act on the resulting mixture obtained after the action of α-isomaltosyl-transferring enzyme.

14. The process of claim 11, wherein one or more purification methods selected from the group consisting of decoloration, desalting, fractionation by column chromatography, separation with a membrane, fermentation treatment using microorganisms, and decomposition and removal by an alkaline treatment are applied to the resulting mixture obtained after the action of α-isomaltosyl-transferring enzyme.

15. The process of claim 11, wherein said cyclotetrasaccharide or the saccharide composition comprising the same contains at least 10% (w/w), on a dry solid basis, of a cyclotetrasaccharide having the structure of cyclo{→6)-α-D-glucopyranosyl-(1→3)-α-D-glucopyranosyl-(1→6)-α-D-glucopyranosyl-(1→3)-α-D-glucopyranosyl-(1→}.

16. The process of claim 11, wherein said cyclotetrasaccharide or the saccharide composition comprising the same is in the form of a syrup, massecuite, amorphous powder, amorphous solid, crystalline powder, or crystalline solid.

17. The process of claim 16, wherein said crystal is prepared by crystallizing in an aqueous solution without using any organic solvent.

18. The process of claim 7, wherein said microorganism of the genus *Bacillus* or *Arthrobacter* is selected from the group consisting of *Bacillus globisporus* C9, FERM BP-7143; *Bacillus globisporus* C11, FERM BP-7144, *Bacillus globisporus* N75, FERM BP-7591; *Arthrobacter ramosus* S1, FERM BP-7592; and *Arthrobacter globiformis* A19, FERM EP-7590, which all have been deposited in International Patent Organism Depositary National Institute of Advanced Industrial Science and technology; and mutants thereof.

* * * * *